United States Patent
Williams et al.

(10) Patent No.: US 11,486,010 B2
(45) Date of Patent: Nov. 1, 2022

(54) GENETICALLY ENCODED BIOSENSORS FOR DETECTION OF POLYKETIDES

(71) Applicant: NORTH CAROLINA STATE UNIVERSITY, Raleigh, NC (US)

(72) Inventors: Gavin J. Williams, Raleigh, NC (US); Christian Kasey, Raleigh, NC (US); Yiwei Li, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 129 days.

(21) Appl. No.: 16/099,749

(22) PCT Filed: Aug. 17, 2017

(86) PCT No.: PCT/US2017/031962
§ 371 (c)(1),
(2) Date: Nov. 8, 2018

(87) PCT Pub. No.: WO2017/196983
PCT Pub. Date: Nov. 16, 2017

(65) Prior Publication Data
US 2019/0085416 A1 Mar. 21, 2019

Related U.S. Application Data
(60) Provisional application No. 62/334,204, filed on May 10, 2016.

(51) Int. Cl.
*C12Q 1/6897* (2018.01)
*C07K 14/245* (2006.01)
*C12N 15/09* (2006.01)

(52) U.S. Cl.
CPC .......... *C12Q 1/6897* (2013.01); *C07K 14/245* (2013.01); *C12N 15/09* (2013.01)

(58) Field of Classification Search
None
See application file for complete search history.

(56) References Cited

U.S. PATENT DOCUMENTS

2004/0209270 A1  10/2004  Eberz

FOREIGN PATENT DOCUMENTS

| WO | 2005033287 A3 | 8/2005 |
| WO | 2014158594 A1 | 10/2014 |
| WO | 2014093402 A3 | 7/2015 |

OTHER PUBLICATIONS

Meinhardt et al. Rheostats and Toggle Switches for Modulating Protein Function. Dec. 30, 2013. PLOS One. vol. 8, Issue 12, e83502, pp. 1-11. (Year: 2013).*

Miller et al. Computational predictors fail to identify amino acid substitution effects at rheostat positions. Jan. 30, 2017. Scientific Reports. vol. 7, No. 41329, pp. 1-13. (Year: 2017).*

International Search Report and Written Opinion in PCT/US2017/031962, dated Aug. 17, 2017. 10 pages.

Brakhage, Axel A. et al. Use of Reporter Genes to Identify Recessive trans-Acting Mutations Specifically Involved in the Regulation of Aspergillus nidulans Penicillin Biosynthesis Genes. Journal of Bacteriology, May 1995., p. 2781-2788.

Feng, Tingting et al. Insights into Resistance Mechanism of the Macrolide Biosensor Protein MphR (A) Binding to Macrolide Antibiotic Erythromycin by Molecular Dynamics Simulation. J Comput Aided Mol Des, Aug. 6, 2015. 14 pages.

Fu, Y et al. Study of Transcriptional Regulation Using a Reporter Gene Assay. Methods Mol Biol. 2006; 313:257-64.

Altschul et al. (1977) Gapped BLAST and PSI-BLAST: a new generation of protein database search programs. Nuc. Acids Res. 25:3389-3402.

Altschul et al. (1990) Basic local alignment search tool. J. Mol. Biol. 215:403-410.

Beaucage and Carruthers, Deoxynucleoside phosphoramidites—a new class of key intermediates for deoxypolynucleotide synthesis. Tetrahedron Lett., 1981, 22:1859-1862.

Boghigian BA, et al. Multi-factorial Engineering of Heterologous Polyketide Production in *Escherichia coli* Reveals Complex Pathway Interactions. Biotechnology and Bioengineering. 2011; 108(6): 1360-71.

Gardner L, et al. Photochemical Control of Bacterial Signal Processing Using a Light-activated Erythromycin. Molecular Biosystems. 2011;7(9):2554-7.

Henikoff and Henikoff (1989) Amino acid substitution matrices from protein blocks. Proc. Natl. Acad. Sci. USA 89:10915.

Jiang M., Pfeifer, B. Metabolic and Pathway Engineering to Influence Native and Altered Erythromycin Production Through *E. coli*. Metabolic Engineering. 2013;19:42-9.

Karlin and Altschul (1993) Applications and statistics for multiple high-scoring segments in molecular sequences. Proc. Natl. Acad. Sci. USA 90:5873-5877.

Matteucci, et al., Synthesis of deoxyoligonucleotides on a polymer support. J. Am. Chem. Soc., 103:3185, 1981.

Miller ES, et al. Description of the erythromycin- producing bacterium Arthrobacter sp. strain NRRL B-3381 as Aeromicro- bium erythreum gen. nov., sp. Nov. International Journal of Systematic Bacteriology. 1991;41: 363-368.

Mohrle, V. et al. Biosensor-guided screening for macrolides. Anal. Bioanal. Chem. Jul. 2007;388(5-6):1117-25.

Montemiglio, LC, et al. Redirecting P450 EryK Specificity by Rational Site-directed Mutagenesis. Biochemistry. 2013; 52(21) 3678-87.

Noguchi N, et al. Regulation of Transcription of the mph(A) Gene for Macrolide 2'-Phosphotransferase I in *Escherichia coli*; Characterization of the Regulatory Gene mphR(A). Journal of Bacteriology. 2000;182(18):5052-5058.

Reeves AR, et al. Engineering precursor flow for increased erythromycin production in Aeromicrobium erythreum. Metabolic Engineering. 2004;6(4): 300-12.

Rogers, J. et al., Synthetic biosensors for precise gene control and real-time monitoring of metabolites, Nucleic Acids Research, 2015, vol. 43, No. 15, 7648-7660.

(Continued)

*Primary Examiner* — Nancy J Leith
*Assistant Examiner* — Tiffany Nicole Grooms
(74) *Attorney, Agent, or Firm* — Meunier Carlin & Curfman LLC

(57) ABSTRACT

The present disclosure relates to high-throughput detection of polyketides using genetically encoded biosensors.

14 Claims, 28 Drawing Sheets

Specification includes a Sequence Listing.

(56) References Cited

OTHER PUBLICATIONS

Savino, C, et al. Investigating the Structural Plasticity of a Cytochrome P450 Three-dimensional Structures of P450 EryK and Binding to its Physiological Substrate. Journal of Biological Chemistry. 2009;284(42) 29170-9.

Sundermann U, et al. Enzyme-directed Mutasynthesis: a Combined Experimental and Theoretical Approach to Substrate Recognition of a Polyketide Synthase. ACS Chemical Biology. 2013;8(2):443-50.

Zhang H, et al. Complete Biosynthesis of Erythromycin A and Designed Analogs Using *E. coli* as a Heterologous Host. Cell Chemistry & Biology. 2010;17(11):1232-40.

Zheng J, et al. Structure and Function of the Macrolide Biosensor Protein, MphR(A), With and Without Erythromycin. Journal of Molecular Biology. 2009;3 87(5):1250-60.

* cited by examiner

10-DML (12)
~10% conversion (in vivo)

Narbonolide (13)
~10% conversion (in vivo)

Tylactone (14)
~90% conversion (in vitro)

GdEB (15)
~10% conversion (in vitro)
~10% conversion (in vitro)

Brefeldin A (16)
~5% conversion (in vitro)

WT-pMLCmR

Grey=colonies

GENETICALLY ENCODED BIOSENSORS FOR DETECTION OF POLYKETIDES

CROSS REFERENCE TO RELATED APPLICATIONS

This application is a national stage application filed under 35 U.S.C. § 371 of PCT/US2017/031962 filed May 10, 2017, which claims the benefit of U.S. Provisional Patent Application Ser. No. 62/334,204 filed May 10, 2016, the disclosure of which is expressly incorporated herein by reference.

STATEMENT REGARDING FEDERALLY SPONSORED RESEARCH

This invention was made with government support under grant number GM104258 awarded by the National Institutes of Health. The government has certain rights in the invention.

FIELD

The present disclosure relates to high-throughput detection of polyketides using genetically encoded biosensors.

BACKGROUND

Polyketides are a large group of diverse molecules that display broad and potent biological activities. Access to large quantities of polyketides and analogues thereof is critical for the discovery of new biological activities, optimization of pharmacological properties, and to probe discovery and development. Biosynthetic approaches to polyketide production offer enormous potential and several benefits compared to traditional chemical approaches. The scaffolds of many polyketides are constructed by type I polyketide synthases (PKSs). These are large multifunctional protein complexes organized in a modular fashion. Each module is responsible for the selection and installation of a ketide into the polyketide. The number, identity, and order of modules describe the structure of the corresponding polyketide. These scaffolds are often further elaborated by tailoring enzymes to afford the mature, biologically active natural product. Accordingly, these systems offer the potential for the synthesis of large quantities of polyketides via microbial fermentation and combinatorial synthesis of analogues by mixing and matching modules and tailoring enzymes. However, the sheer size, mechanistic diversity, and poor understanding of how specificity and catalysis are controlled by type I PKSs render rational design of new pathways difficult. For example, many hybrid PKSs designed to produce polyketide analogues fail or are less active than wild-type machinery. Consequently, the full synthetic potential of type I PKSs has yet to be realized. Synthetic biology and directed evolution offer an opportunity to overcome these challenges by testing the functions of large libraries of variants. Yet, the ability of synthetic biology and directed evolution approaches to be applied to polyketides is extremely limited because there are no generally applicable high-throughput tools available for screening polyketides, particularly those encoded by type I PKSs. Regulatory proteins such as transcription factors have been used as effective devices for sensitive and specific detection of various small molecules. Engineered transcription factors have been described for sensing several small molecules, including dicarboxylic acids, alcohols, and a lactone, but none have been reported for the complex products of type I PKSs.

The biosensor systems, cells, and methods disclosed herein address these and other needs.

SUMMARY

Described herein is a platform technology that comprises genetically-encoded biosensors and methods for detection of polyketides using mutated MphR gene sequences. Such biosensors provide a scalable, economic, high-throughput, and broadly applicable means to specifically identify a target polyketide of interest from a complex mixture of molecules.

In one aspect, disclosed herein is a biosensor system comprising:
a nucleic acid encoding a genetically modified MphR gene sequence, wherein the nucleic acid comprises at least one genetic mutation when compared to the wild-type MphR gene sequence; and
a reporter gene whose transcription is under the control of a promoter region which is regulated by the MphR transcription factor.

In one aspect, disclosed herein is a genetically modified host cell comprising:
a nucleic acid encoding a genetically modified MphR gene sequence, wherein the nucleic acid comprises at least one genetic mutation when compared to the wild-type MphR gene sequence; and
a reporter gene whose transcription is under the control of a promoter region which is regulated by the MphR transcription factor.

In one aspect, provided herein is a method for detecting a polyketide, comprising:
introducing into a cell:
i. a nucleic acid encoding a genetically modified MphR gene sequence, wherein the nucleic acid comprises at least one genetic mutation when compared to the wild-type MphR gene sequence; and
ii. a reporter gene whose transcription is under the control of a promoter region which is regulated by the MphR transcription factor; and
detecting the polyketide based on the differential expression of the reporter gene in comparison to a cell comprising a wild-type MphR gene sequence.

In one aspect, provided herein is a method of screening for genetic mutations in a target gene, comprising:
introducing into a cell:
i. a nucleic acid encoding a genetically modified MphR gene sequence, wherein the nucleic acid comprises at least one genetic mutation when compared to the wild-type MphR gene sequence; and
ii. a reporter gene whose transcription is under the control of a promoter region which is regulated by the MphR transcription factor;
introducing at least one mutation into a target gene; and
identifying a cell comprising the target gene mutation based on the differential expression of the reporter gene in comparison to a cell comprising the wild-type target gene.

BRIEF DESCRIPTION OF THE DRAWINGS

The accompanying figures, which are incorporated in and constitute a part of this specification, illustrate several aspects described below.

(FIG. 1A) Structures of selected polyketides that are detected by wild-type (WT)

MphR. Erythromycin A (ErA) is the natural ligand. (FIG. 1B) Artificial MphR-GFP reporter system. In the presence of ErA, MphR changes conformation and stops inhibiting transcription from the PmphR operator, thus turning on reporter expression.

(FIG. 2A) Sensitivity of original clones A3, E7, and H4 towards erythromycin A. (FIG. 2B) Sensitivity of wild-type MphR and amino-acid change-only mutations towards erythromycin A. (FIG. 2C) Sensitivity of wild-type MphR and RBS-only mutations towards erythromycin A.

(FIG. 4A) WT MphR detects erythromycin A (ErA) but not the aglycone, 6 dEB. (FIG. 4B) Structures of the 12-membered macrolide YC-17 and macrolactone (aglycone) 10-DML. (FIG. 4C) Left, the MphR variant D3 detects YC-17 at concentrations ~100-fold lower than WT MphR; Right, neither WT or D3 MphR is activated by the aglycone 10-DML.

(FIG. 5A) An OMT with the requisite regioselectivity allows the single-step preparation of clarithromycin from ErA. (FIG. 5B) Role of naturally occurring OMTs that target polyketide sugar residues.

(FIG. 6A) Wild-type (WT) MphR does not discriminate ErA/clarithromycin across a 1000-fold concentration range. (FIG. 6B) MphR M1B10 provides higher GFP signal with clarithromycin vs. erythromycin A (ErA) across entire range of concentrations.

(FIG. 8A) Two genetic changes afford I, in low yield. (FIG. 8B) Biosensor-guided screening of large libraries of variants identify prototype pathways/strains with improved product titers.

(FIG. 9A) Phyr2 generated homology model for EryG, 93% of residues were modeled at >90% confidence. Residues involved in the SAM binding site (V88, G89, F90, G91, L92, G93, A94, D112, L113, G139, S140, A141, L157). Sticks: putative macrolide (ErA) binding residues (I188, G215, W221, W252, W256, K278, R279, L281, T282, S285, G286, K288, F296), determined by comparison to known acceptor binding sites for related OMTs. (FIG. 9B) Computationally predicted internal cavities of EryG using CAVER Analyst 1.0 (Outer probe 3.00 Å, Inner probe 1.90 Å). SAM binding site and putative erythromycin A (ErA) binding site are shown. (FIG. 9C) DnrK (PDB: 1TW3) acceptor binding site shown as sticks (E298, L299, R302, M303, F306, L307, Y341). Macrolide ligand shown space filled. (FIG. 9D) MycF (PDB: 4X7U) acceptor binding site shown as sticks (L32, Y49, M132, L134, Y137, V141).

(FIG. 10A) Reactions catalyzed by glycosyltransferases (GTs). (FIG. 10B) Genes responsible for the biosynthesis of a given polyketide are usually clustered on microbial genomes. (FIG. 10C) Feeding non-native aglycones into heterologous host with non-native NDP-sugar and GT genes. (FIG. 10D) Overall reaction catalyzed by DesVII/VIII is shown in the grey box, along with the natural aglycone substrates for this enzyme.

(FIG. 12A) MphR-WT responses to erythromycin A and semi-synthetic analogs. (FIG. 12B) MphR-A16T/T154M/M155K responses to erythromycin A and semi-synthetic analogs. Coding of macrolides show potential or actual points of semi-synthetic modification. (FIG. 12C) Structures for erythromycin A (compound 1), clarithromycin (compound 2), azithromycin (compound 3), and roxithromycin (compound 4).

(FIG. 21A) YC-17 sensitivity of B1 clone vs. WT. (FIG. 21B) Narbomycin sensitivity of G7 clone vs. WT. (FIG. 21C) Pikromycin sensitivity of B1 clone vs. WT.

DETAILED DESCRIPTION OF THE INVENTION

Figure 1A:
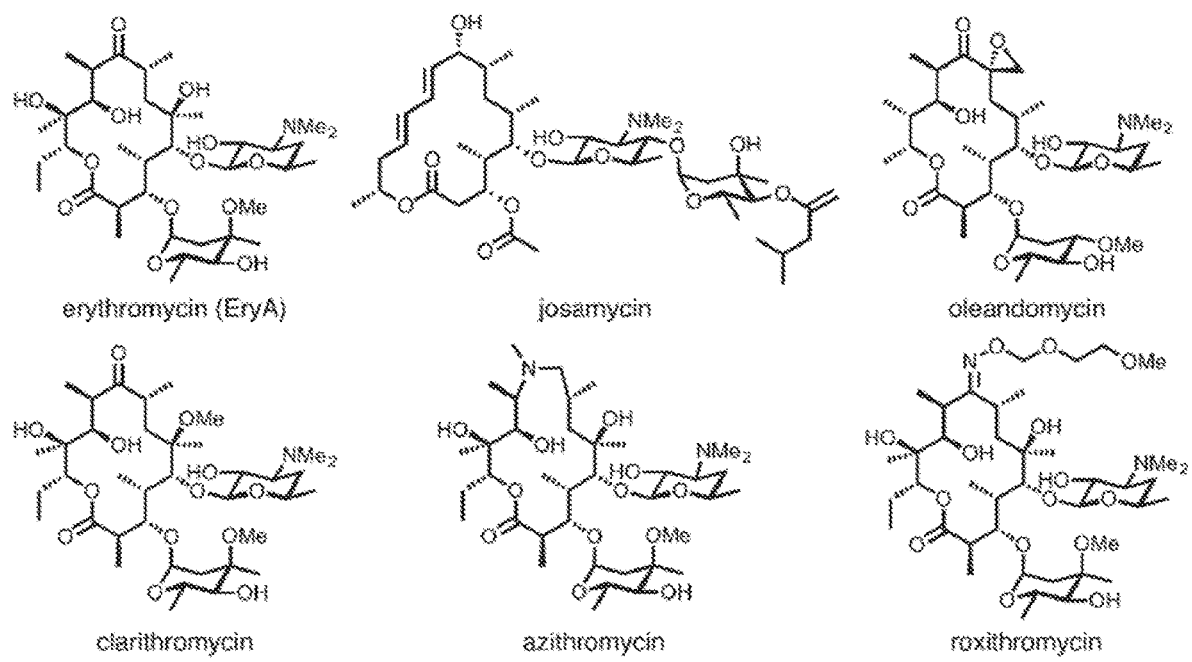
FIGS. 1A-1B. The MphR biosensor.

Described herein is a platform technology that comprises genetically-encoded biosensors and methods for detection of polyketides using mutated MphR gene sequences. Such biosensors provide a scalable, economic, high-throughput, and broadly applicable means to specifically identify a target polyketide of interest from a complex mixture of molecules.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

Terms used throughout this application are to be construed with ordinary and typical meaning to those of ordinary skill in the art. However, Applicant desires that the following terms be given the particular definition as defined below.

As used in the specification and claims, the singular form "a," "an," and "the" include plural references unless the context clearly dictates otherwise. For example, the term "a cell" includes a plurality of cells, including mixtures thereof.

As used herein, the terms "may," "optionally," and "may optionally" are used interchangeably and are meant to include cases in which the condition occurs as well as cases in which the condition does not occur.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.*, 22:1859-1862 (1981), or by the triester method according to Matteucci, et al., *J. Am. Chem. Soc.*, 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, *Biochemistry*, Third Ed., (1988), incorporated herein by reference for all purposes.

The term "polynucleotide" refers to a single or double stranded polymer composed of nucleotide monomers. In some embodiments, the polynucleotide is composed of nucleotide monomers of generally greater than 100 nucleotides in length and up to about 8,000 or more nucleotides in length.

The term "polypeptide" refers to a compound made up of a single chain of D- or L-amino acids or a mixture of D- and L-amino acids joined by peptide bonds.

The term "promoter" or "regulatory element" refers to a region or sequence determinants located upstream or downstream from the start of transcription and which are involved in recognition and binding of RNA polymerase and other proteins to initiate transcription. Promoters need not be of bacterial origin, for example, promoters derived from viruses or from other organisms can be used in the compositions, systems, or methods described herein The term "recombinant" refers to a human manipulated nucleic acid (e.g. polynucleotide) or a copy or complement of a human manipulated nucleic acid (e.g. polynucleotide), or if in reference to a protein (i.e, a "recombinant protein"), a protein encoded by a recombinant nucleic acid (e.g. polynucleotide). In embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature. For instance, human manipulated restriction sites or plasmid vector sequences may flank or separate the promoter from the second nucleic acid (e.g. polynucleotide). One of skill will recognize that nucleic acids (e.g. polynucleotides) can be manipulated in many ways and are not limited to the examples above.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The phrase "codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Such optimization includes replacing at least one, or more than one, or a significant number, of codons with one or more codons that are more frequently used in the genes of that selected organism.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

"Ribosome binding site" or "RBS" is also called the Shine Dalgarno sequence and generally has a sequence complementary to the 3' terminal of 16S rRNA. The ribosomal binding site is found in bacterial and archaeal messenger RNA, and is generally located about 8 bases upstream of the start codon AUG. In particular, the RBS sequence which appears at high frequency is AGGAGG or AAGGAGG (hereinafter these sequences are referred to as "consensus RBS sequences"), or a sequence homologous with "consensus RBS sequence". Although these sequences appear at various sites of genes, it is understood that the RBS sequences appear at high frequency in regions upstream of start codons. Also included in the term "RBS" is the RBS sequence from the MphR gene as disclosed herein ("AGAAGG"). Other functional RBS sequences can also be used in place of the specific sequences disclosed herein. When discussing nucleotide mutations in the RBS, the first A is labeled as nucleotide "1" and the final G is labelled as nucleotide "6". Alternatively, the mutations may sometimes referred to by their relative position to the ATG start codon. The basic structure of a prokaryote gene consists of a promoter which starts the synthesis of mRNA, a ribosome binding site which participates in the binding between mRNA and ribosomes and in the translation initiation, a start codon, a translation stop codon and a terminator which terminates the synthesis of mRNA. AUG codon is the most appropriate as a start codon. Since the start codons and coding regions are determined usually based upon a DNA sequence, in the present specification, the sequences of start codons and stop codons and sequences involved in the binding of ribosomes and mRNA are expressed as DNA sequences appropriately as well as RNA sequences, unless mentioned specifically.

The term "gene" or "gene sequence" refers to the coding sequence or control sequence, or fragments thereof. A gene may include any combination of coding sequence and control sequence, or fragments thereof. Thus, a "gene" as referred to herein may be all or part of a native gene. A polynucleotide sequence as referred to herein may be used interchangeably with the term "gene", or may include any coding sequence, non-coding, sequence or control sequence, fragments thereof, and combinations thereof. The term "gene" or "gene sequence" includes, for example, control sequences upstream of the coding sequence (for example, the ribosome binding site).

MphR Biosensors

Described herein is a platform technology that comprises genetically-encoded biosensors and methods to create them for detection of a class of small molecules called polyketides. Such biosensors provide a scalable, economic, high-throughput, and broadly applicable means to specifically identify a target polyketide of interest from complex mixtures of molecules. Polyketides are used extensively as drugs to treat human, animal, and plant diseases.

Examples of polyketides include, but are not limited to, macrolides, polyenes, enediynes, and aromatic polyketides. In some embodiments, the polyketide is a macrolide. In some embodiments, the polyketide is a 12-membered macrolide. In some embodiments, the polyketide is a 14-membered macrolide.

Due to their widespread use, polyketides are often produced in bacteria via genetic engineering. Detection of polyketides in microbial hosts remains a significant challenge however, and this limits the throughput and success of engineering approaches aimed at improving yields of polyketide and accessing new molecules. Thus, the main application of the present invention relates to the production of antibiotics, anticancer drugs, insecticides, anti-parasitics, anti-fungals, anti-cholesterol, and immunosuppressants in microbial hosts. Because the biosensors can be employed in a wide variety of contexts, other commercial applications include but are not limited to: (1) discovery of polyketide producing genes from collections of genomes; (2) identification and quantification of polyketide-based drugs, contaminants, and other molecules in environmental, clinical, and other research samples; and (3) isolation or removal of target polyketide compounds from complex mixtures.

Figure 1B:
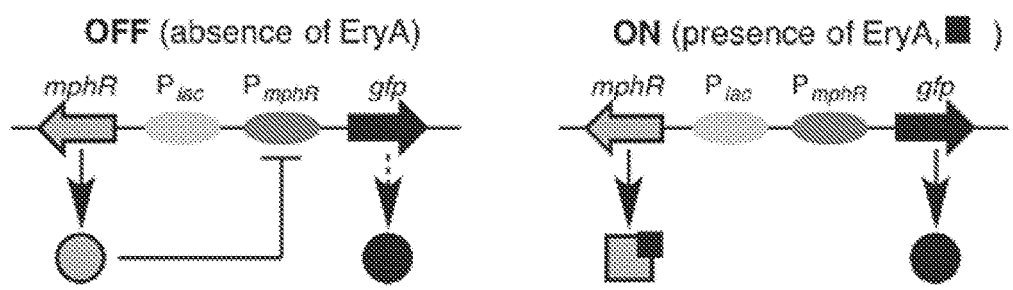
Figure 3A:
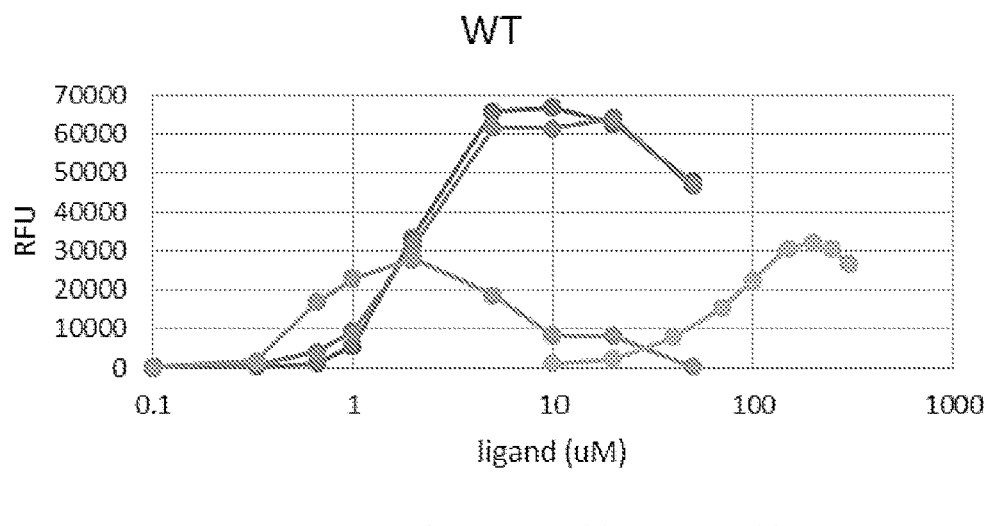
FIG. 3A. Erythromycin, clarithromycin, azithromycin, roxithromycin sensitivity with wild-type (WT) MphR.

The sensor is based on the MphR gene, which encodes a transcription factor. The natural role of wild-type (WT) MphR is to activate the expression of resistance genes in response to binding the polyketide antibiotic, erythromycin A (ErA, FIG. 1). Upon binding ErA, the MphR protein undergoes a conformational change that causes it to leave its cognate operator DNA sequence, thereby allowing RNA polymerase to transcribe the gene and produce the gene product. By placing the MphR gene sequence and its operator DNA into an artificial vector, MphR can be used to drive the expression of reporter proteins that produce fluorescent, luminescent, or chromogenic signals in the presence of erythromycin A (ErA) (FIG. 1(b)). However, compared to ErA, much higher concentrations of other polyketides, even those structurally related to ErA, are required to elicit strong reporter signals using WT MphR (FIG. 3(a)). Moreover, most polyketides are not detected by WT MphR at all. These features have severely restricted the utility of MphR as a biosensor for high-throughput analysis of polyketides. Disclosed herein is a panel of MphR variants that are utilized for the detection of specific, target polyketides. Such tailored biosensors enable a suite of high-throughput approaches to be applied to the engineering of polyketide biosynthesis in microbes.

In one embodiment, the operator DNA sequence is 5'-AATATAACCGACGTGACTGTTACATTTAGG-3 (SEQ ID NO: 27).

The genetically-encoded biosensors described here are unique in several aspects: (1) biosensors that respond to a broad variety of polyketides are not currently known; (2) biosensors that can discriminate between very closely related polyketide structures have not been described, (3) a strategy to engineer the ligand specificity and/or amount of MphR was developed that is efficient, novel, and non-obvious; and (4) other high-throughput analytical methods/tools to detect most polyketides are not available. Accordingly, high-throughput engineering approaches such as directed gene or enzyme evolution and synthetic biology have not been applied to the vast majority of polyketides due to the lack of suitable screening tools. Such strategies are critical to overcome the poor understanding of how to design and construct biosynthetic or chemical routes to new and existing antibiotics. In contrast, the biosensor-guided approach described herein can be applied to engineering the biosynthesis of a broad range of polyketides in potentially any microbial host, and could be generalized to other classes of natural products such as peptides, alkaloids, and terpenes. The invention disclosed herein can enable production of polyketide products rapidly and at lower cost than existing manufacturing routes, thus maximizing the return on investment and providing incentive to develop new antibiotics.

The biosensor platform is simple (consisting of two genes—one encodes the genetically modified MphR gene sequence and the other encodes a marker/reporter gene (for example, GFP) under the control of the MphR responsive promoter), scalable (genetically encoded so that the host microbe synthesizes all the parts), economic, ultra-high-throughput (millions of potential polyketide producing strains can be assayed using the biosensor), and can be easily adapted to target polyketides of interest (directed evolution is a powerful strategy to engineer the ligand specificity of proteins).

MphR is a repressor protein that controls the transcription of a gene cassette responsible for resistance to macrolide antibiotics via phosphorylation of the desosamine 2'-hydroxy group of ErA. Interestingly, MphR is also de-repressed by other macrolide antibiotics, including josamycin, oleandomycin, narbomycin, methymycin and pikromycin. This promiscuity provides a platform for creating tailored MphR variants for applications related to polyketide synthetic biology and directed evolution beyond those offered by the wild-type biosensor. For example, sensors may recognize a wide variety of polyketides, sensors may distinguish biosynthetic intermediates to allow specific detection of the desired mature product, and the binding affinity and dynamic range of a given biosensor can be tailored for specific applications.

In one aspect, disclosed herein is a biosensor system comprising:
a nucleic acid encoding a genetically modified MphR gene sequence, wherein the nucleic acid comprises at least one genetic mutation when compared to the wild-type MphR gene sequence; and
a reporter gene whose transcription is under the control of a promoter region which is regulated by the MphR transcription factor.

In some embodiments, the biosensor system further comprises a nucleic acid encoding an MphA gene sequence. In some embodiments, the biosensor system further comprises a nucleic acid encoding a portion of the mrx gene. In some embodiments, the biosensor system further comprises a nucleic acid encoding an MphA gene sequence and a portion of the mrx gene.

In one embodiment, the nucleic acid encoding the genetically modified MphR gene sequence and the reporter gene are located on one recombinant DNA vector. In one embodiment, the nucleic acid encoding the genetically modified MphR gene sequence and the reporter gene are located on one recombinant DNA vector.

In one embodiment, the reporter gene is a gene coding for chloramphenicol acetyltransferase, beta-galactosidase, luciferase or green fluorescent protein (GFP). In one embodiment, the reporter gene is a gene coding for green fluorescent protein (GFP). In one embodiment, the reporter gene is a gene coding for chloramphenicol acetyltransferase.

In some embodiments, the MphR mutation confers improved sensitivity for detecting erythromycin A. In one embodiment, the MphR genetic mutation encodes a nucleotide change in the ribosome binding site sequence. In one embodiment, the MphR genetic mutation encodes a nucleotide change in the ribosome binding site sequence selected from A1G, A1T, A1C, G2T, G2A, A3C, A3G, A4T, G5T, G6T, or a combination thereof. In one embodiment, the MphR genetic mutation encodes a nucleotide change in the ribosome binding site sequence selected from A1G, A4T, or a combination thereof. In one embodiment, the MphR genetic mutation encodes an A1G nucleotide change in the ribosome binding site sequence. In one embodiment, the MphR genetic mutation encodes an A4T nucleotide change in the ribosome binding site sequence.

In one embodiment, the MphR genetic mutation encodes a nucleotide change in the ribosome binding site sequence selected from A1T, G2T, A3C, or a combination thereof. In one embodiment, the MphR genetic mutation encodes a nucleotide change in the ribosome binding site sequence selected from A1C, G2T, A3G, or a combination thereof. In one embodiment, the MphR genetic mutation encodes a nucleotide change in the ribosome binding site sequence selected from G2A, G5T, or a combination thereof.

In one embodiment, the MphR genetic mutation encodes the amino acid change selected from T17R, T27G, Q65M, T27A, M59E, M59S, R22H, K35N, T49I, L89V, D98N, E109D, R122T, K132N, A151T, H184Q, T49I, L89V, D98N, E109D, or a combination thereof. In one embodiment, the MphR genetic mutation encodes the amino acid change selected from T17R, T27G, Q65M, T27A, M59E, M59S, R22H, K35N, or a combination thereof. In one embodiment, the MphR genetic mutation encodes the amino acid change selected from T49I, L89V, D98N, E109D, R122T, K132N, A151T, H184Q, T49I, L89V, D98N, E109D, or a combination thereof.

In some embodiments, the MphR mutation confers improved selectivity for detecting erythromycin A in comparison to other polyketides. In one embodiment, the MphR genetic mutation encodes the amino acid change selected from A16T, T154M, M155K, or a combination thereof. In one embodiment, the MphR genetic mutation encodes an A4T nucleotide change in the ribosome binding site sequence and an amino acid change selected from A16T, T154M, M155K, or a combination thereof.

In some embodiments, the MphR mutation confers improved selectivity for detecting erythromycin A in comparison to structurally similar precursors. In one embodiment, the MphR genetic mutation encodes the amino acid change selected from P4L, W107L, H193R, or a combination thereof.

In some embodiments, the MphR mutation confers improved sensitivity for detecting pikromycin. In one embodiment, the MphR genetic mutation encodes the amino acid change S106F.

In some embodiments, the MphR mutation confers improved sensitivity for detecting narbomycin. In one embodiment, the MphR genetic mutation encodes the amino acid change selected from V33L, A34S, R51C, or a combination thereof.

In some embodiments, the MphR mutation confers improved sensitivity for detecting clarithromycin. In one embodiment, the MphR genetic mutation encodes the amino acid change selected from T49I, L89V, D98N, E109D or a combination thereof. In one embodiment, the MphR genetic mutation encodes the amino acid change R122T. In one embodiment, the MphR genetic mutation encodes the amino acid change selected from R122T, K132N, A151T, H184Q, or a combination thereof. In one embodiment, the MphR genetic mutation encodes an A4T nucleotide change in the ribosome binding site sequence and an amino acid change selected from R122T, K132N, A151T, H184Q, or a combination thereof. In one embodiment, the MphR genetic mutation encodes the amino acid change selected from T49I, L89V, D98N, E109D, or a combination thereof.

In one aspect, disclosed herein is a genetically modified host cell comprising:
a nucleic acid encoding a genetically modified MphR gene sequence, wherein the nucleic acid comprises at least one genetic mutation when compared to the wild-type MphR gene sequence; and
a reporter gene whose transcription is under the control of a promoter region which is regulated by the MphR transcription factor.

In one embodiment, the nucleic acid encoding the genetically modified MphR gene sequence and the reporter gene are located on one recombinant DNA vector.

In one embodiment, the nucleic acid encoding the genetically modified MphR gene sequence and the reporter gene are located on one recombinant DNA vector.

In one embodiment, the reporter gene is a gene coding for chloramphenicol acetyltransferase, beta-galactosidase, luciferase or green fluorescent protein (GFP). In one embodiment, the reporter gene is a gene coding for green fluorescent protein (GFP). In one embodiment, the reporter gene is a gene coding for chloramphenicol acetyltransferase.

In one embodiment, the cell is *E. coli*. In one embodiment, the cell is *Streptomyces*. In one embodiment, the cell is *Streptomyces venezuelae*. In one embodiment, the cell is *Saccharopolyspora erythraea*.

In some embodiments, disclosed herein is a genetically modified MphR gene sequence comprising at least one mutation in the nucleotide sequence upstream of the ATG start codon of the MphR gene sequence, wherein the mutation confers increased sensitivity for detection of erythromycin A in comparison to the wild type MphR transcription factor.

In some embodiments, disclosed herein is a genetically modified MphR gene sequence comprising at least one mutation in the ribosome binding site sequence of the MphR gene sequence, wherein the mutation confers increased sensitivity for detection of erythromycin A in comparison to the wild type MphR transcription factor.

In some embodiments, disclosed herein is a genetically modified MphR gene sequence comprising at least one mutation in the MphR protein sequence, wherein the mutation confers increased sensitivity for detection of erythromycin A in comparison to the wild type MphR transcription factor.

In some embodiments, disclosed herein is a genetically modified MphR gene sequence comprising at least one mutation in the nucleotide sequence upstream of the ATG start codon of the MphR gene sequence, wherein the mutation confers increased sensitivity for detection of erythromycin A in comparison to the wild type MphR transcription factor.

In some embodiments, disclosed herein is a genetically modified MphR gene sequence comprising at least one mutation in the ribosome binding site sequence of the MphR gene sequence, wherein the mutation confers increased sensitivity for detection of erythromycin A in comparison to the wild type MphR transcription factor.

In some embodiments, disclosed herein is a genetically modified MphR gene sequence comprising at least one mutation in the MphR protein sequence, wherein the mutation confers increased selectivity for detection of erythromycin A in comparison to other polyketides.

In some embodiments, disclosed herein is a genetically modified MphR gene sequence comprising at least one mutation in the MphR protein sequence, wherein the mutation confers increased selectivity for detection of erythromycin A in comparison to structurally similar precursors.

In some embodiments, disclosed herein is a genetically modified MphR gene sequence comprising at least one mutation in the MphR protein sequence, wherein the mutation confers increased sensitivity for detection of pikromycin in comparison to the wild type MphR transcription factor.

In some embodiments, disclosed herein is a genetically modified MphR gene sequence comprising at least one mutation in the nucleotide sequence upstream of the ATG start codon of the MphR gene sequence, wherein the mutation confers increased sensitivity for detection of pikromycin in comparison to the wild type MphR transcription factor.

In some embodiments, disclosed herein is a genetically modified MphR gene sequence comprising at least one mutation in the ribosome binding site sequence of the MphR gene sequence, wherein the mutation confers increased sensitivity for detection of pikromycin in comparison to the wild type MphR transcription factor.

In some embodiments, disclosed herein is a genetically modified MphR gene sequence comprising at least one mutation in the MphR protein sequence, wherein the mutation confers increased sensitivity for detection of narbomycin in comparison to the wild type MphR transcription factor.

In some embodiments, disclosed herein is a genetically modified MphR gene sequence comprising at least one mutation in the nucleotide sequence upstream of the ATG start codon of the MphR gene sequence, wherein the mutation confers increased sensitivity for detection of narbomycin in comparison to the wild type MphR transcription factor.

In some embodiments, disclosed herein is a genetically modified MphR gene sequence comprising at least one mutation in the ribosome binding site sequence of the MphR gene sequence, wherein the mutation confers increased sensitivity for detection of narbomycin in comparison to the wild type MphR transcription factor.

In some embodiments, disclosed herein is a genetically modified MphR gene sequence comprising at least one mutation in the MphR protein sequence, wherein the mutation confers increased sensitivity for detection of YC-17 in comparison to the wild type MphR transcription factor.

In some embodiments, disclosed herein is a genetically modified MphR gene sequence comprising at least one mutation in the nucleotide sequence upstream of the ATG start codon of the MphR gene sequence, wherein the mutation confers increased sensitivity for detection of YC-17 in comparison to the wild type MphR transcription factor.

In some embodiments, disclosed herein is a genetically modified MphR gene sequence comprising at least one mutation in the ribosome binding site sequence of the MphR gene sequence, wherein the mutation confers increased sensitivity for detection of YC-17 in comparison to the wild type MphR transcription factor.

In one aspect, disclosed herein is a biosensor system comprising:
a nucleic acid encoding a genetically modified MphR transcription factor, wherein the nucleic acid comprises at least one genetic mutation when compared to the wild-type MphR gene sequence; and
a reporter gene whose transcription is under the control of a promoter region which is regulated by the MphR transcription factor.

In one aspect, disclosed herein is a genetically modified host cell comprising:
a nucleic acid encoding a genetically modified MphR transcription factor, wherein the nucleic acid comprises at least one genetic mutation when compared to the wild-type MphR gene sequence; and
a reporter gene whose transcription is under the control of a promoter region which is regulated by the MphR transcription factor.

In one aspect, provided herein is a method for detecting a polyketide, comprising:
introducing into a cell:
i. a nucleic acid encoding a genetically modified MphR transcription factor, wherein the nucleic acid comprises at least one genetic mutation when compared to the wild-type MphR gene sequence; and
ii. a reporter gene whose transcription is under the control of a promoter region which is regulated by the MphR transcription factor;
and
detecting the polyketide based on the differential expression of the reporter gene in comparison to a cell comprising a wild-type MphR transcription factor.

In one aspect, provided herein is a method of screening for genetic mutations in a target gene, comprising:
introducing into a cell:
i. a nucleic acid encoding a genetically modified MphR transcription factor, wherein the nucleic acid comprises at least one genetic mutation when compared to the wild-type MphR gene sequence; and
ii. a reporter gene whose transcription is under the control of a promoter region which is regulated by the MphR transcription factor;
introducing at least one mutation into a target gene; and
identifying a cell comprising the target gene mutation based on the differential expression of the reporter gene in comparison to a cell comprising the wild-type target gene.

MphR Biosensors: Methods

In one aspect, provided herein is a method for detecting a polyketide, comprising:
introducing into a cell:
i. a nucleic acid encoding a genetically modified MphR gene sequence, wherein the nucleic acid comprises at least one genetic mutation when compared to the wild-type MphR gene sequence; and
ii. a reporter gene whose transcription is under the control of a promoter region which is regulated by the MphR transcription factor;
and
detecting the polyketide based on the differential expression of the reporter gene in comparison to a cell comprising a wild-type MphR gene sequence.

In one embodiment, the nucleic acid encoding the genetically modified MphR gene sequence and the reporter gene are located on one recombinant DNA vector.

In one embodiment, the reporter gene is a gene coding for chloramphenicol acetyltransferase, beta-galactosidase, luciferase or green fluorescent protein (GFP). In one embodiment, the reporter gene is a gene coding for green fluorescent protein (GFP).

In some embodiments, the MphR mutation confers improved sensitivity for detecting erythromycin A. In one embodiment, the MphR genetic mutation encodes a nucleotide change in the ribosome binding site sequence. In one embodiment, the MphR genetic mutation encodes a nucleotide change in the ribosome binding site sequence selected from A1G, A1T, A1C, G2T, G2A, A3C, A3G, A4T, G5T, G6T, or a combination thereof. In one embodiment, the MphR genetic mutation encodes a nucleotide change in the ribosome binding site sequence selected from A1G, A4T, or a combination thereof. In one embodiment, the MphR genetic mutation encodes an A1G nucleotide change in the ribosome binding site sequence. In one embodiment, the MphR genetic mutation encodes an A4T nucleotide change in the ribosome binding site sequence.

In one embodiment, the MphR genetic mutation encodes a nucleotide change in the ribosome binding site sequence selected from A1T, G2T, A3C, or a combination thereof. In one embodiment, the MphR genetic mutation encodes a nucleotide change in the ribosome binding site sequence selected from A1C, G2T, A3G, or a combination thereof. In one embodiment, the MphR genetic mutation encodes a nucleotide change in the ribosome binding site sequence selected from G2A, G5T, or a combination thereof.

In one embodiment, the MphR genetic mutation encodes the amino acid change selected from T17R, T27G, Q65M, T27A, M59E, M59S, R22H, K35N, T49I, L89V, D98N, E109D, R122T, K132N, A151T, H184Q, T49I, L89V, D98N, E109D, or a combination thereof. In one embodiment, the MphR genetic mutation encodes the amino acid change selected from T17R, T27G, Q65M, T27A, M59E, M59S, R22H, K35N, or a combination thereof. In one embodiment, the MphR genetic mutation encodes the amino acid change selected from T49I, L89V, D98N, E109D, R122T, K132N, A151T, H184Q, T49I, L89V, D98N, E109D, or a combination thereof.

In some embodiments, the MphR mutation confers improved selectivity for detecting erythromycin A in comparison to other polyketides. In one embodiment, the MphR genetic mutation encodes the amino acid change selected from A16T, T154M, M155K, or a combination thereof. In one embodiment, the MphR genetic mutation encodes an A4T nucleotide change in the ribosome binding site sequence and an amino acid change selected from A16T, T154M, M155K, or a combination thereof.

In some embodiments, the MphR mutation confers improved selectivity for detecting erythromycin A in comparison to structurally similar precursors. In one embodiment, the MphR genetic mutation encodes the amino acid change selected from P4L, W107L, H193R, or a combination thereof.

In some embodiments, the MphR mutation confers improved sensitivity for detecting pikromycin. In one embodiment, the MphR genetic mutation encodes the amino acid change S106F.

In some embodiments, the MphR mutation confers improved sensitivity for detecting narbomycin. In one embodiment, the MphR genetic mutation encodes the amino acid change selected from V33L, A34S, R51C, or a combination thereof.

In some embodiments, the MphR mutation confers improved sensitivity for detecting clarithromycin. In one embodiment, the MphR genetic mutation encodes the amino acid change selected from T49I, L89V, D98N, E109D or a combination thereof. In one embodiment, the MphR genetic mutation encodes the amino acid change R122T. In one embodiment, the MphR genetic mutation encodes the amino acid change selected from R122T, K132N, A151T, H184Q, or a combination thereof. In one embodiment, the MphR genetic mutation encodes an A4T nucleotide change in the ribosome binding site sequence and an amino acid change selected from R122T, K132N, A151T, H184Q, or a combination thereof. In one embodiment, the MphR genetic mutation encodes the amino acid change selected from T49I, L89V, D98N, E109D, or a combination thereof.

In one embodiment, the cell is *E. coli*. In one embodiment, the cell is *Streptomyces*. In one embodiment, the cell is *Streptomyces venezuelae*.

In one aspect, provided herein is a method of screening for genetic mutations in a target gene, comprising:
introducing into a cell:
i. a nucleic acid encoding a genetically modified MphR gene sequence, wherein the nucleic acid comprises at least one genetic mutation when compared to the wild-type MphR gene sequence; and
ii. a reporter gene whose transcription is under the control of a promoter region which is regulated by the MphR transcription factor;
introducing at least one mutation into a target gene; and
identifying a cell comprising the target gene mutation based on the differential expression of the reporter gene in comparison to a cell comprising the wild-type target gene.

In one embodiment, the reporter gene is a gene coding for chloramphenicol acetyltransferase, beta-galactosidase, luciferase or green fluorescent protein (GFP). In one embodiment, the reporter gene is a gene coding for green fluorescent protein (GFP).

In some embodiments, the MphR mutation confers improved sensitivity for detecting erythromycin A. In one embodiment, the MphR genetic mutation encodes a nucleotide change in the ribosome binding site sequence. In one embodiment, the MphR genetic mutation encodes a nucleotide change in the ribosome binding site sequence selected from A1G, A1T, A1C, G2T, G2A, A3C, A3G, A4T, G5T, G6T, or a combination thereof. In one embodiment, the MphR genetic mutation encodes a nucleotide change in the ribosome binding site sequence selected from A1G, A4T, or a combination thereof. In one embodiment, the MphR genetic mutation encodes an A1G nucleotide change in the ribosome binding site sequence. In one embodiment, the MphR genetic mutation encodes an A4T nucleotide change in the ribosome binding site sequence.

In one embodiment, the MphR genetic mutation encodes a nucleotide change in the ribosome binding site sequence selected from A1T, G2T, A3C, or a combination thereof. In one embodiment, the MphR genetic mutation encodes a nucleotide change in the ribosome binding site sequence selected from A1C, G2T, A3G, or a combination thereof. In one embodiment, the MphR genetic mutation encodes a nucleotide change in the ribosome binding site sequence selected from G2A, G5T, or a combination thereof.

In one embodiment, the MphR genetic mutation encodes the amino acid change selected from T17R, T27G, Q65M, T27A, M59E, M59S, R22H, K35N, T49I, L89V, D98N, E109D, R122T, K132N, A151T, H184Q, T49I, L89V, D98N, E109D, or a combination thereof. In one embodiment, the MphR genetic mutation encodes the amino acid change selected from T17R, T27G, Q65M, T27A, M59E, M59S, R22H, K35N, or a combination thereof. In one embodiment, the MphR genetic mutation encodes the amino acid change selected from T49I, L89V, D98N, E109D, R122T, K132N, A151T, H184Q, T49I, L89V, D98N, E109D, or a combination thereof.

In some embodiments, the MphR mutation confers improved selectivity for detecting erythromycin A in comparison to other polyketides. In one embodiment, the MphR genetic mutation encodes the amino acid change selected from A16T, T154M, M155K, or a combination thereof. In one embodiment, the MphR genetic mutation encodes an A4T nucleotide change in the ribosome binding site sequence and an amino acid change selected from A16T, T154M, M155K, or a combination thereof.

In some embodiments, the MphR mutation confers improved selectivity for detecting erythromycin A in comparison to structurally similar precursors. In one embodiment, the MphR genetic mutation encodes the amino acid change selected from P4L, W107L, H193R, or a combination thereof.

In some embodiments, the MphR mutation confers improved sensitivity for detecting pikromycin. In one embodiment, the MphR genetic mutation encodes the amino acid change S106F.

In some embodiments, the MphR mutation confers improved sensitivity for detecting narbomycin. In one embodiment, the MphR genetic mutation encodes the amino acid change selected from V33L, A34S, R51C, or a combination thereof.

In some embodiments, the MphR mutation confers improved sensitivity for detecting clarithromycin. In one embodiment, the MphR genetic mutation encodes the amino acid change selected from T49I, L89V, D98N, E109D or a combination thereof. In one embodiment, the MphR genetic mutation encodes the amino acid change R122T. In one embodiment, the MphR genetic mutation encodes the amino acid change selected from R122T, K132N, A151T, H184Q, or a combination thereof. In one embodiment, the MphR genetic mutation encodes an A4T nucleotide change in the ribosome binding site sequence and an amino acid change selected from R122T, K132N, A151T, H184Q, or a combination thereof. In one embodiment, the MphR genetic mutation encodes the amino acid change selected from T49I, L89V, D98N, E109D, or a combination thereof.

EXAMPLES

The following examples are set forth below to illustrate the systems, cells, methods, compositions and results according to the disclosed subject matter. These examples are not intended to be inclusive of all aspects of the subject matter disclosed herein, but rather to illustrate representative systems, cells, methods, compositions and results. These examples are not intended to exclude equivalents and variations of the present invention which are apparent to one skilled in the art.

Example 1

MphR Biosensors with Improved Sensitivity for Erythromycin A (ErA)

Figure 2A:
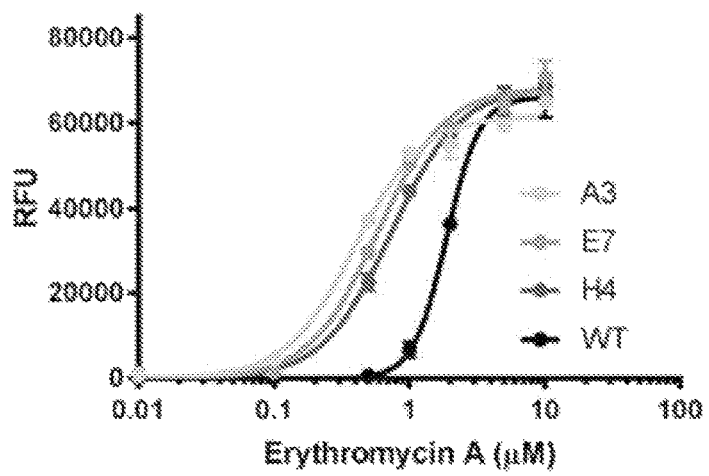
FIGS. 2A-2C. Engineered MphR variants with improved sensitivity towards erythromycin A (ErA) and sensitivity of amino acid changes compared to ribosome binding site mutations.
Figure 2B:
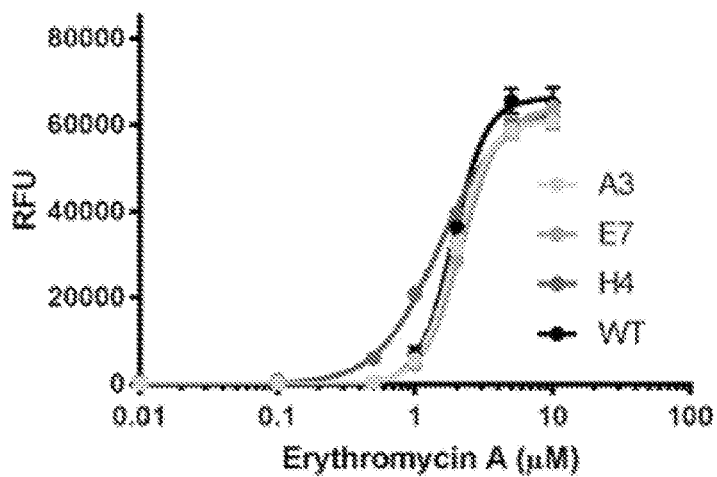
Figure 2C:
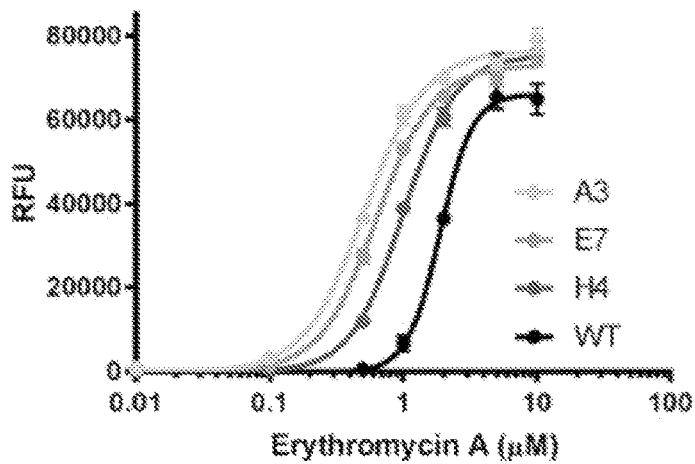

The sensitivity of biosensors often requires tailoring to meet specific needs. For example, if a certain polyketide is expected to be found inside microbial cells at concentrations between 0 and 100 µM, then a biosensor is required that displays a linear detection response within the same range. The wild-type MphR gene was subjected to a directed evolution approach in order to identify MphR gene mutations and variants with improved sensitivity towards ErA. A library of MphR gene mutations and variants was created by error-prone PCR (epPCR). Because many mutations could lead to misfolded MphR variants or those that do not bind to the operator, flow cytometry was first used to remove variants that are always 'ON' in the absence of ligand. Next, individual 'OFF' variants were tested in wells of microplates to identify the variants most improved at low concentrations of ErA. Next, using promising individual variants, GFP fluorescence was measured in the presence of varying concentrations of erythromycin A (ErA) and the data was fit to the Hill equation to provide several parameters for describing selected MphR variants: dynamic range ($GFP_{max}$-$GFP_{min}$), $K_{1/2}$ (ligand conc. resulting in half-maximal induction), cooperativity (Hill coefficient), linear range of detection, and Z'-factor (score of 0.50 indicates an excellent screen). Three variants (H4, A3, and E7) displayed improvements in sensitivity (FIG. 2 and Table 9).

Additional mutations in the MphR gene sequence that provided increased sensitivity to erythromycin A (ErA) were also identified. The MphR macrolide resistance cassette operates as an analog converter of macrolide concentration to antibiotic resistance, as explained above and elsewhere ((Noguchi N, et al. Regulation of Transcription of the mph(A) Gene for Macrolide 2'-Phosphotransferase I in *Escherichia Coli*; Characterization of the Regulatory Gene mphR(A). *Journal of Bacteriology.* 2000; 182(18):5052-5058) (Zheng J, et al. Structure and Function of the Macrolide Biosensor Protein, MphR(A), With and Without Erythromycin. *Journal of Molecular Biology.* 2009; 387(5): 1250-60). Refactoring the MphR cassette as a two plasmid system with a GFP reporter (Gardner L, et al. Photochemical Control of Bacterial Signal Processing Using a Light-activated Erythromycin. *Molecular Biosystems.* 2011; 7(9):

2554-7) created a biosensor capable of detecting a range of macrolides. Previous literature reports various induction ranges for MphR-based biosensors depending on the plasmid construct. Church and coworkers reported $K_{1/2}$ values of 22 and 97 µM erythromycin A for low and high copy number plasmids respectively, using a GFP reporter (Rogers, J. et al. 7648-7660 Nucleic Acids Research, 2015, Vol. 43, No. 15). Eberz and coworkers report an apparent induction range of 0 (min luminescence) to 20 (max luminescence) µM erythromycin A with an approximate half maximal induction at 10 µM using the LuxABCDE luminescence reporter system (Mohrle, V. et al. Anal. Bioanal. Chem. 2007 July; 388(5-6):1117-25). In the experiments conducted herein, a previously reported MphR-based biosensor (MphR-WT) (Gardner L, et al. Photochemical Control of Bacterial Signal Processing Using a Light-activated Erythromycin. *Molecular Biosystems*. 2011; 7(9):2554-7) had a $K_{1/2}$ of only 2.73 µM erythromycin A (Table 1) using a GFP reporter. Error-prone and multi-site saturation mutagenesis of the MphR gene was performed in order to improve sensitivity to erythromycin A.

Figure 15:
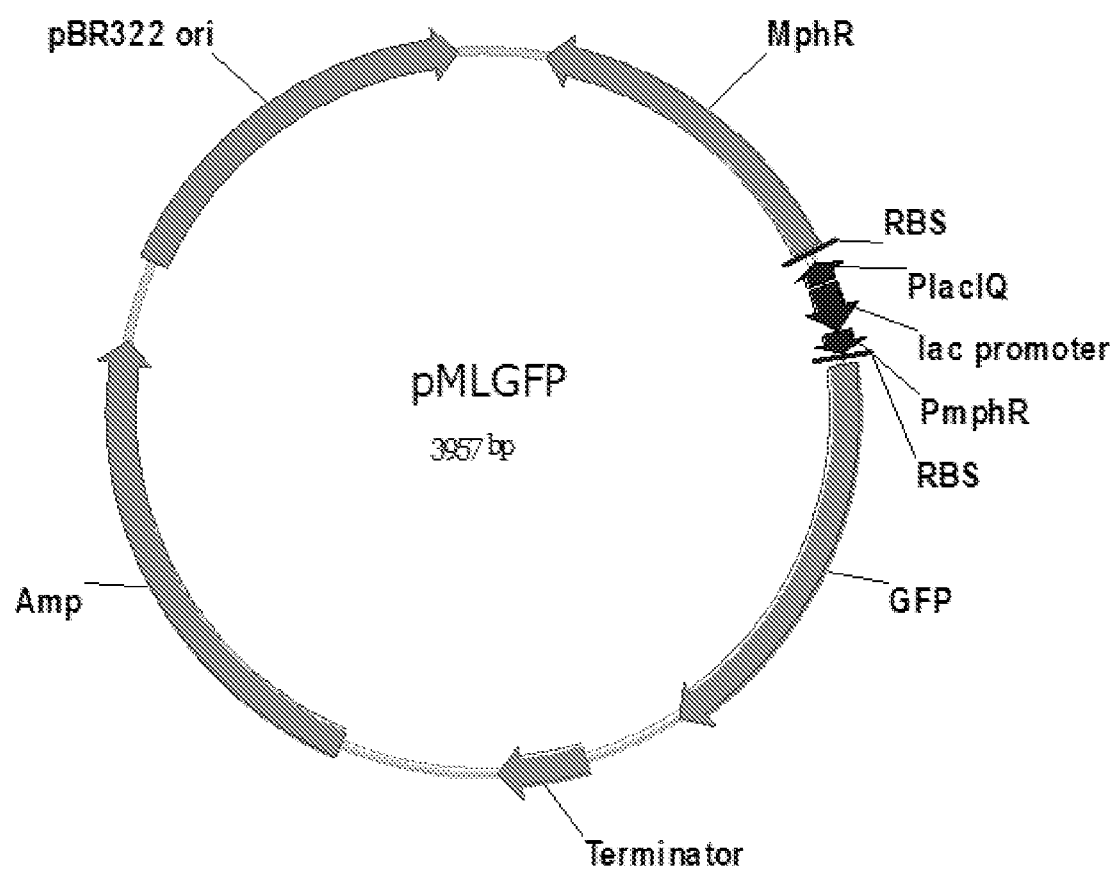
FIG. 15. Plasmid map for pMLGFP.
Figure 16:
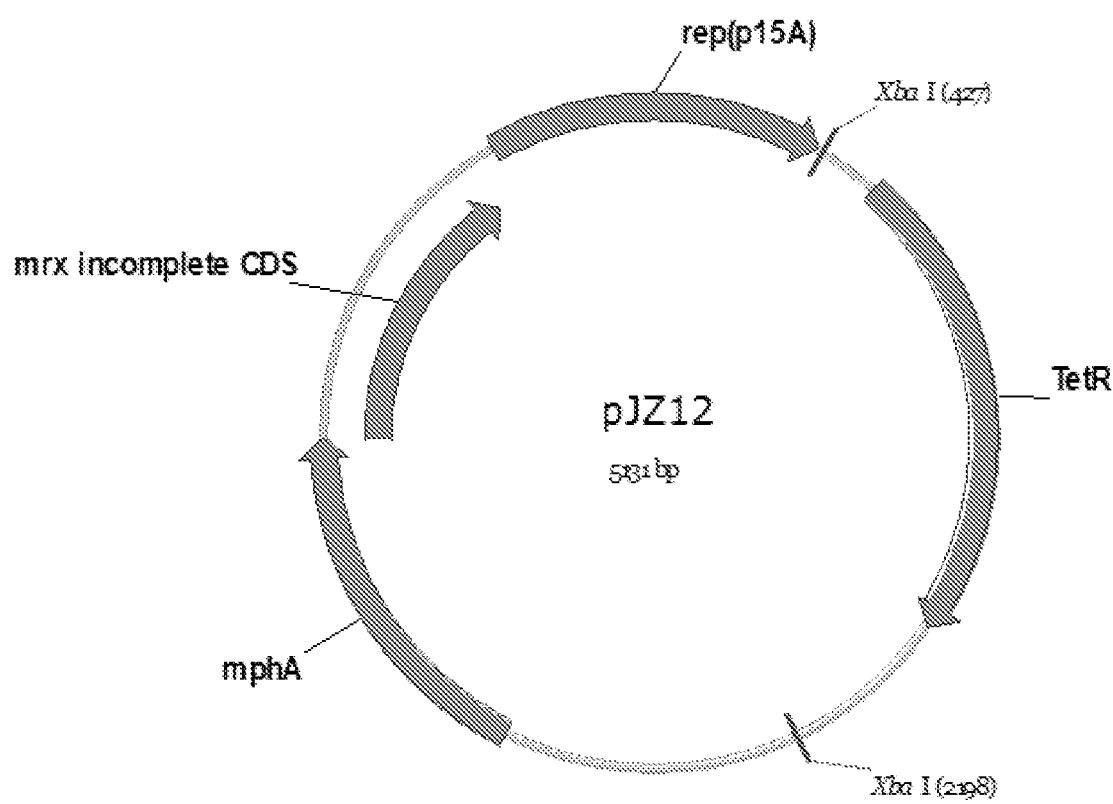
FIG. 16. Plasmid map for pJZ12.

Plasmid pMLGFP (See FIG. 15 and sequence below) (Gardner L, et al. Photochemical Control of Bacterial Signal Processing Using a Light-activated Erythromycin. *Molecular Biosystems*. 2011; 7(9):2554-7) containing the MphR gene was utilized to make mutants of the MphR protein. Three and five site saturation mutagenesis libraries of the MphR gene that targeted residues of the ligand binding domain were generated using the Quikchange Multi Site-Directed mutagenesis kit (Agilent) and designated QCMS3 and QCMS5, respectively. A third library was generated via error-prone PCR (epPCR) with an average of two amino acid mutations per library clone. Libraries were transformed into *E. coli* TOP10 cells with plasmid pJZ12 (See FIG. 16 and sequence below) containing genes MphA and mrx and subjected to an initial round of negative sorting in the absence of added ligand via Fluorescence Activated Cell Sorting (FACS) to eliminate variants that are constitutively expressing GFP. Pools of negatively-selected mutants were then plated on LB-agar plates and individual colonies were screened in 96-well microtiter plates in the presence of no ligand and 1 uM erythromycin A. Several clones showed initial improvements in erythromycin A sensitivity versus MphR-WT.

Figure 11A:
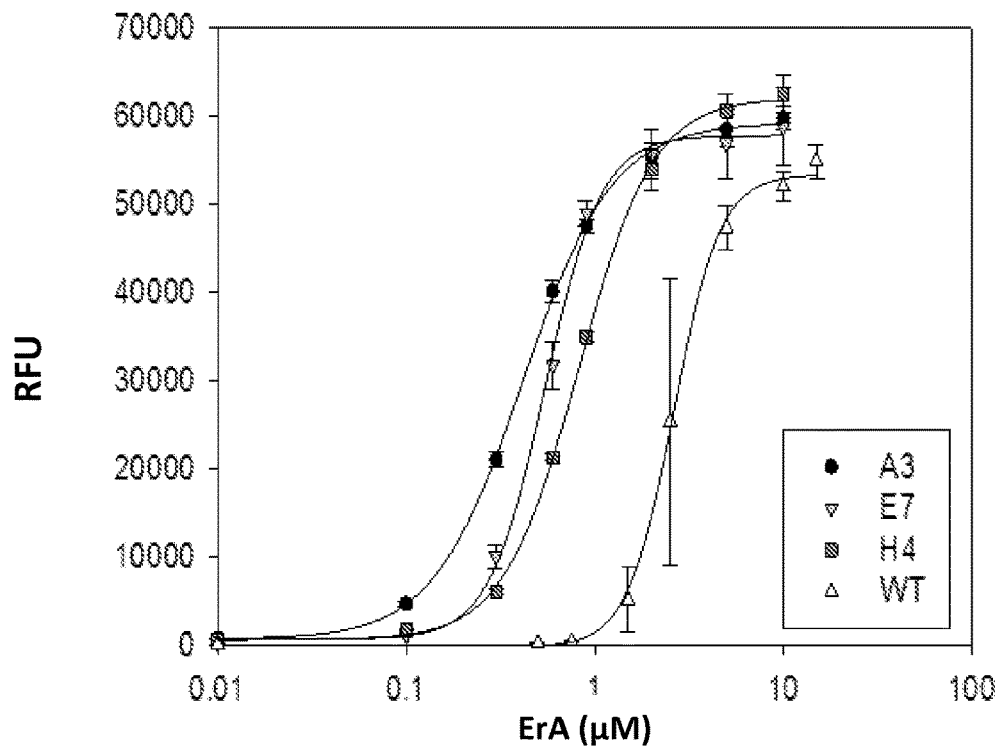
FIGS. 11A-11B. Dose-response curves of several selected clones compared to the wild-type biosensor. Multiple MphR mutants displayed increased sensitivity to erythromycin A versus MphR-WT. Clones generated by error prone PCR (epPCR) (FIG. 11A) typically performed better than clones generated by multi-site mutagenesis (FIG. 11B).
Figure 11B:
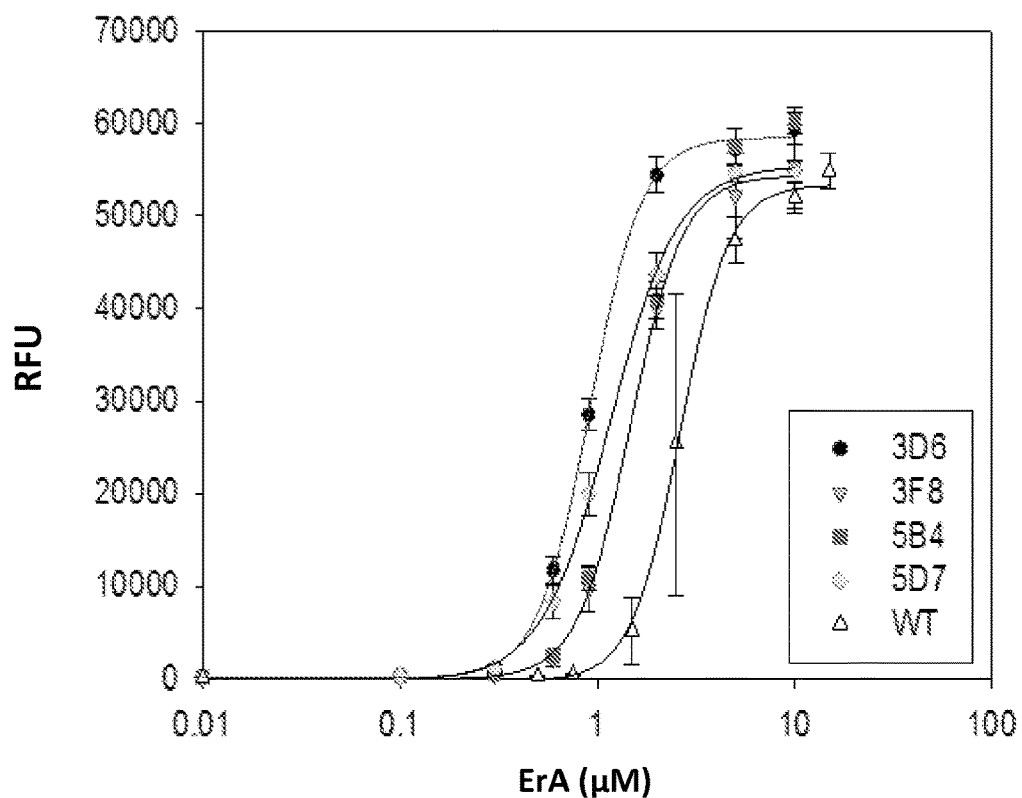

The best performing clones from each library were selected for further analysis. Dose-response experiments revealed clones with improved performance features compared to MphR-WT for erythromycin A sensitivity (FIG. 11 (A-B) and Table 1.) The QCMS3, QCMS5, and epPCR libraries all yielded clones with higher sensitivity to low concentrations of erythromycin A, with the greatest results coming from the epPCR library. Clone MphR-G76C, containing the mutation G76C in the MphR protein, showed a sensitivity increase that shifted its linear range of detection into nanomolar concentrations, approaching an order of magnitude sensitivity increase versus MphR-WT.

TABLE 1

Biosensor Performance Features for MphR Mutations.

| Clone | $K_{1/2}$ (µm) | Cooperativity | dynamic range ($GFP_{max}$-$GFP_{min}$) | linear range of detection (µM) |
|---|---|---|---|---|
| G76C | 0.42 ± 0.01 | 1.80 ± 0.01 | 59000 | 0.1-0.6 |
| V90I | 0.55 ± 0.01 | 2.84 ± 0.42 | 58600 | 0.1-1 |
| T17R | 0.93 ± 0.03 | 3.16 ± 0.13 | 59300 | 0.3-1 |

TABLE 1-continued

Biosensor Performance Features for MphR Mutations.

| Clone | $K_{1/2}$ (µm) | Cooperativity | dynamic range ($GFP_{max}$-$GFP_{min}$) | linear range of detection (µM) |
|---|---|---|---|---|
| T27G/Q65M | 1.55 ± 0.09 | 2.92 ± 0.17 | 60200 | 0.6-2 |
| T27A/M59E | 1.15 ± 0.09 | 2.59 ± 0.04 | 54800 | 0.1-2 |
| WT | 2.73 ± 0.72 | 4.44 ± 1.52 | 54800 | 0.9-5 |

In Table 1, Hill functions were used to derive biosensor transfer functions. $K_{1/2}$ is the inducer concentration at half maximal induction. Cooperativity is derived from the Hill function to indicate cooperative ligand binding between protein monomers of the MphR dimer. Dynamic range is the GFP maximal response minus the minimum GFP response, which in all cases was the response with no ligand. The linear range of detection is the linear portion of the dose-response curve with a slope $R^2$=0.95 or higher.

Importantly, several of these sensors have linear detection ranges capable of detecting titers of erythromycin A heterologously produced in shake-flask *E. coli* cultures. As this has remained a preferred method for the production of erythromycin A and erythromycin A derivatives resulting from precursor-directed mutasynthesis (Sundermann U, et al. Enzyme-directed Mutasynthesis: a Combined Experimental and Theoretical Approach to Substrate Recognition of a Polyketide Synthase. *ACS Chemical Biology*. 2013; 8(2):443-50) or domain-swapping biosynthesis (Jiang M., Pfeifer, B. Metabolic and Pathway Engineering to Influence Native and Altered Erythromycin Production Through *E. coli*. *Metabolic Engineering*. 2013; 19:42-9), MphR biosensors can be used in high-throughput approaches to the continued improvement of heterologous erythromycin A biosynthetic engineering.

After further analysis of these clones, via DNA sequencing, the ribosome binding site (RBS) of A3 and E7 were found to be mutated, compared to the wild-type MphR sequence. Clone H4 also had mutations in other portions of the sequence and thus was omitted from further analysis here. This implicates the RBS mutations in these variants are responsible for sensitivity to erythromycin, rather than the amino acid changes identified. To confirm this, new versions of A3 and E7 were constructed that either only included the RBS mutations or the amino acids for each clone. Subsequent analysis revealed that the RBS mutations alone were responsible for the improvement in sensitivity to erythromycin (FIG. 2; Tables 2 and 3).

TABLE 2

Sensitivity of wild-type MphR and ribosome binding site (RBS)-only mutations towards erythromycin A

|  | WT | WT A3-RBS | WT E7-RBS |
|---|---|---|---|
| $K_{1/2}$ (µM) | 1.9 ± 0.03 | 0.52 ± 0.02 | 0.64 ± 0.02 |

TABLE 3

Sensitivity of wild-type MphR and amino-acid change-only mutations towards erythromycin A

|  | WT-AA | A3-AA | E7-AA |
|---|---|---|---|
| $K_{1/2}$ (µM) | 1.9 ± 0.03 | 1.9 ± 0.02 | 2.2 ± 0.03 |

Example 2

Figure 17:
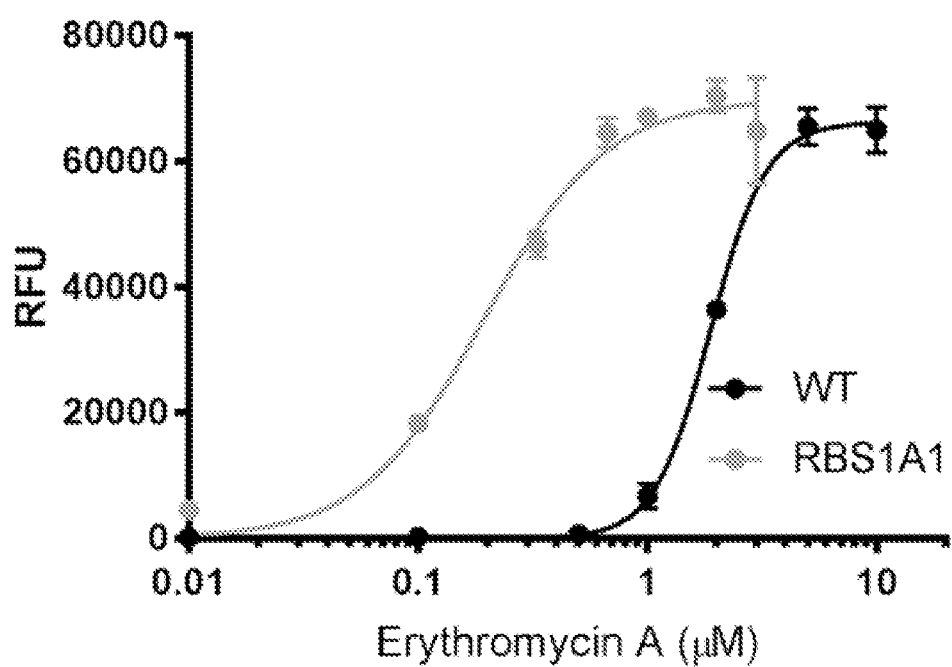
FIG. 17. Sensitivity of the smRBS1A1 clone versus the wild-type (WT) biosensor with erythromycin A.
Figure 18:
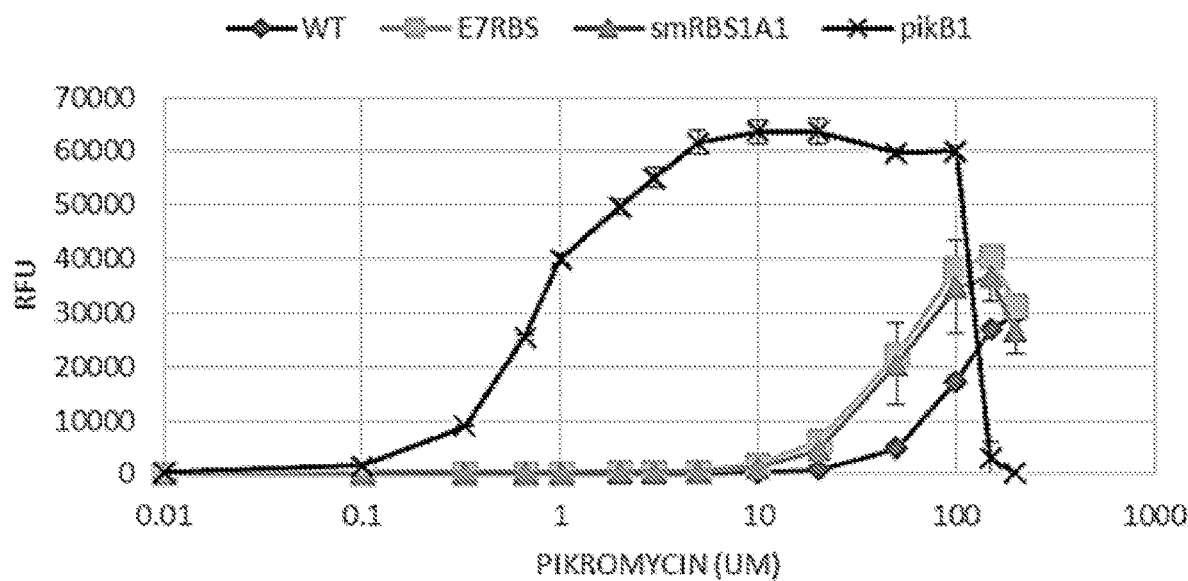
FIG. 18. Sensitivity of clones E7-RBS, smRBS1A1, pikB1, and wild-type (WT) with pikromycin.
Figure 19A:
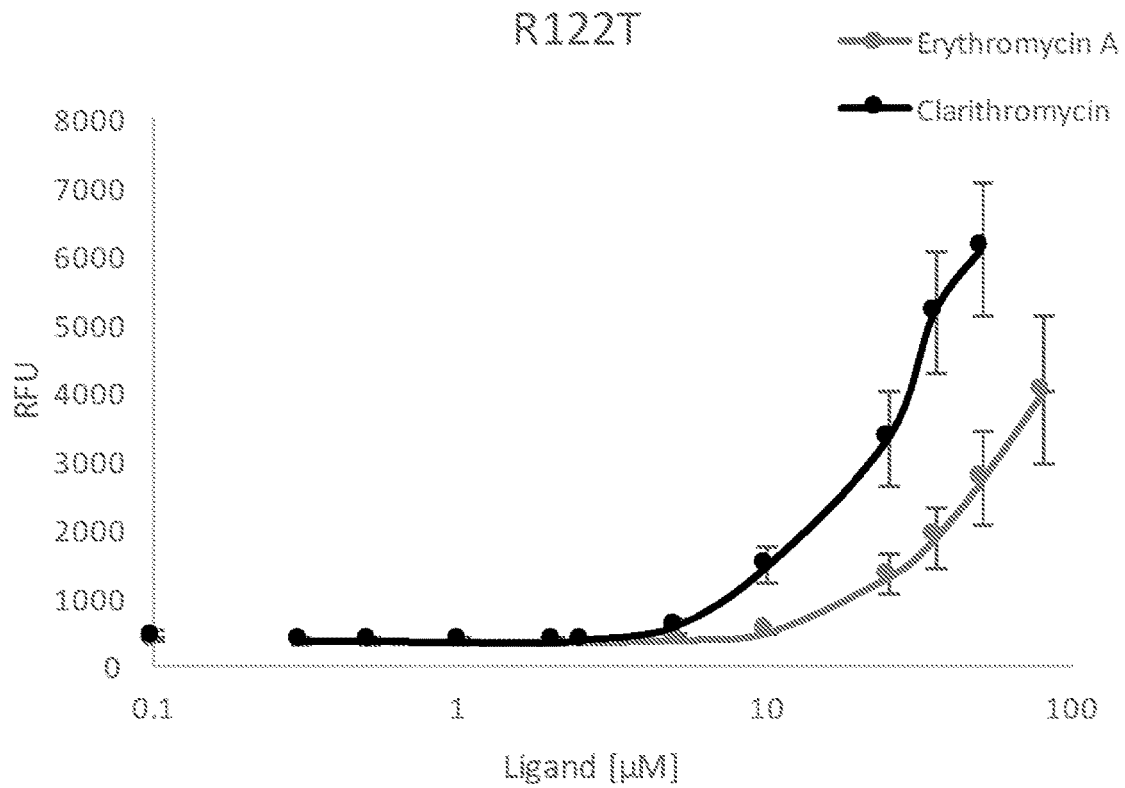
FIG. 19A. Clarithromycin/erythromycin A selectivity with R122T MphR.
Figure 19B:
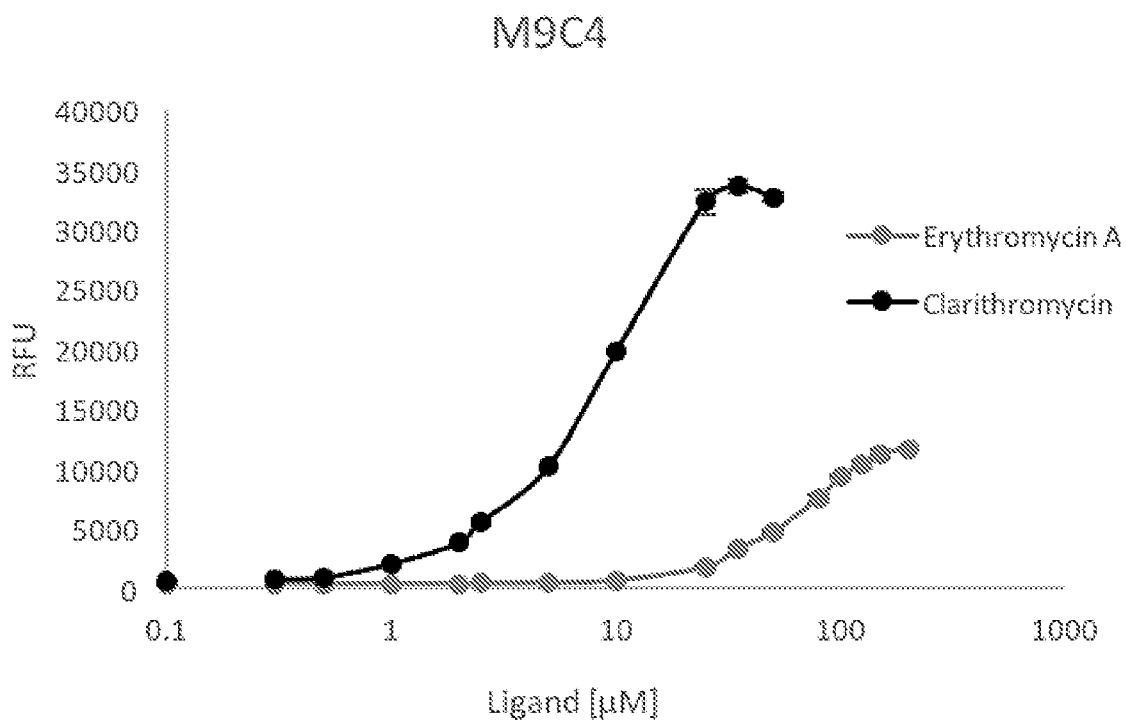
FIG. 19B. Clarithromycin/erythromycin A selectivity with the M9C4 clone.
Figure 19C:
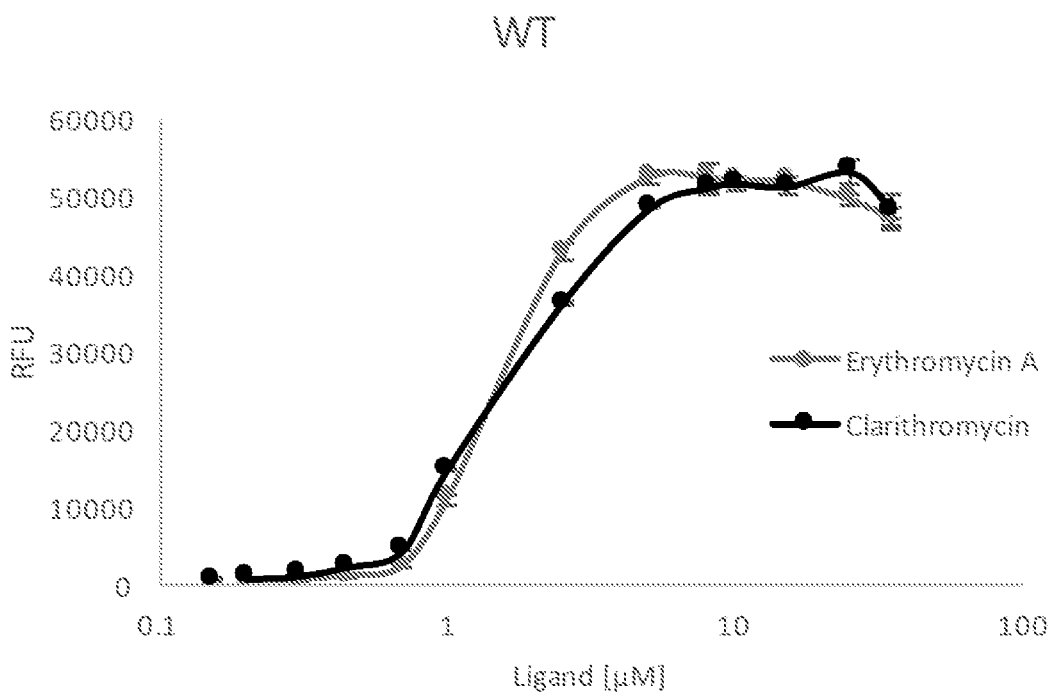
FIG. 19C. Clarithromycin/erythromycin A selectivity with wild-type (WT) MphR.
Figure 19D:
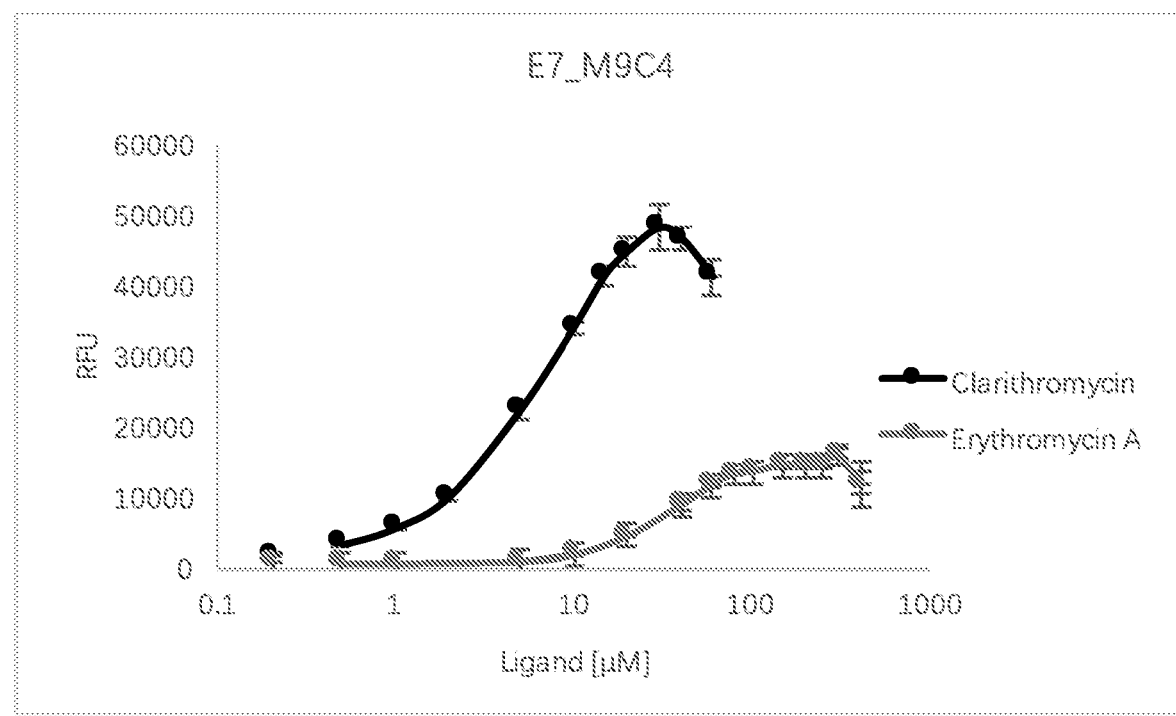
FIG. 19D. Clarithromycin/erythromycin A selectivity with the E7-M9C4 clone.
Figure 20:
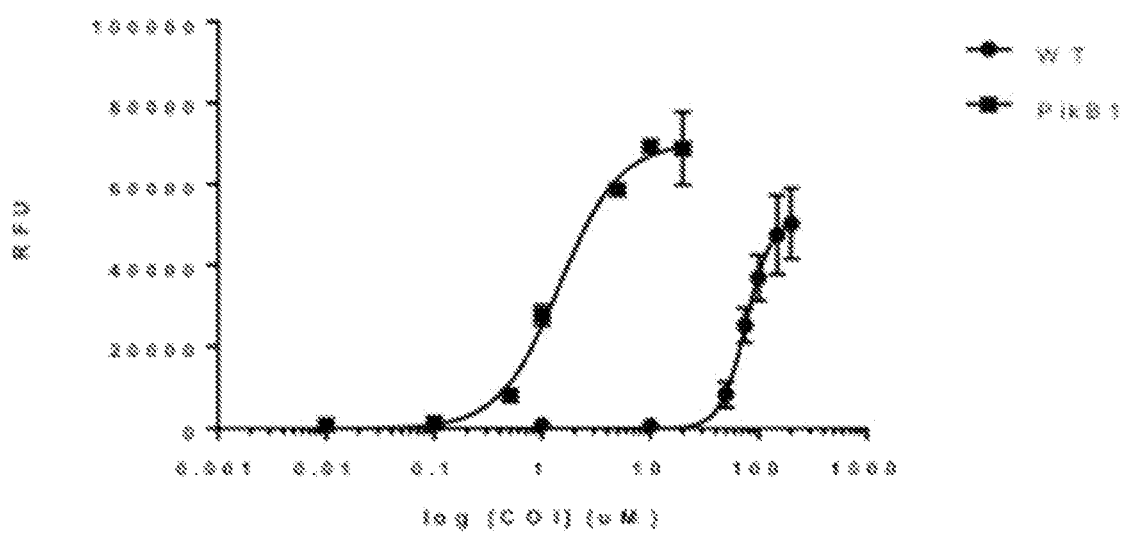
FIG. 20. MphR clone "PikB1" can detect a solithromycin biosynthetic intermediate.

Engineering Sensitivity Towards Erythromycin Via Ribosome Binding Site (RBS) Mutagenesis of MphR The finding that mutations to the ribosome binding site (RBS) of clones A3 and E7 were responsible for modulating sensitivity prompted the inventors to make a dedicated library of RBS mutations to search for biosensors with improved sensitivities. Screening the "smRBS" library and analysis of the best performing clones revealed three clones (see below) with significantly improved sensitivity towards erythromycin. The best clone, smRBSA1, outperforms each mutant previously described (FIG. 17; Table 4). In addition, the sensitivity of smRBSA1 towards pikromycin was improved 2-fold, compared to the wild-type MphR. Thus, the RBS mutations discovered by screening against erythromycin can impact sensitivity towards other polyketides (FIG. 18; Table 5).

TABLE 4

Sensitivity of smRBS mutants with erythromycin A.

| Clone | RBS | $K_{1/2}$ (μm) | DR (GFP) | LRD (μM) | $Hill_c$ |
|---|---|---|---|---|---|
| MphR-WT | AGAAGGT | 1.88 ± 0.03 | 66000 | 0.9-5 | 3.6 ± 0.3 |
| smRBS1A1 | TTCAGGT | 0.19 ± 0.02 | 66000 | 0.01-0.7 | 1.7 ± 0.1 |
| smRBS1G6 | CTGAGGT | 0.91 ± 0.04 | 64000 | 0.3-2 | 5.4 ± 1.2 |
| smRBS2E1 | AAAGGTT | 1.44 ± 0.08 | 63000 | 0.3-3 | 3.9 ± 0.5 |

'DR' is the dynamic range, $GFP_{max}$-$GFP_{min}$;
'LRD' is the linear range of detection.

TABLE 5

E7-RBS, smRBS1A1, pikB1, and WT with pikromycin

| Clone | $K_{1/2}$ (μm) | $Hill_C$ | Dyn. Range (RFU) |
|---|---|---|---|
| WT | 97 ± 2 | 2.9 ± 0.3 | 26800 ± 400 |
| E7-RBS | 50 ± 20 | 2.3 ± 0.1 | 40000 ± 5000 |
| smRBS1A1 | 48 ± 5 | 2.5 ± 0.2 | 37000 ± 6000 |
| pikB1 | 0.81 ± 0.02 | 1.8 ± 0.2 | 64000 ± 2000 |

Example 3

MphR Biosensors with Improved Selectivity Towards ErA

Figure 3B:
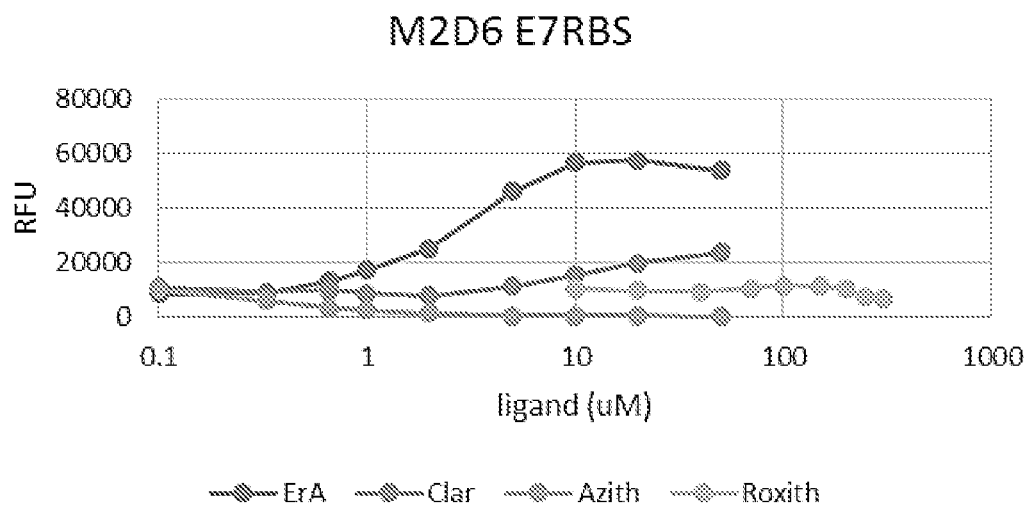
FIG. 3B. Erythromycin, clarithromycin, azithromycin, roxithromycin sensitivity with M2D6-E7RBS MphR.
Figure 3C:
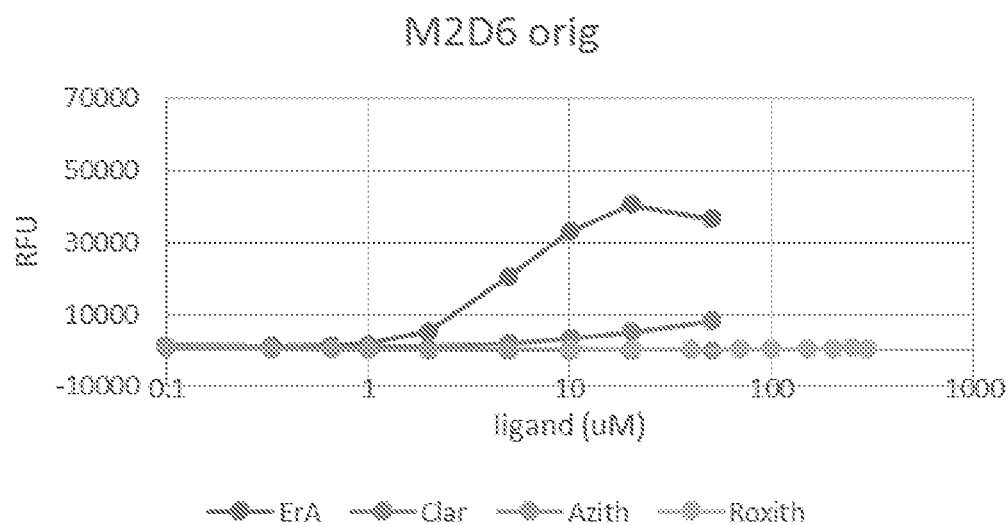
FIG. 3C. Erythromycin, clarithromycin, azithromycin, roxithromycin sensitivity with M2D6 MphR.

In many cases, it is necessary to determine the presence and concentration of a given polyketide in the presence of other structurally related molecules. Accordingly, the selectivity of MphR requires tailoring towards target molecules. To test the capacity of random mutations to alter the ligand specificity of MphR, the initial goal was to find variants that were more selective with erythromycin A compared to clarithromycin, azithromycin, and roxithromycin. A library of MphR gene mutations and variants was created by error-prone PCR (epPCR) and flow cytometry was first used to remove variants that are always 'ON' in the absence of erythromycin A and the presence of clarithromycin and azithromycin. Next, individual 'OFF' variants were tested in wells of microplates to identify the variants most improved at low concentrations of erythromycin A. Thus, some of the 'OFF' library members were duplicated and each screened in the presence of erythromycin A or a mixture of clarithromycin, azithromycin, and roxithromycin. Several variants were not activated by clarithromycin, azithromycin, and roxithromycin but were strongly activated by erythromycin A (FIG. 3). One variant, M2D6, was chosen for quantitative analysis, which confirmed that the ligand specificity of this variant was very different from that of the WT MphR (FIG. 3 and Table 11).

To confirm previous reports of the broad inducer tolerance of the MphR biosensor (Eberz 2007), erythromycin A and several clinically useful semi-synthetic macrolides were screened versus MphR-WT. In liquid culture, dose-dependent MphR-WT activations for erythromycin A (compound 1), clarithromycin (compound 2), azithromycin (compound 3), and roxithromycin (compound 4) were obtained (FIG. 12) and the induction parameters with each compound were compared (Table 6).

Clarithromycin is an erythromycin A semi-synthetic analog that differs by a single methoxy in place of a hydroxyl group at the C-6 carbon of the polyketide core macrolactone. Azithromycin is an erythromycin analog synthesized by an oxime-mediated nitrogen insertion and ring expansion at C-9 of the polyketide backbone. Roxithromycin replaces the C-9 ketone of erythromycin A with an imine-linked polyester. Clarithromycin, azithromycin and roxithromycin are semi-synthetic products of microbially produced erythromycin A. Distinction between erythromycin A and these modified analogs has thus far relied on inherently low-throughput techniques such as LC-MS, HPLC and NMR.

Biosensors capable of selective detection of specific macrolides from laboratory, industrial or environmental samples are useful in improving biotransformations, increasing final titers by detecting biosynthetic bottlenecks, and identifying macrolide contaminants.

Figure 12A:
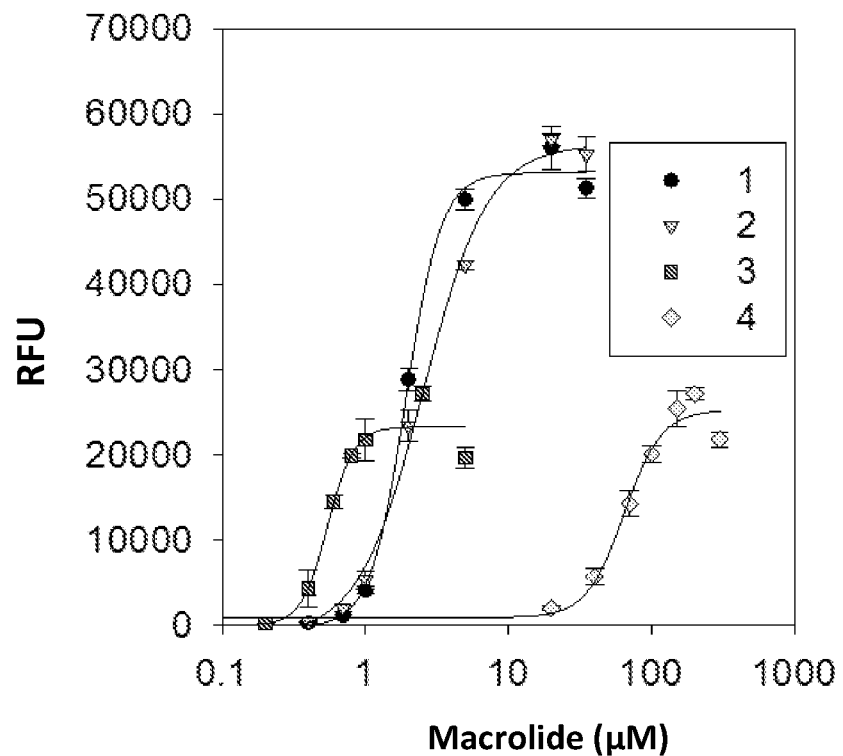
FIGS. 12A-12C. Dose-response curves of MphR-A16T/T154M/M155K compared to the wild-type biosensor induced by erythromycin A, clarithromycin, azithromycin and roxithromycin.
Figure 12B:
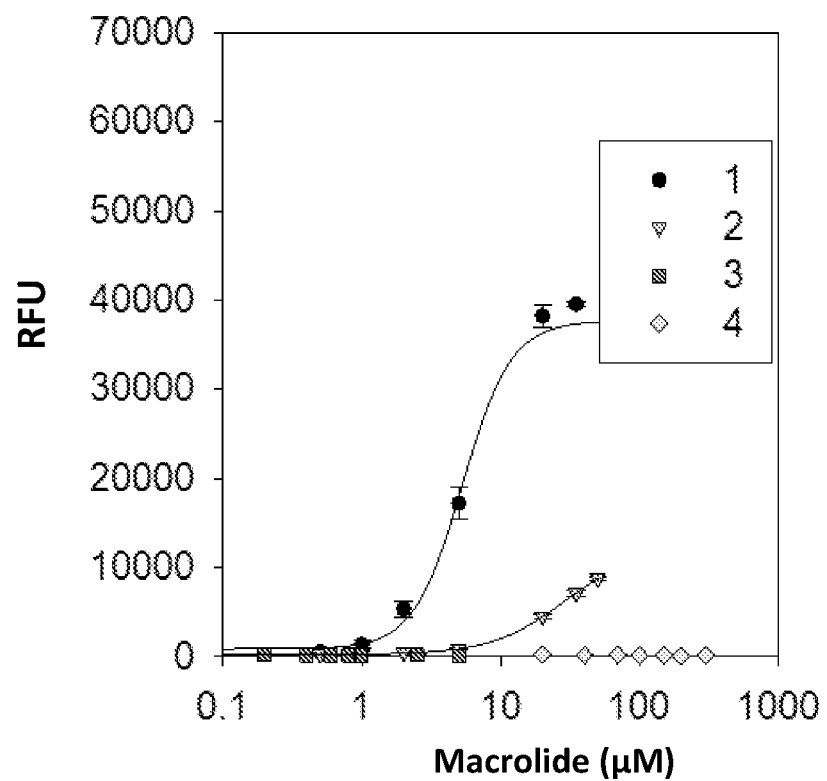
Figure 12C:
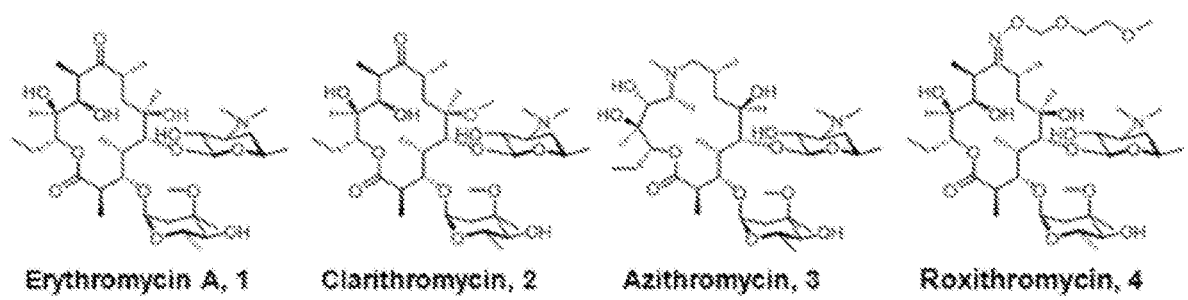

Clone MphR-A16T/T154M/M155K (Clone M2D6) demonstrated exceptional selectivity for erythromycin A versus the three semi-synthetic analogs. Dose-response analysis revealed MphR-A16T/T154M/M155K maintained a $K_{1/2}$ of 5.54 μM for erythromycin A, but displayed little to no activation by clarithromycin, azithromycin and roxithromycin. As summarized in Table 6 and FIG. 12, compared to MphR-WT, MphR-A16T/T154M/M155K proved to be a much more selective biosensor than its wild-type counterpart with the compounds tested.

TABLE 6

$K_{1/2}$ values of MphR-WT and MphR- A16T/T154M/M155K with erythromycin A, clarithromycin, azithromycin and roxithromycin.

| $K_{1/2}$ | 1 | 2 | 3 | 4 |
|---|---|---|---|---|
| WT | 2.03 ± 0.10 | 2.69 ± 0.14 | 0.60 ± 0.02 | 67.16 ± 3.41 |
| A16T/T154M/M155K | 5.54 ± 0.53 | 20.10 ± 0.28 | N.C. | N.C. |

In Table 6, Compounds are numbered above their corresponding $K_{1/2}$ value of each numbered compound (erythromycin A (1), clarithromycin (2), azithromycin (3) and roxithromycin(4)). MphR-A16T/T154M/M155K demonstrated much higher selectivity for erythromycin A versus its semi-synthetic counterparts compared to the wild-type biosensor.

MphR-A16T/T154M/M155K's ability to discriminate between closely related compounds that structurally differ by as little as a methyl substituent demonstrate the powerful application mutagenesis and high-throughput screen (HTS) have on developing tailored biosensors. Biosensors with specific ligand activation selectivities as demonstrated here are useful tools for monitoring reaction conversions in the production of erythromycin A analogs and in screening environmental samples for specific macrolide contaminants.

The RBS mutations from the erythromycin sensitive variant E7 were transferred to the MphR variant M2D6, which was previously engineering to be specific for erythromycin A. This new variant MphR M2D6-E7RBS displayed 2-fold enhanced sensitivity towards erythromycin A, but with negligible change in sensitivity towards semi-synthetic derivatives (analogues) (FIG. 3; Table 7).

TABLE 7

E7RBS-M2D6 compared to WT and M2D6

| Erythromycin (ErA) | $K_{1/2}$ (μM) | Dynamic range | Selectivity ($K_{1/2}$ErA/$K_{1/2}$analogue) |
|---|---|---|---|
| WT | 1.98 | 67000 | — |
| M2D6 | 4.84 | 39000 | — |
| M2D6-E7RBS | 2.63 | 49000 | — |

| | $K_{1/2}$ (μM) | Dynamic range | Selectivity |
|---|---|---|---|
| Clarithromycin | | | |
| WT | 2.00 | 64000 | 0.99 |
| M2D6 | 21.51 | 7000 | 0.23 |
| M2D6-E7RBS | 12.67 | 16000 | 0.21 |
| Azithromycin | | | |
| WT | 0.60 | 28000 | N.C. |
| M2D6 | N.C. | 0 | N.C. |
| M2D6-E7RBS | N.C. | 0 | N.C. |
| Roxithromycin | | | |
| WT | 74.08 | 32000 | N.C. |
| M2D6 | N.C. | 0 | N.C. |
| M2D6-E7RBS | N.C. | 0 | N.C. |

Example 4

Biosensors for Detection of Macrolide Glycosylation

Figure 4A:
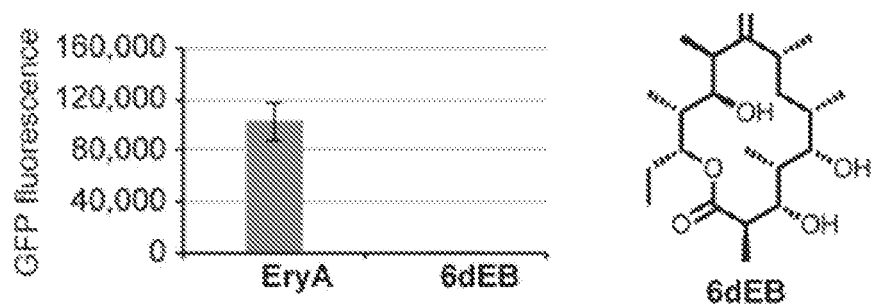
FIGS. 4A-4C. MphR is a robust macrolide glycosylation sensor.
Figure 4B:
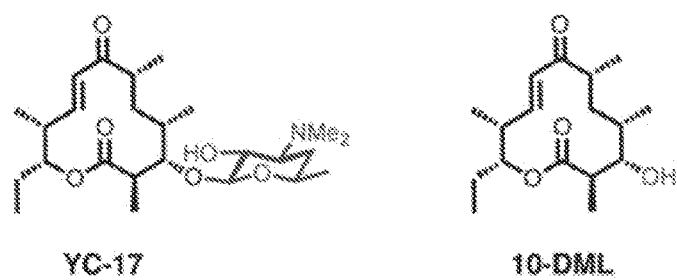
Figure 4C:
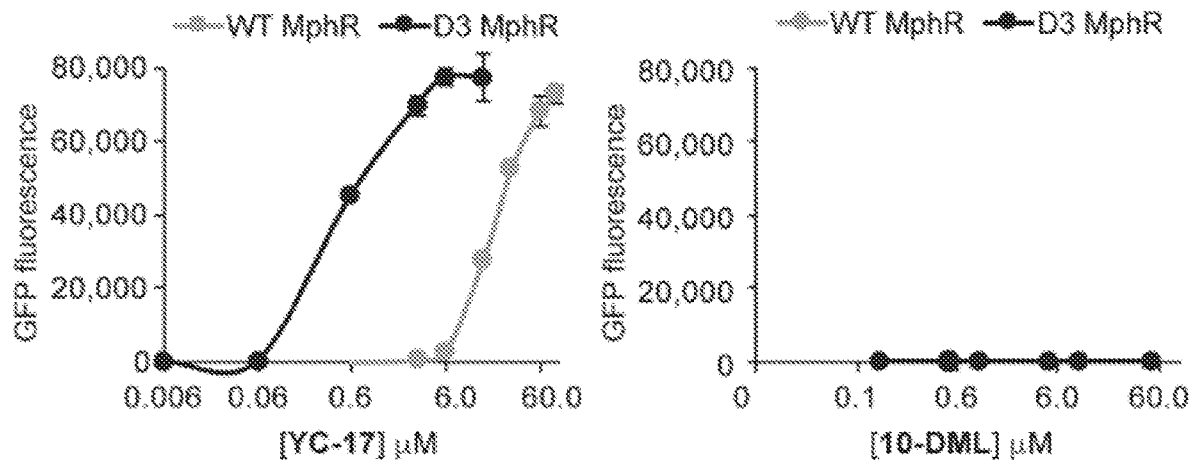

The ability for MphR or MphR gene variants thereof to discriminate between closely related polyketides provides opportunities to report the activity of enzymes which catalyze the transformation of a polyketide not detected by MphR into a product that is detected by MphR. For example, MphR may specifically recognize the sugar residues attached to detected polyketides. Thus, MphR likely does not detect the corresponding aglycones. To test this, the aglycone 6-deoxyerythronolide B (6dEB) was produced via an engineered *E. coli* strain and purified by flash chromatography. The identity of the compound was confirmed by comparison of the $^{13}C/^1H$-NMR spectral data to that published, by high-resolution mass analysis (6 dEB calc. [M+Na]+ m/z=409.25664; 6dEB obs. [M+Na]+ m/z=409.25525), and by comparison to authentic biosynthetic and synthetic standards. Next, the ability of 6 dEB to activate GFP expression under control of WT MphR was tested. As predicted, the aglycone failed to activate GFP expression, whereas the corresponding glycoside erythromycin A is a good activator (FIG. 4). To extend this to other systems, the ability of MphR was examined to detect macrolide antibiotics from *S. venezuelae*. The mono-glycosylated 12-membered macrolide YC-17 was detected by WT MphR whereas its corresponding aglycone (10-deoxymethynolide, 10-DML) was not (FIG. 4). Because the only structural difference between YC-17 and 10-DML is the desosamine sugar, this data confirms the ability of MphR to report macrolactone glycosylation. MphR libraries were also screened in the presence of YC-17 to identify variants that could detect the macrolide at lower concentrations than WT MphR. Indeed, one particular mutant detected YC-17 at concentrations up to 100-fold lower than that of the WT MphR while maintaining the same dynamic range as the WT sensor (FIG. 4). Whereas the desosamine moiety is likely a specificity-conferring factor for MphR, it is clear that directed evolution can be used to alter the ligand specificity of MphR towards otherwise poorly detected macrolides. These methods can be used for directed evolution to expand the recognition capabilities of MphR towards other sugar residues.

Example 5

Expanding the Synthetic Scope of Polyketide Glycosylation Machinery by Directed Evolution The stringent substrate specificity of natural product glycosyltransferases (GTs) severely restricts the scope of polyketide glycodiversification strategies. Directed evolution is used to expand the specificity of macrolide GTs. The specificity of MphR towards desosaminylated macrolides can be leveraged as a sensor to report glycosylation and identify GT variants with improved activity and substrate specificity. Libraries of GT variants can be challenged with diverse substrates and screening via the MphR biosensor. By testing the function of many GT variants using MphR, potentially any GT can be engineered. These described methods can produce variant GTs with broad specificities beyond those originally screened for, the creation of new tools for glycoside synthesis and a new approach for engineering natural product GTs.

Figure 10A:
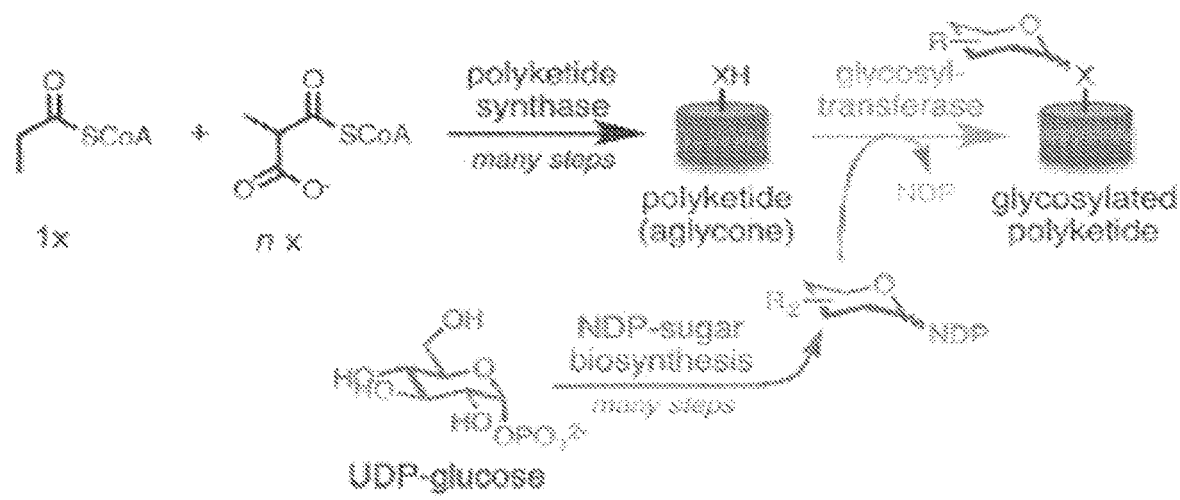
FIGS. 10A-10D. Glycosylation pathways and combinatorial biosynthesis.
Figure 10B:
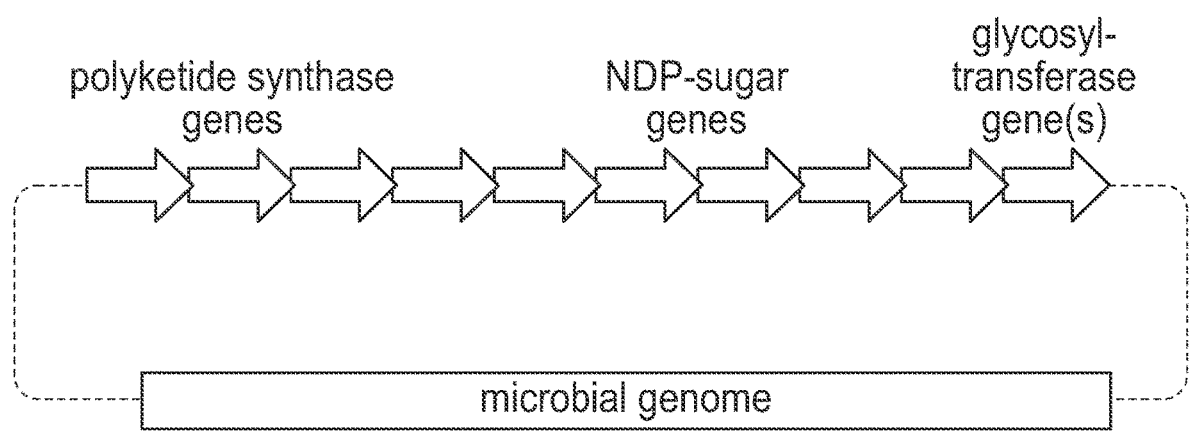
Figure 10C:
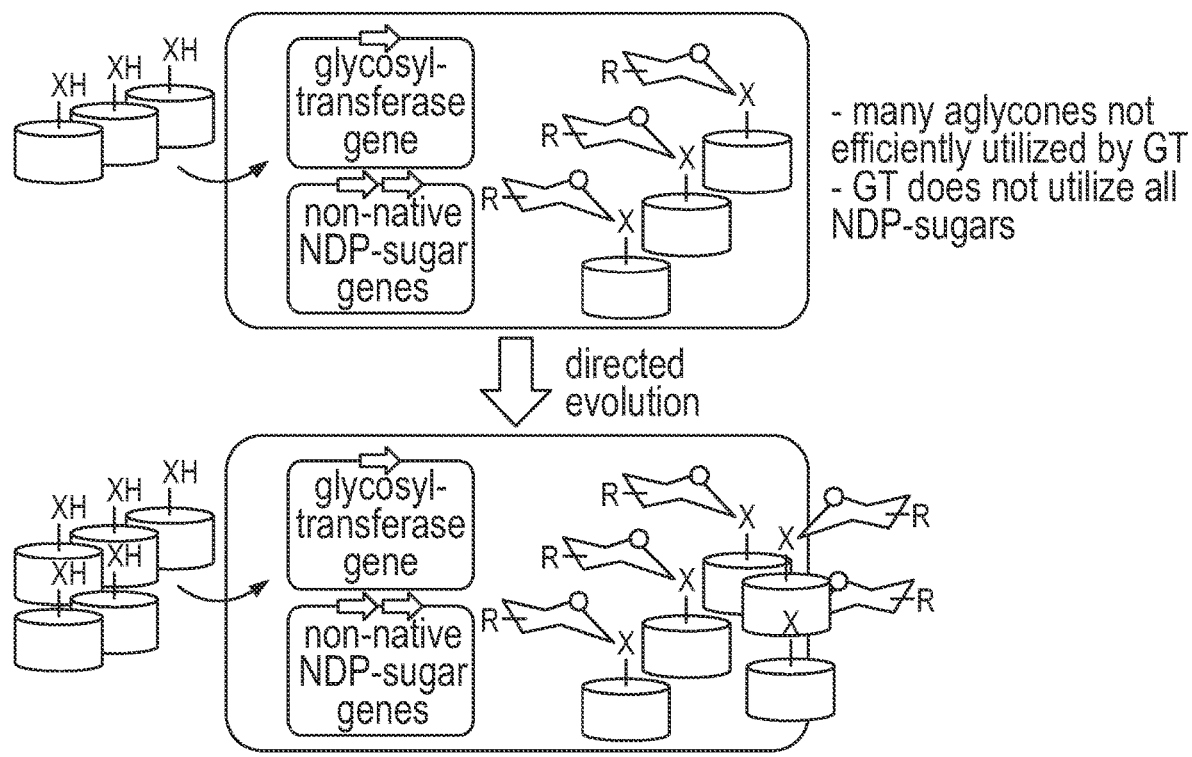
Figure 10D:
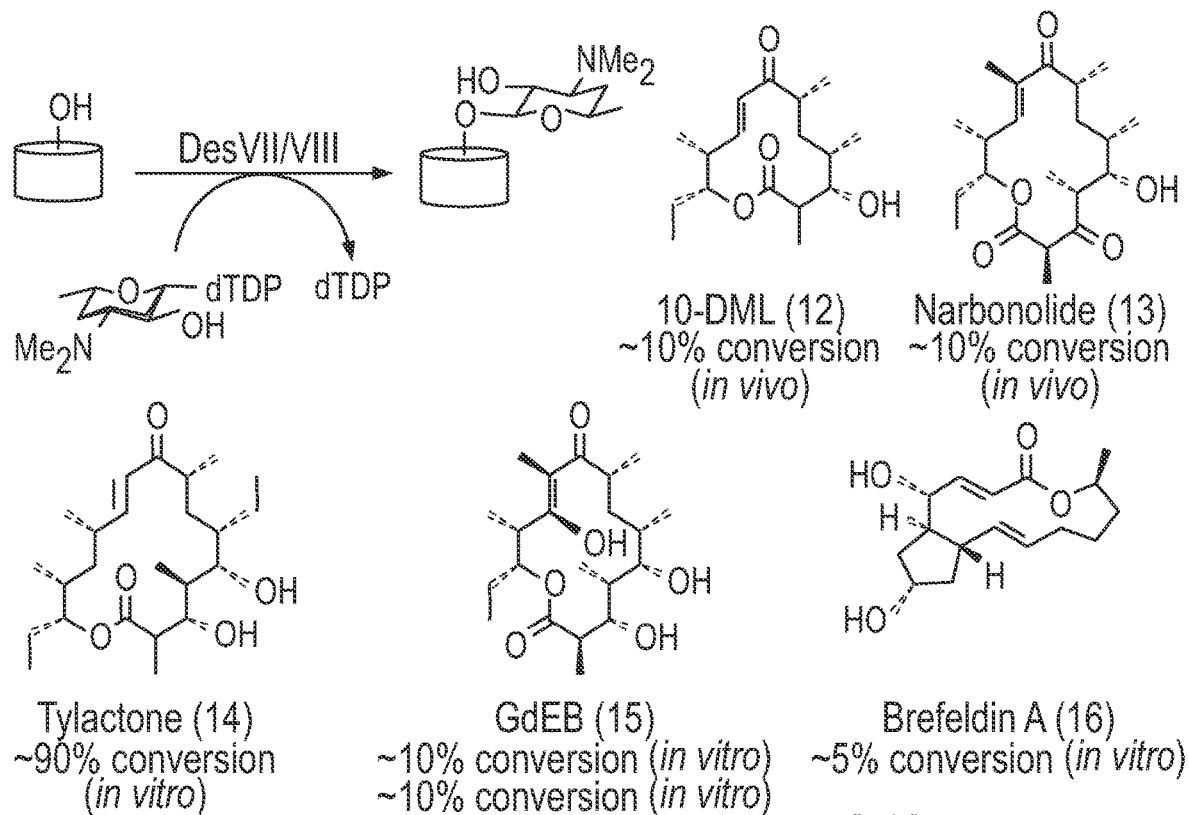

Anthracyclines (e.g. doxorubicin), enediynes (e.g. calicheamicin), avermectins (e.g. avermectin $B_{1a}$), polyenes (nystatin $A_1$), and perhaps most notably, macrolides are examples of glycosylated polyketides. The sugars of macrolide antibiotics such as erythromycin A are absolutely essential for the ability of macrolides to inhibit protein synthesis at the ribosome and the corresponding aglycone is not an effective antibiotic. In fact, altering the glycosylation pattern of macrolides can even change the biological activity from antimicrobial to anti-viral or anti-parasitic. Glycosylated polyketides have also been used as probes to perturb biological function. Classical chemical approaches for the synthesis of glycoconjugates are challenging since regio- and stereochemical control of glycosidic linkage formation requires multiple protection/deprotection steps, typically resulting in poor yields. On the other hand, biosynthetic approaches for glycoconjugate synthesis are an attractive alternative to traditional chemical synthesis, since enzymes are usually highly regio- and stereoselective and do not require complex protection strategies. Moreover, approaches that involve enzymes are particularly promising given the potential to produce multi-gram scale quantities of natural products via bacterial fermentation, at low cost, and with minimal use of organic solvents. Accordingly, biosynthetic pathways responsible for the synthesis of glycosylated polyketides have been intensively investigated as tools for the production of glycosides. Glycosylation, which is often rate limiting, is achieved through the transfer of a sugar moiety from an activated glycosyl-donor, usually in form of a nucleotide diphosphate (NDP)-sugar, and is catalyzed by glycosyltransferases (GTs) (FIG. 10(A)). The GT and the genes required for production of the NDP-sugar are frequently grouped together in a module within the gene cluster (FIG. 10(B)). Conveniently, the polyketide synthase (PKS) genes are usually also grouped together (FIG. 10(B)). This convenient (yet superficial) modularity of biosynthetic pathways lends itself to the 'design-build-test' mantra of synthetic biology. Thus, mixing and matching various NDP-sugar pathways and GTs between heterologous or native hosts has been explored in an effort to produce non-natural hybrid natural product glycosides. Perhaps the most potentially versatile combinatorial biosynthesis strategy in this respect involves feeding aglycones into a heterologous host that is engineered to express a non-native GT and the enzymes for synthesis of a non-native NDP-sugar (FIG. 10(C)). This takes advantage of fast-growing, genetically tractable heterologous hosts such as *E. coli*. Yet, most hybrid glycosylation pathways suffer from poor bioconversion yields and limited substrate scope. For example, an engineered *Streptomyces venezuelae* system, in which a non-native TDP-olivose biosynthesis pathway was introduced, produced <10% yield of the desired glycosides after aglycone feeding to the culture. They key factor limiting the scope and efficiency of engineered glycosylation pathways is the poor activity and narrow substrate scope of natural product GTs. In fact, only a small number of GTs display substrate specificity sufficiently broad for generating libraries of glycosides. Moreover, GTs can be remarkably sensitive to relatively minor structural modifications to both the aglycone and NDP-sugar. The specificity of the macrolide GT DesVII (along with its required accessory protein, DesVIII) exemplifies this major limitation (FIG. 10(D)). The relatively large number of GT crystal structures that are now available has proven insufficient to enable rational redesign of GT substrate specificity. Thus, the molecular determinants that control substrate specificity are unknown. This is particularly frustrating given the structural modularity of natural product GTs whereby the N- and C-terminal domains of GTs each house the acceptor and NDP-donor binding site, respectively. These domains could be exchanged between various GTs to construct chimeric enzymes for the synthesis of hybrid glycosides. However, this has yet to be realized, likely due to the poor understanding of inter-domain communication and catalysis in GTs. Directed evolution offers an opportunity to overcome these limitations (FIG. 10(C)). However, macrolide GTs have yet to be engineered by directed evolution or rational redesign. The closest example involved engineering the oleandomycin GT OleD by screening the ability of OleD mutants to glucosylate 4-methylumbelliferone. Activity/specificity towards macrolides was not and could not be targeted in this study. The critical issue is the lack of high-throughput screens/selections for polyketide GTs. The current methods disclose how to utilize genetically modified MphR for screening libraries of GT variants for production of polyketide glycosides. Non-limiting examples of these MphR biosensors are disclosed herein.

Example 6

Biosensors for Detection of Erythromycin A C6 O-Methylation

Figure 7:
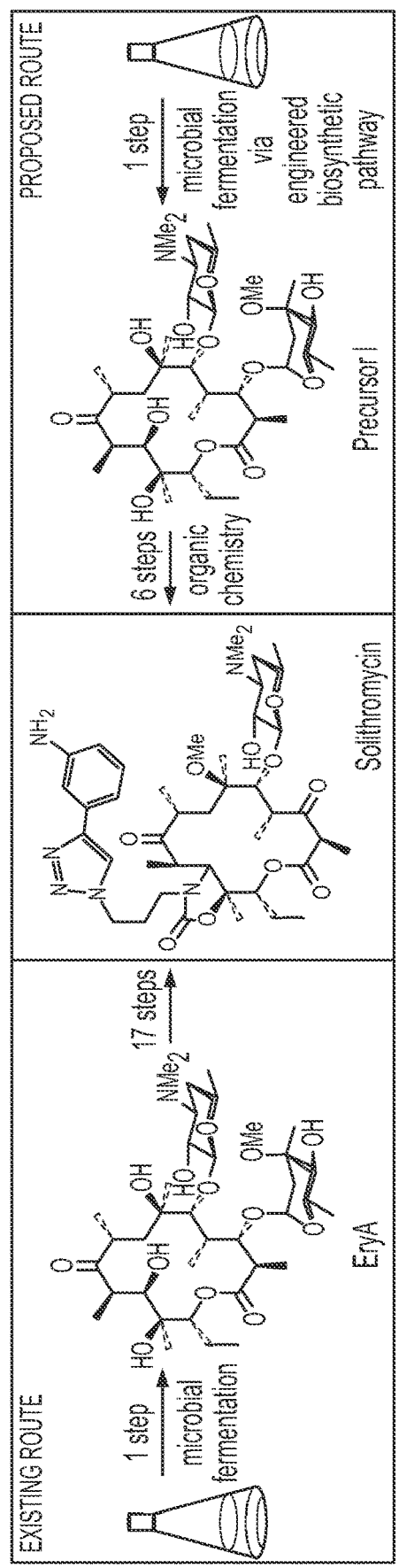
FIG. 7. Existing 18-step route to solithromycin compared to a biosynthetic route.
Figure 8A:
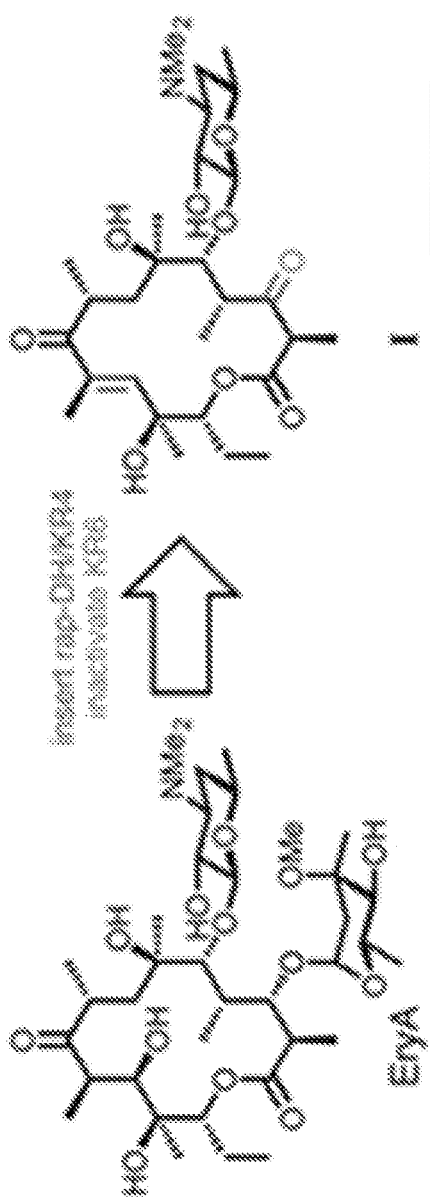
FIGS. 8A-8B. Biosensor-guided engineering of a solithromycin precursor.
Figure 8B:
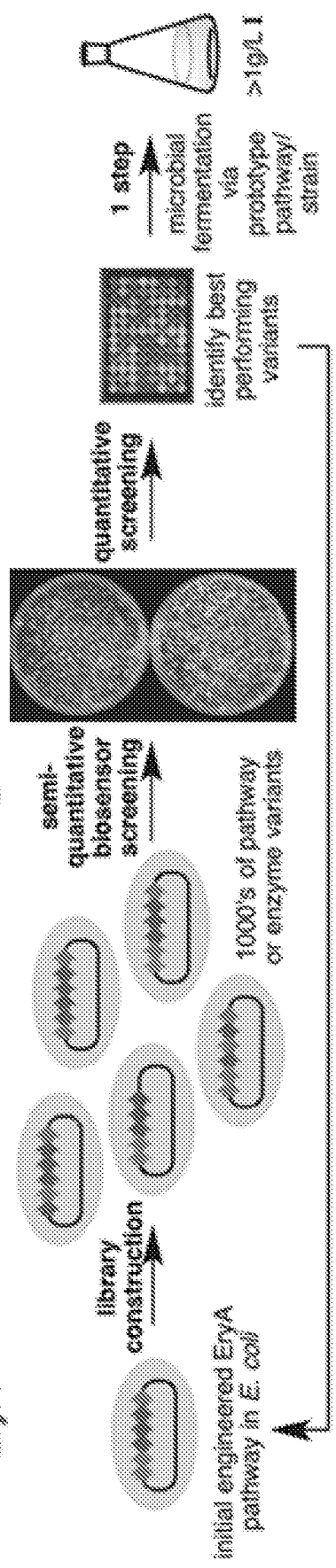

Erythromycin A is one of most widely prescribed macrolide antibiotics. Yet, its poor bioavailability and limited spectrum of activity have spurred tremendous efforts to alter the structure of erythromycin A and have resulted in the development of several generations of novel antibiotics. For example, the second generation macrolide antibiotic 6-O-methylerythromycin (clarithromycin, FIG. 5(A)) has been remarkably successful due to its enhanced antibacterial activity, improved pharmacokinetic properties, and expanded spectrum of activity. Unfortunately, like other 14-membered macrolides, clarithromycin has poor activity against macrolide-resistant bacteria. Newer generation macrolides such as solithromycin (See FIG. 7) may address the problem of resistance but also depend on the 6-O-methylation for activity. The simple C6 O-methylation of erythromycin A prevents hemi-ketal formation with the C9-ketone in the acidic environment of the stomach. However, this simple semi-synthetic modification requires six steps to transform erythromycin A to clarithromycin (FIG. 5(A)). The industrial process for production of clarithromycin therefore involves microbial fermentation of erythromycin A, extraction, and chemical synthesis. The methods described herein are used to provide an engineered microbial strain that produces clarithromycin directly, resulting in a faster, cheaper, and "greener" world supply of this pharmaceutical. Moreover, such a production strain could be coupled with other biosynthetic transformations to rapidly produce new clarithromycin analogues for further drug discovery efforts.

Figure 5A:
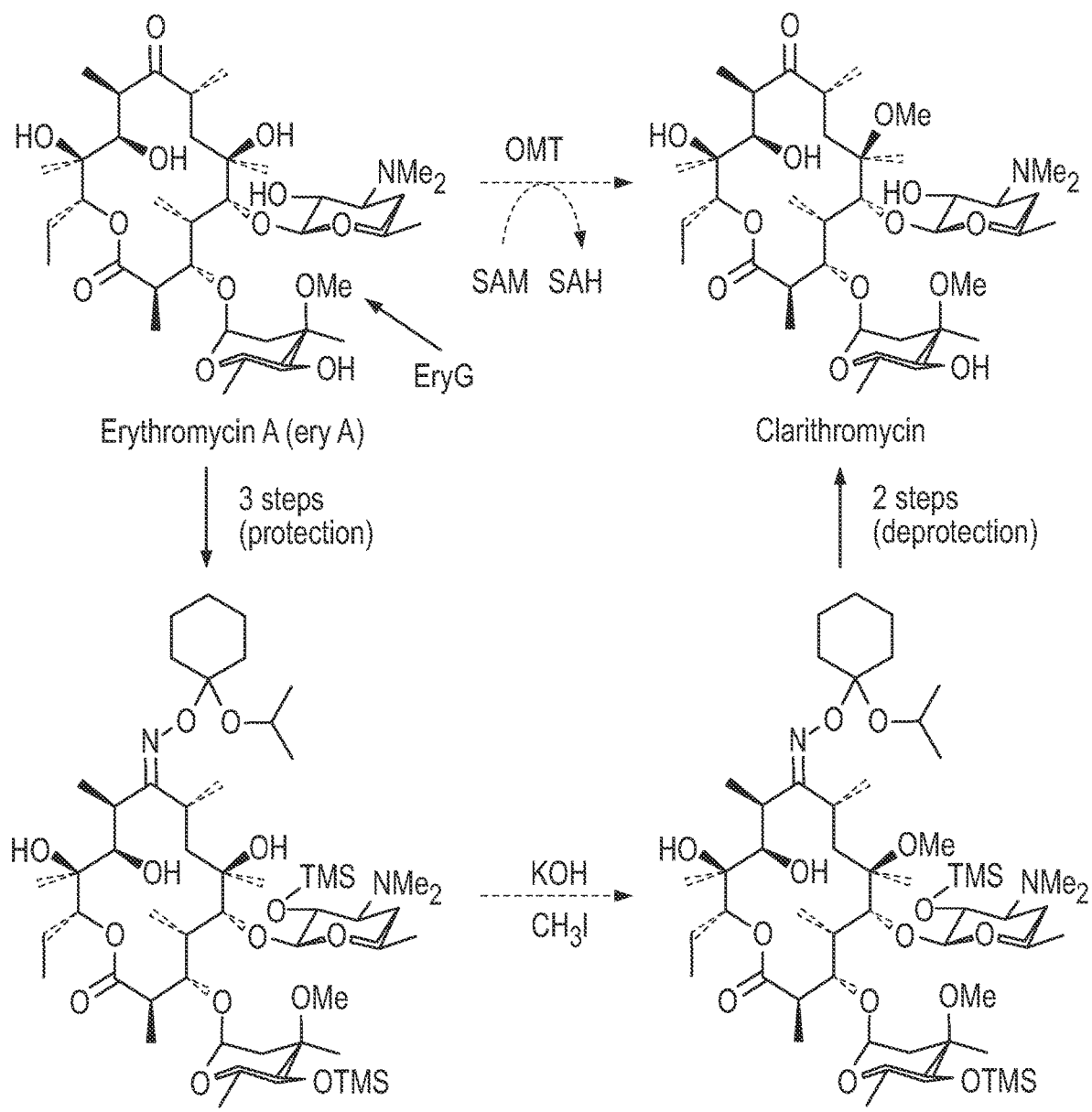
FIGS. 5A-5B. Biosynthesis of clarithromycin via an engineered O-methyltransferase (OMT).
Figure 5B:
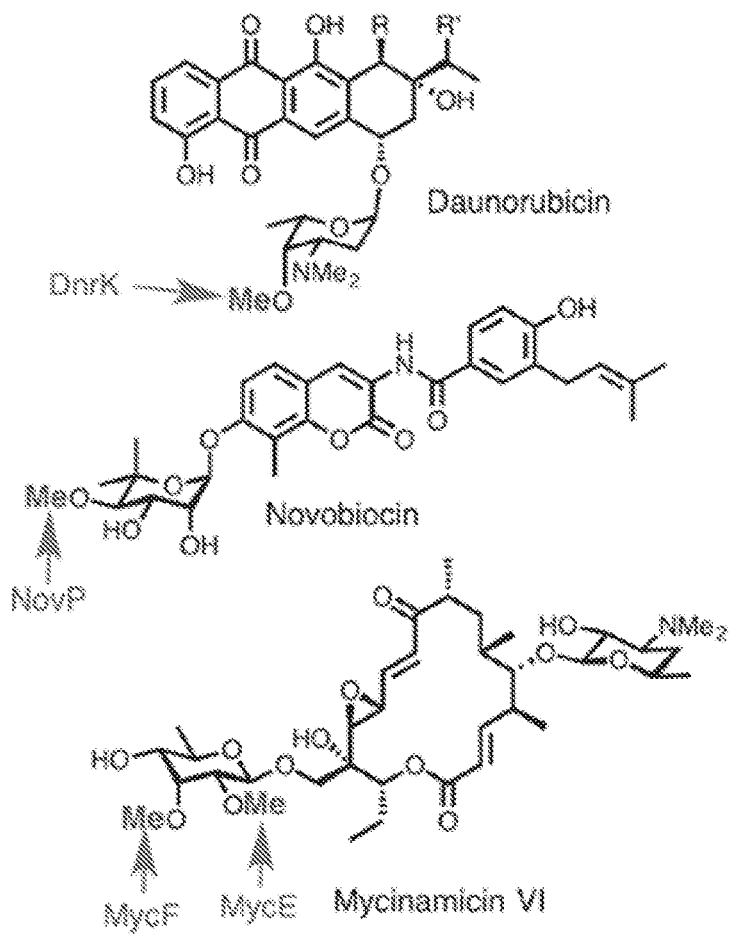

For example, an O-methyltransferase (OMT) could afford clarithromycin in a single step from erythromycin A (FIG. 5(A)). OMTs are a diverse group of enzymes distributed throughout all domains of life and catalyze a simple $S_N2$-like substitution using the cofactor S-adenosyl-L-methionine (SAM). The diverse target substrates of OMTs include nucleotide-sugars, carboxylic acids, phenols, and natural products. Yet, there are no known examples of OMTs that methylate the C6-hydroxyl group of erythromycin A. However, many OMTs target hydroxyls of sugar residues on polyketides and macrolides (FIG. 5(B)). Indeed, methylation of the cladinose residue of erythromycin A is catalyzed by EryG, an OMT from the erythromycin A gene cluster (FIG. 5(A)). Although some OMTs can methylate several positions, most OMTs seem to be regioselective with respect to the acceptor hydroxyl. Thus, example approaches to an OMT for the conversion of erythromycin A to clarithromycin are to engineer the regioselectivity of EryG or manipulate the substrate specificity of another candidate. In support of this, natural product OMTs, including macrolide OMTs, are known to display acceptor promiscuity (a good starting point for directed evolution), and the specificity of OMTs has been changed. Moreover, the regioselectivity of phenylpropanoid and flavone OMTs has been altered via site-directed mutagenesis, iterative saturation mutagenesis, and error-prone PCR. Notably, although there are >50 structures of OMTs in the Protein Data Bank (PDB), many with bound SAM, only a few include the bound acceptor, thus precluding the effective use of structural based approaches to OMT redesign. The recently described structures of two OMTs involved in the biosynthesis of mycinamicin (FIG. 5(B)) correctly predicted that these OMTs use alternative macrolides and also enabled relaxation of specificity via mutagenesis. These demonstrations cumulatively highlight additional examples of engineering the regio- and substrate specificity of OMTs.

A genetic selection to identify OMT variants from large combinatorial libraries of OMT mutants can be used. Directed evolution and selections are known strategies for dramatically altering enzyme regio- and substrate specificity. The key challenge is that screening/selection methods with the requisite throughput or general applicability are not available for natural product OMTs. There are no reported ultra-high-throughput screens for methyltransferases. Most polyketides are not chromophores or fluorophores and don't offer a spectrophotometric change upon methylation that could be monitored. Moreover, methylation typically does not provide a suitable phenotype that can be leveraged for a screen or selection. Mass spectrometry is suitable for screening relatively small libraries of variants when the requisite instrumentation and expertise is available. Regardless, the ability of high-throughput mass spectrometry to quantify polyketides in complex mixtures and to distinguish congeners is unproven. Moreover, identification of suitable OMTs for the biosynthesis of clarithromycin might require the ability to screen hundreds of thousands of variants (if not more), a throughput that is well out of the range of liquid chromatography. To address this need, an MphR sensor is generated that is activated by clarithromycin but not erythromycin A. Given OMT libraries expressed in E. coli are fed with erythromycin A, and E. coli is not able to modify the structure of erythromycin A, the sensor must be selective for clarithromycin in the presence of erythromycin A, and the reporter MphR signal should be low (ideally zero) in the presence of erythromycin A.

Figure 6A:
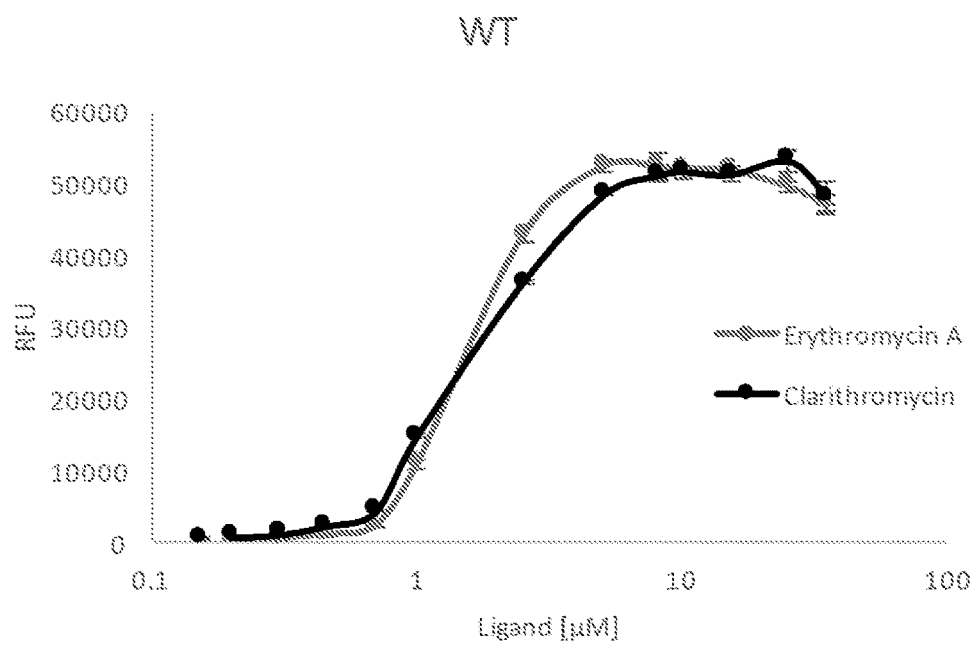
FIGS. 6A-6B. Clarithromycin selective MphR sensor.
Figure 6B:
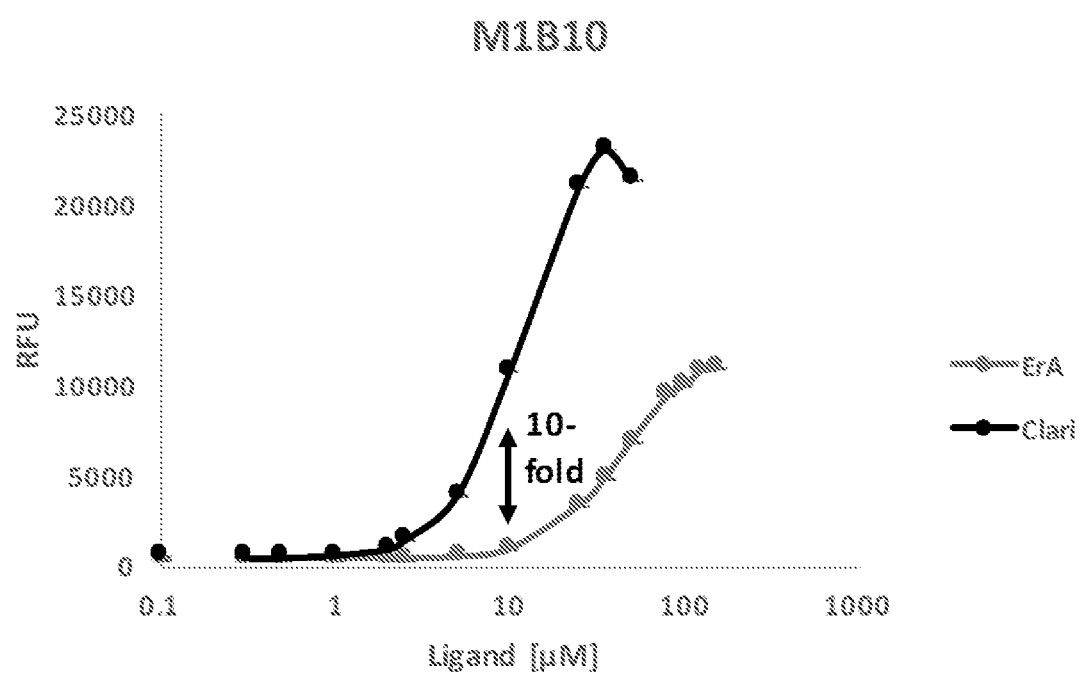

Directed evolution has been used here to alter the ligand specificity of MphR. A library of MphR variants was created by error-prone PCR (epPCR). Reasoning that many mutations could lead to misfolded variants or those that do not bind to the operator, and that variants are required that are not activated by ErA, fluorescent activated cell sorting (FACS) was first used to remove those variants that were constitutively 'ON' in the presence of ErA. To test the capacity of random mutations to alter the ligand specificity of MphR, the initial goal was to find variants that were more selective with clarithromycin compared to erythromycin A. Thus, some of the 'OFF' library members were duplicated and each screened in the presence of clarithromycin and erythromycin A. Several variants were identified that showed higher GFP reporter signals in the presence of clarithromycin compared to erythromycin A. One particular clone, "M1B10" (comprising amino acid changes T49I, L89V, D98N, E109D) was selected for further analysis. GFP fluorescence was measured in the presence of varying concentrations of erythromycin A or clarithromycin (0.1-150 µM) and showed that the selectivity of this MphR variant was now shifted towards clarithromycin. For example, at 10 µM ligand, the fluorescence response with clarithromycin is 10-fold higher than with erythromycin A (FIG. 6). Remarkably, the dynamic range ($GFP_{max}$-$GFP_{min}$) of M1B10 is still ~50% that of the WT MphR.

Figure 26A:
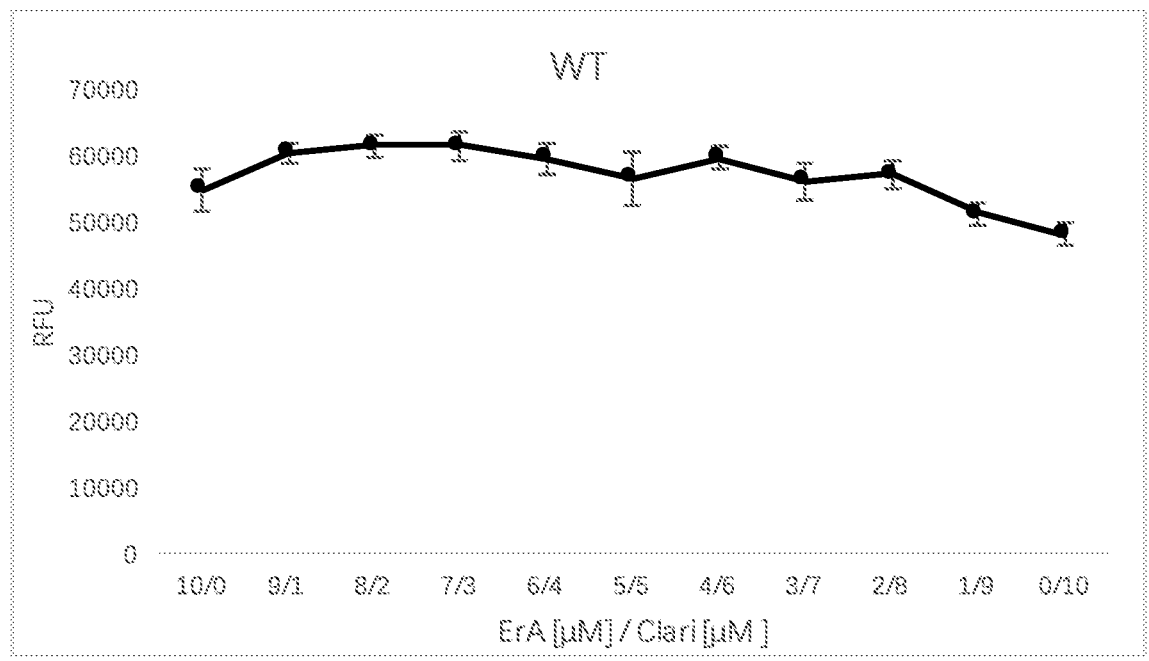
FIG. 26A. Analysis of wild-type (WT) MphR using a range of ErA/Clarithromycin concentrations. This shows that the WT biosensor does not discriminate between these two polyketides and cannot be used to determine the concentration of clarithromycin in the presence of ErA.
Figure 26B:
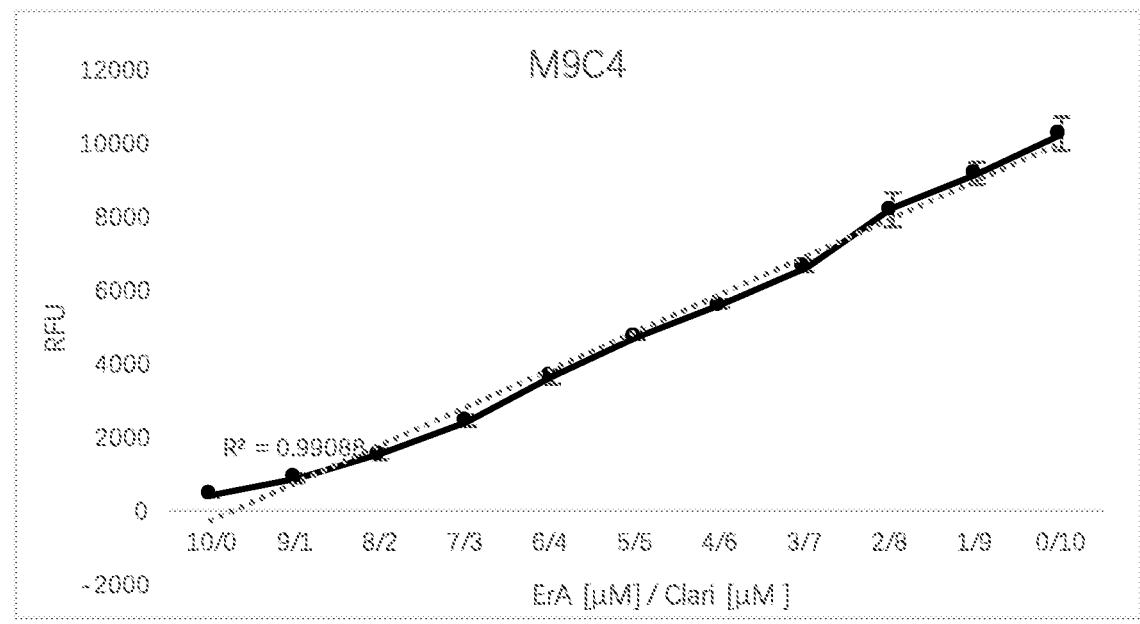
FIG. 26B. Analysis of MphR mutant M9C4 using a range of ErA/Clarithromycin concentrations. This shows that the WT biosensor does discriminate between these two polyketides and can be used to determine the concentration of clarithromycin in the presence of ErA.

MphR M1B10 was replaced by the variant "M9C4." MphR WT was subjected to structural-guided mutagenesis (R122T mutation), and error-prone PCR based on R122T mutation, yielding the variant "M9C4". This variant is the most clarithromycin/erythromycin selective biosensor reported to date. At 10 µM ligand, the fluorescence response with clarithromycin is 29-fold higher than with erythromycin A. The RBS of the variant E7 was included (E7_M9C4), further improving sensitivity (FIG. 19; Table 8). The sensitivity of M9C4 was tested using mixtures (e.g. 0:10 thru 10:0) of ErA/clarithromycin at fixed total concentration of 10 µM. The data showed that M9C4 could be used to determine the concentration of clarithromycin the presence of erythromycin A (ErA) in the linear range of 0-10 µM whereas the WT biosensor was not effective (FIG. 26).

TABLE 8

| | | M9C4 clarithromycin specific biosensor | | | |
|---|---|---|---|---|---|
| Mutation | Ligand | Dynamic range (RFUmax-RFUmin) | $K_{1/2}$ (µM) | Selectivity ($K_{1/2}$ErA/$K_{1/2}$Clarithromycin) | Hill coefficient |
| WT | ErA | 52125 | 1.51 | 0.92 | 3.52 |
| | Clari | 52749 | 1.64 | | 2.30 |
| R122T | ErA | 3666 | 47.09 | 1.94 | 2.39 |
| | Clari | 5751 | 24.22 | | 3.03 |
| M9C4 | ErA | 11342 | 68.32 | 6.74 | 2.03 |
| | Clari | 33326 | 10.14 | | 1.49 |
| E7_M9C4 | ErA | 15318 | 29.33 | 6.01 | 1.95 |
| | Clari | 46345 | 4.88 | | 1.49 |

Example 7

Identification of Enzymes for Synthesis of Clarithromycin

The objective here is to utilize MphR variants that recognize semi-synthetic polyketide analogues to identify enzymes for their chemo-enzymatic synthesis. MphR-based sensors can be used to identify and enrich novel polyketide tailoring enzymes by sensing the production of the desired product in vivo. An MphR variant specific for 6-O-methylerythromycin (clarithromycin) is generated and in vivo selections are performed to identify novel O-methyltransferases (OMTs) that enable the in vivo production of this valuable semi-synthetic derivative. Such enzymatic activity is difficult or impossible to identify without a genetically encoded biosensor and this approach could afford an array of other semi-synthetic derivatives.

Figure 9A:
FIGS. 9A-9D. O-methyltransferase (OMT) scaffolds for directed evolution.

Several candidate OMTs have been identified for directed evolution. EryG is a candidate given it already recognizes the desired substrate, albeit in a different conformation than required. EryG has been expressed in E. coli and displays some macrolide promiscuity. Given a crystal structure for EryG is not available, Phyre2 and I-TASSER were used to generate homology models. The conserved SAM-binding site was identified by Phyre2 and I-TASSER, while the putative macrolide-binding site were identified by comparison to known OMT sequences and acceptor-bound structures (FIG. 9(A)). Furthermore, the server CAVER predicted a cavity that agreed with a manual approach (FIG. 9(A)).

Figure 9B:
Figure 9C:
Figure 9D:
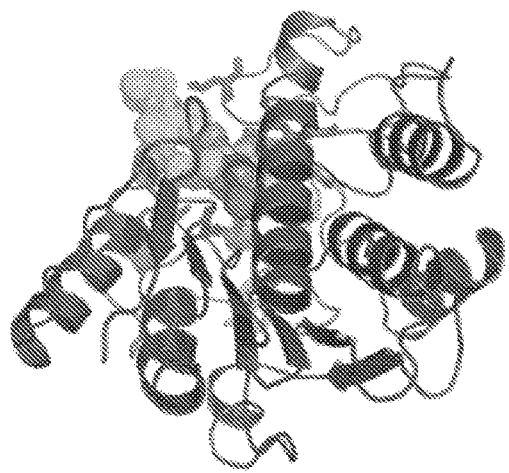

DnrK is an OMT involved in daunorubicin biosynthesis (FIG. 9(B)). The structure shows that the large hydrophobic acceptor substrate binds into a hydrophobic deep binding pocket (FIG. 9(C)). The fact that (1) hydrophobic binding pockets often render enzymes highly evolvable, (2) DnrK uses a simple proximity driven mechanism, and (3) the acceptor-binding site is known, makes DnrK a candidate for redesign. Finally, the MycF structure shows that the macrolactone is located in a hydrophobic region at the opening of the active site funnel and makes no specific contacts with MycF (FIG. 9(D)). Consistent with this, MycF has been shown to display macrolactone promiscuity[37].

With a clarithromycin-sensor in place, approaches for the discovery of novel OMT activity using EryG, MycF, and DnrK as scaffolds can be pursued. epPCR libraries of these enzymes are generated in addition to multi-site saturation mutagenesis at residues lining each acceptor-binding pocket (FIG. 9(A)-(D)). Mutation rates as high as 3-4 amino acid mutations per gene and multi-site saturation of 6-7 simultaneous residues can be searched using MphR-based selections. Given the breadth of OMT acceptor substrates and variety of catalytic mechanisms, the sequences of most OMTs are highly divergent, even though most OMTs belong to the same superfamily of SAM-dependent MTs and share similar overall topologies. Thus, SCHEMA structure-guided recombination to prepare protein chimera libraries from all three scaffolds can be used. Initial candidate OMTs could support conversion of μM concentrations of clarithromycin in the timeframe of a culture growth and this feature was used to drive the evolution of MphR variants with the requisite selectivity and sensitivity. The gfp reporter gene of the current MphR plasmid system is replaced with a selection marker (e.g. chloramphenicol). The elegance of the in vivo biosensor is that the OMT selection process is made more selective simply by decreasing the concentration of clarithromycin. Thus, once activity of an OMT variant is identified that exceeds the activation threshold for the sensor, this variant is used to parent the next library and is subjected to selection using a lower (sub-activating) concentration of clarithromycin and/or less incubation time. Thus, each round enriches OMTs with better $k_{cat}$ and/or $K_m$.

Once activity is isolated and sufficiently robust to achieve in vivo conversion, OMT variants are expressed and purified for biochemical characterization. A genetic selection could enrich OMTs that methylate the C6-OH of erythromycin A, but also other hydroxyl groups. Thus, HPLC-ELSD coupled with MS is used to determine if other products are present. However, other regiospecificities could prove useful sources of new products. Once regiospecificity of the OMT is established, full characterization (e.g. $k_{cat}$, $K_m$, stability) is determined by HPLC-ELSD, using erythromycin A, SAM, and clarithromycin as a product standard. Moreover, SAM-analogues are utilized to determine whether the evolved OMTs can be used to alkyl-diversify macrolides.

Example 8

Biosensors for Production of an Advanced Solithromycin Precursor

Cempra, Inc (Chapel Hill) have completed Phase III clinical trials for solithromycin and a New Drug Application (NDA) is in progress for the treatment of community-acquired bacterial pneumonia. Solithromycin is chemically synthesized via a lengthy 19-step sequence of reactions (FIG. 7). To streamline the synthesis of this promising new antibiotic, an engineered biosensor can provide the advanced precursor I by simple microbial fermentation, in one step, using a known enzymatic pathway (FIG. 7). The precursor is then converted to solithromycin via a proposed chemo-enzymatic route (6-steps) or by known organic chemistry (11) steps, thus eliminating up to 10 chemical steps. Crucially, providing I biosynthetically circumvents some of the most inefficient chemistry (installing the double bond). The logic of polyketide biosynthesis is understood, such that an artificial biosynthetic pathway for I has been designed based on validated genetic modifications to the biosynthetic gene cluster for erythromycin A (FIG. 8). Yet, such modified pathways usually produce low product titers insufficient for large-scale fermentation. A biosensor for detection of I would enable screening many thousands of enzyme/pathway variants for production of I (FIG. 7).

Precursor I can be produced in an *E. coli* strain because: (1) a plasmid system for expressing entire polyketide gene clusters in *E. coli* can be used and have demonstrated erythromycin A production; (2) suitable *E. coli* strains for expression of the such genes including BAP1 can be used; and (3) the natural production host cannot provide the growth speed, technical amenability, and scalability offered by *E. coli*. Additionally, the necessary genetic manipulations in *E. coli* can be performed by those skilled in the art.

The artificial pathway is constructed in pieces via commercial gene synthesis, and inserted into *E. coli* BAP1. The prototype strain is tested by examining I in lysed cells and/or culture supernatant directly by LC-MS analysis. Notably, I is not toxic to *E. coli*. Subsequently, baseline I production, expected to be ~1 mg/L culture broth, is determined by LC-MS. The MphR variant is capable of detecting I produced via the strain by measuring the GFP reporter signal. The unnatural DH/KR insertion (FIG. 8) is likely to be responsible for the poor product titer of this pathway. Accordingly, a library of variants is constructed using standard molecular biology techniques in which the composition of the linkers surrounding this insertion are varied. Top performing library members are identified by screening thousands of clones in agar-plates under a UV lamp. The hits are copied, and re-assayed in microplates, allowing quantification in a microplate reader. The DNA sequences of the most productive library members are then obtained.

Given the known polyketide product titers of in vivo systems, a sensor that can detect I in the linear range 0-100 μM with a ~50 μM $K_{1/2}$ and fold-activation similar to WT MphR (with erythromycin A) is useful. Because the initial artificial pathway can produce I, albeit in poor yield, significant (e.g. >10-fold compared to initial strain) further mutations identified can provide critical proof-of-principle that biosensor-guided engineering is a viable alternative to traditional chemical synthesis of the precursor. Then, more elaborate libraries of variants can be generated and screened over multiple generations to furnish further mutations and improvements. Ultimately, product titers >1 g/L are typically needed for commercial viability of the production process.

The ability of the MphR clone "PikB1" to detect a Solithromycin biosynthetic intermediate (see structure below) was determined. This biosensor can detect the intermediate at concentrations as low as 0.1 μM (FIG. 20; WT $K_{1/2}$70.9±4.6 uM; PikB1 $K_{1/2}$1.46±0.16) making it suitable for identifying mutant strains capable of producing the intermediate in engineered microbes. Moreover, this intermediate can be accessed by simple genetic modifications to the genome of the erythromycin producing strain. Thus, biosensors like these improve the productivity of other modified producing strains that produce valuable biosynthetic intermediates that can be used to access highly diversified antibiotics through semi-synthesis.

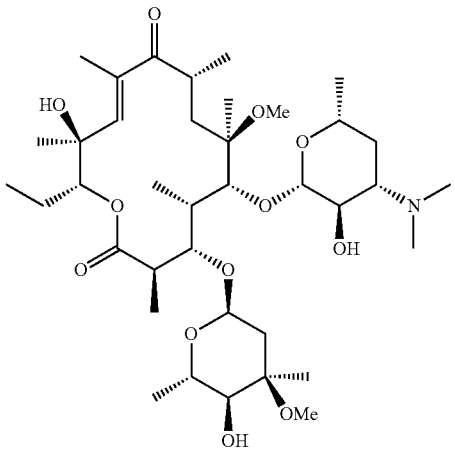

Solithromycin biosynthetic intermediate

Example 9

Figure 13:
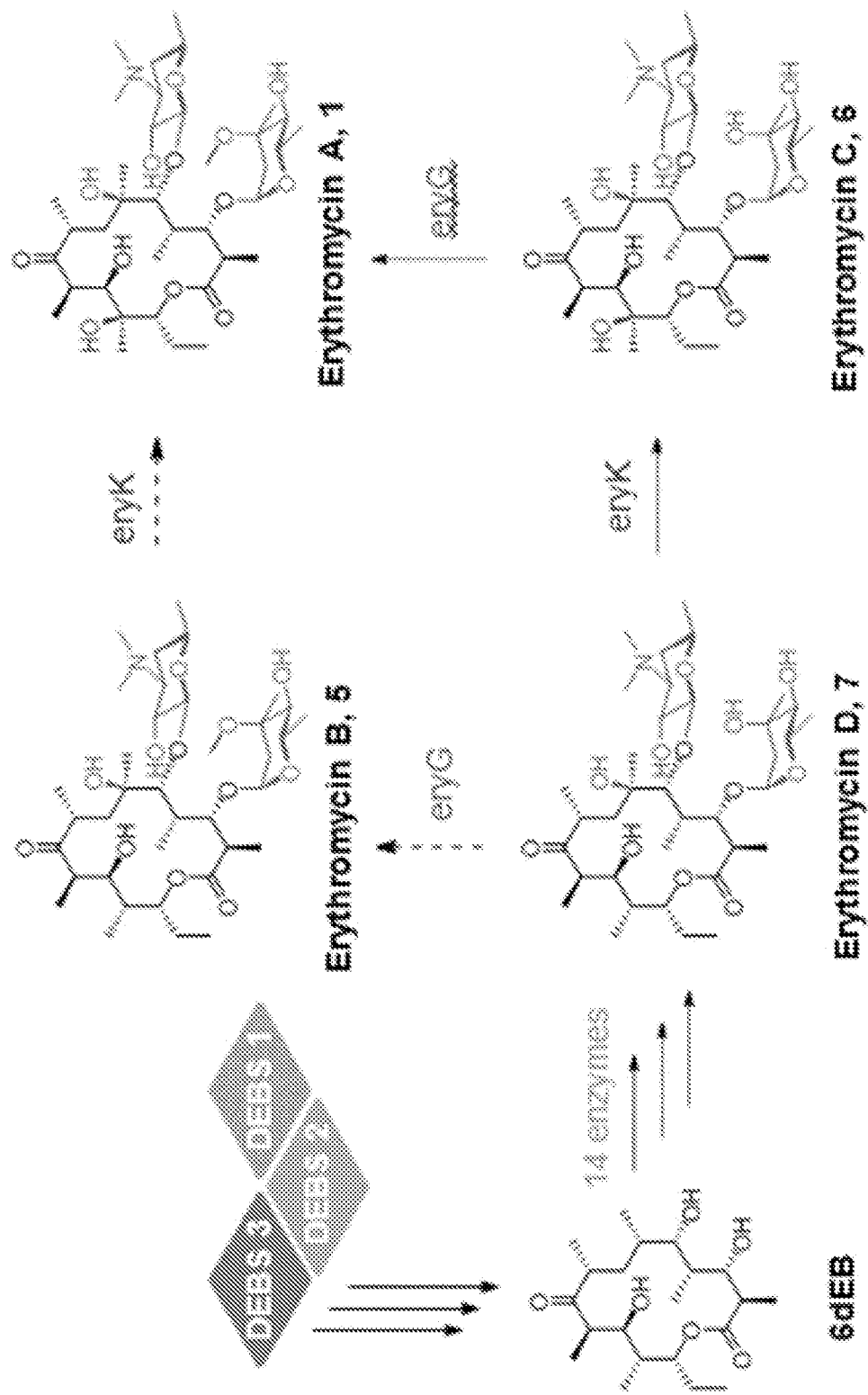
FIG. 13. Late-stage erythromycin A biosynthesis. 6dEB, produced by DEBS1-3, is modified by a suite of enzymes to yield erythromycin D. Biosynthesis from erythromycin D to erythromycin A proceeds via biosynthetic intermediate erythromycin C (filled arrows), or by the shunt pathway via intermediate erythromycin B (dashed arrows). The eryK-catalyzed C-12 hydroxylations and eryG-catalyzed mycarosyl O'-methylations are shown in the figure.

Engineering MphR Biosensors That Discriminate Between Late Stage Macrolides in Erythromycin A Biosynthesis Erythromycin A is a macrolide produced by the organized biosynthesis of type I polyketide synthase (PKS) and several late-stage tailoring enzymes. 6-Deoxyerythronolide B Synthase (DEBS) is organized as three giant polypeptides (DEBS1-3) that assemble the macrolactone 6-deoxyerythronolide B (6 dEB). 6 dEB is further tailored by P450 monooxygenases, glycosyltransferases, and a methyltransferase to yield the final product, erythromycin A (FIG. 13).

Recently reported titers of one cell biosynthesis of erythromycin A in *E. coli* are ~1 mg/L (Zhang H, et al. Complete Biosynthesis of Erythromycin A and Designed Analogs Using *E. coli* as a Heterologous Host. Cell Chemistry & Biology. 2010; 17(11):1232-40). The impressive coordination of 26 heterologous proteins to produce a foreign natural product notwithstanding, this yield can be seen as suboptimal, since the aglycone precursor, 6 dEB, is routinely produced in *E. coli* shake-flask cultures exceeding 100 mg/L (Boghigian B A, et al. Multi-factorial Engineering of Heterologous Polyketide Production in *Escherichia coli* Reveals Complex Pathway Interactions. *Biotechnology and Bioengineering*. 2011; 108(6): 1360-71). Rather than solely produce the single macrolide erythromycin A, heterologous biosynthesis results in mixtures of erythromycins A, B, C and D.

Typical erythromycin A biosynthesis occurs via the erythromycin C pathway. A P450 hydroxylation catalyzed by eryK converts erythromycin D to erythromycin C. Subsequently, the methyltransferase eryG catalyzes the S-adenosylmethione (SAM) dependent methylation of erythromycin C to yield erythromycin A. Erythromycin B is generally regarded as an undesired shunt product of a competing alternative pathway that reverses the order of hydroxylation and methylation of erythromycin D so that eryG methylation occurs first (Montemiglio, L C, et al. Redirecting P450 EryK Specificity by Rational Site-directed Mutagenesis. *Biochemistry*. 2013; 52(21) 3678-87; Savino, C, et al. Investigating the Structural Plasticity of a Cytochrome P450: Three-dimensional Structures of P450 EryK and Binding to its Physiological Substrate. *Journal of Biological Chemistry*. 2009; 284(42) 29170-9).

Figure 14A:
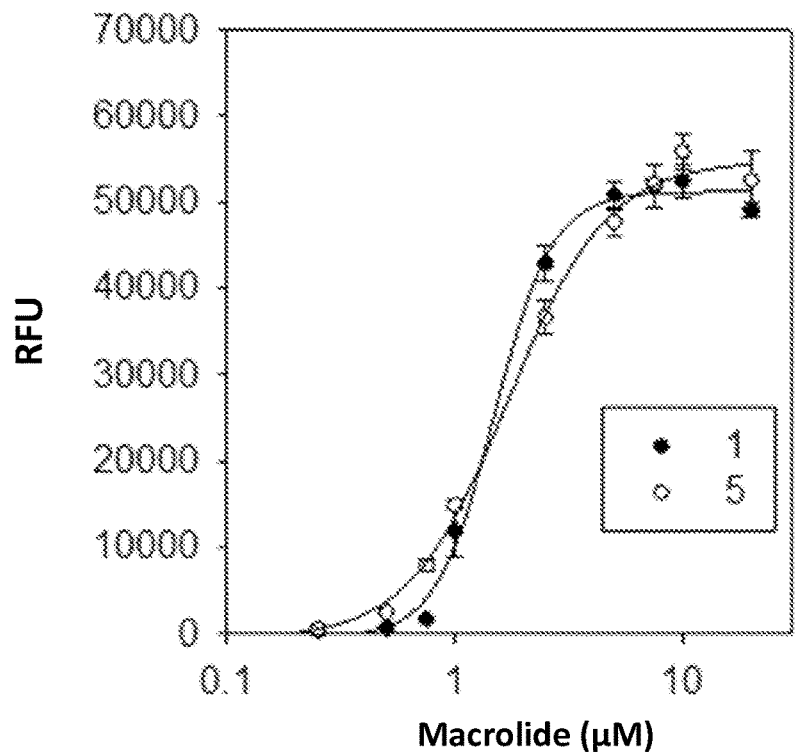
FIGS. 14A-14B. Dose-response curves of the wild-type sensor (FIG. 14A) and the erythromycin A specific sensor MphR-P4L/W107L/H193R (FIG. 14B) in the context of discriminating between erythromycins A (compound 1) and B (compound 5). Clone MphR-P4L/W107L/H193R is capable of significant activation by erythromycin A solely, unlike the general wild-type macrolide biosensor.
Figure 14B:
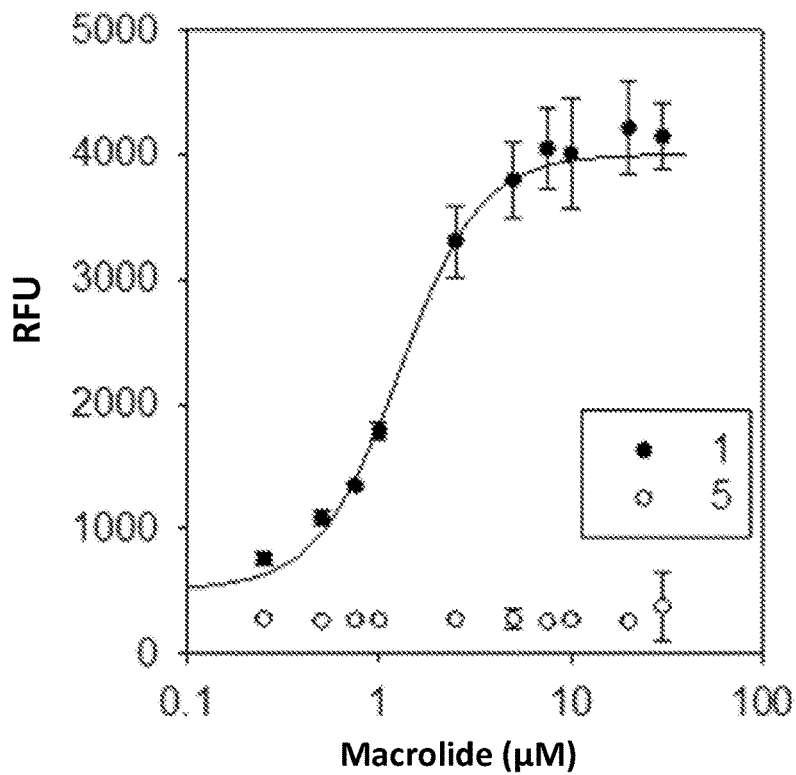

Biosensor guided screening of natural or heterologous erythromycin A biosynthesis would rely of the ability of the biosensors to report the true concentration of erythromycin A without falsely over-reporting yield due to off target activation by a late-stage biosynthetic intermediate. MphR-WT was assayed for its ability to detect the late-stage biosynthetic intermediates of erythromycin biosynthesis, erythromycins B and C. Compared to erythromycin A, erythromycins B and C activate MphR-WT in a nearly identical manner (FIG. 14, Table 9).

Successful application of the method above revealed MphR-P4L/W107L/H193R, a clone with enhanced erythromycin A selectivity versus erythromycin B. Compared to MphR-WT, MphR-P4L/W107L/H193R demonstrated no detectable or calculable activation by erythromycin B but retained significant erythromycin A sensitivity (FIG. 14, Table 9).

TABLE 9

Performance features of the wild-type sensor with erythromycins A and B.

| MphR-WT | $K_{1/2}$ (μm) | Cooperativity | dynamic range $(GFP_{max}-GFP_{min})$ | linear range of detection (μM) |
|---|---|---|---|---|
| 1 (ErA) | 1.49 | 3.39 | 52400 | 0.5-2.5 |
| 5 (ErB) | 1.72 | 1.99 | 55800 | 0.3-2.5 |

TABLE 10

Performance features of the P4L/W107L/H193R sensor with erythromycins A and B.

| MphR- P4L/ W107L/ H193R | $K_{1/2}$ (μm) | Cooperativity | dynamic range $(GFP_{max}-GFP_{min})$ | linear range of detection (μM) |
|---|---|---|---|---|
| 1 (ErA) | 1.27 | 2.04 | 3800 | 0.3-2.5 |
| 5 (ErB) | N.C. | N.C. | N.C. | N.C. |

As seen in Tables 9 and 10, MphR-P4L/W107L/H193R displays a clear selectivity shift towards erythromycin A from B, while maintaining nearly the same performance features as the wild-type sensor, except dynamic range. MphR-P4L/W107L/H193R can be used as a biosensor capable of distinguishing erythromycin A from its structurally similar precursors. Sensors capable of HTS allow contemporary techniques that leverage giant library sizes to improve true erythromycin A titers. In addition to usefulness as an erythromycin A detector with less off-target activation, MphR-P4L/W107L/H193R also serves as a sensor for the detection of P450 monooxygenase eryK-catalyzed C-12 hydroxylation of erythromycin A's core. MphR-P4L/W107L/H193R and newly developed sensors of this type provide the tools necessary for high-throughput screening of late-stage tailoring enzymes in the erythromycin biosynthetic pathway.

Example 10

Engineered MphR Biosensors

A summary of non-limiting examples of MphR biosensor mutations is provided in Table 11 below. A number of the mutations were discussed in the examples above. Additional mutations are shown in Table 11 that provide increased pikromycin sensitivity. Further mutations are shown in Table 11 that improved narbomycin sensitivity.

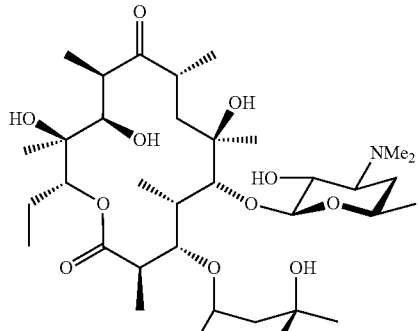

Erythromycin C

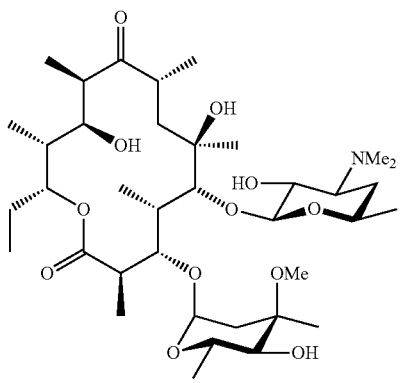

Erythromycin B

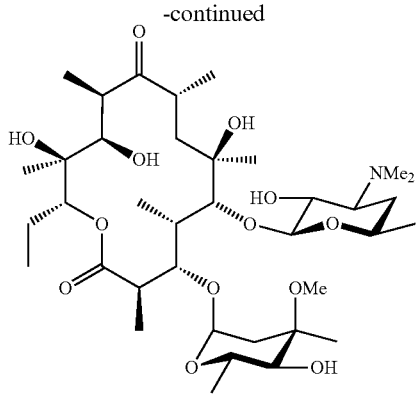

Erythromycin A

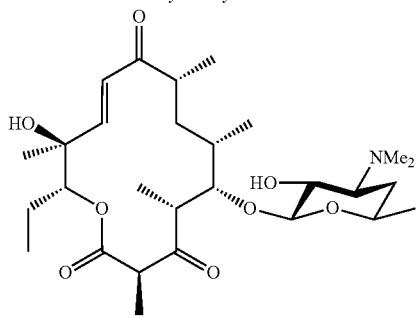

Pikromycin

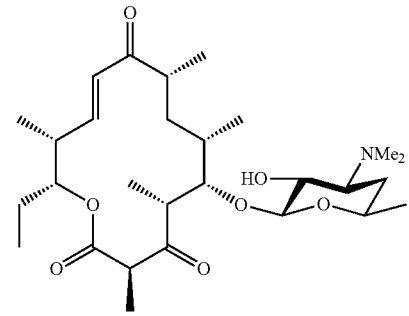

Narbomycin

TABLE 11

MphR Mutations

| Label | Mutation | Goal | Effect | Quantification |
|---|---|---|---|---|
| A3 | nt: A1G<br>aa: G76C | erythromycin A sensitivity | erythromycin A sensitivity | 3.6 times more sensitive vs. WT |
| E7 | nt: A4T<br>aa: V90I | erythromycin A sensitivity | erythromycin A sensitivity | 3.0 times more sensitive vs. WT |
| smRBS1A1 | nt: A1T/G2T/A3C | erythromycin A sensitivity | erythromycin A sensitivity | 9.9 times more sensitive vs. WT |
| QCMS3D6 | T17R | erythromycin A sensitivity | erythromycin A sensitivity | 2.4 times more sensitive vs. WT |
| QCMS3F8 | T17A/M59S | erythromycin A sensitivity | erythromycin A sensitivity | 1.6 times more sensitive vs. WT |
| QCMS5B4 | T27G/Q65M | erythromycin A sensitivity | erythromycin A sensitivity | 1.5 times more sensitive vs. WT |
| QCMS5D7 | T27A/M59E | erythromycin A sensitivity | erythromycin A sensitivity | 2.0 times more sensitive vs. WT |
| D3 (pikB1) | S106F | pikromycin sensitivity | pikromycin sensitivity | 118 times more sensitive vs. WT |
| D3 (pikB1) | S106F | Solithromycin precursor I sensitivity | Solithromycin precursor I sensitivity | 52 times more sensitive vs. WT |

TABLE 11-continued

| | MphR Mutations | | | |
|---|---|---|---|---|
| Label | Mutation | Goal | Effect | Quantification |
| D3 (pikB1) | S106F | YC-17 sensitivity | YC-17 sensitivity | 40 times more sensitive vs. WT |
| YCA11 | S31R | YC-17 sensitivity | YC-17 sensitivity | 8.5 times more sensitive vs. WT |
| Nbn.YCG11 | L39F | YC-17 and narbomycin sensitivity | YC-17 and narbomycin sensitivity | 2.9 times more sensitive vs. WT |
| NbnD11 | V33L | narbomycin sensitivity | narbomycin sensitivity | 2.6 times higher activation ratio at 5 uM than WT |
| NbnE1 | A34S | narbomycin sensitivity | narbomycin sensitivity | 2.3 times higher activation ratio at 5 uM than WT |
| NbnG7 | R51C | narbomycin sensitivity | narbomycin sensitivity | 1.7 times higher activation ratio at 5 uM than WT |
| M2D6 | A16T/T154M/ M155K | erythromycin A selectivity versus clarithromycin, azithromycin, and roxithromycin | erythromycin A selectivity versus clarithromycin, azithromycin, and roxithromycin | 20 times less sensitive for clarithromycin. No calculable activation with azithromycin and roxithromycin |
| M2D7 | P4L/W107L/ H193R | erythromycin A selectivity versus erythromycin B | erythromycin A selectivity versus erythromycin B | No calculable activation with erythromycin B |
| C9 | A34S/Y103N/ L189F | erythromycin C selectivity versus erythromycins A and B | erythromycin C selectivity versus erythromycins A and B | 6.8 and 13 times less sensitive to erythromycins A and B versus the WT |
| V66P | V66P | erythromycin A sensitivity | always on as tested | Compared at 100 uM erythromycin |
| V66R | V66R | erythromycin A sensitivity | always off as tested | Compared at 100 uM erythromycin |
| V66G | V66G | erythromycin A sensitivity | ~same activation as wild-type | Compared at 100 uM erythromycin |
| V66I | V66I | erythromycin A sensitivity | always off as tested | Compared at 100 uM erythromycin |
| V66D | V66D | erythromycin A sensitivity | always off as tested | Compared at 100 uM erythromycin |
| M1B10 | T49I/L89V/ D98N/E109D | clarithromycin selectivity versus erythromycin A | clarithromycin selectivity versus erythromycin A | 29.2 and 6.4 times less sensitive to erythromycin A and clarithromycin versus the WT |
| M9C4 | R122T K132N A151T H184Q | clarithromycin selectivity versus erythromycin A | clarithromycin selectivity versus erythromycin A | 45.2 and 6.2 times less sensitive to erythromycin A and clarithromycin versus the WT |
| E7_M9C4 | nt: A4T aa: R122T K132N A151T H184Q | clarithromycin selectivity versus erythromycin A and clarithromycin sensitivity | clarithromycin selectivity versus erythromycin A and clarithromycin sensitivity | 19.4 and 3 times less sensitive to erythromycin A and clarithromycin versus the WT |

Numbering of the nt (nucleotide) mutations corresponds to the ribosome binding site sequence. For example, the RBS sequence for the MphR gene is AGAAGG. Thus, the first A is the "1" position and the final G is the "6" position of the RBS.

Figure 21A:
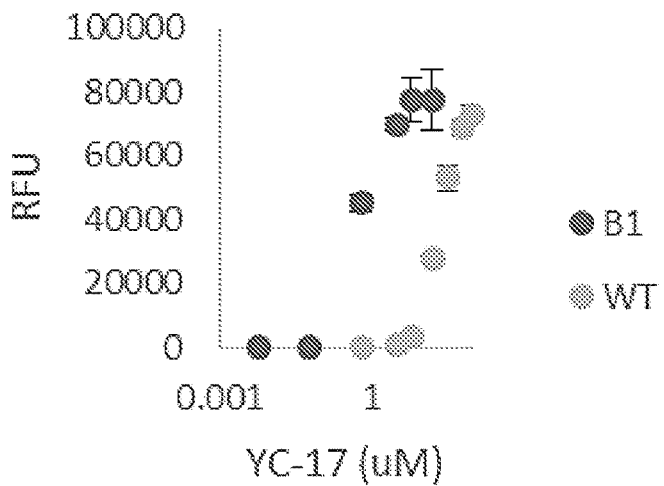
FIGS. 21A-21C. Characterization of YC-17, narbomycin, and pikromycin selective MphR Clones.
Figure 21B:
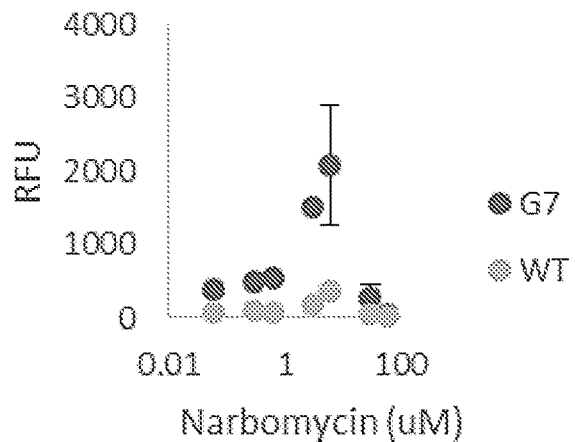
Figure 21C:
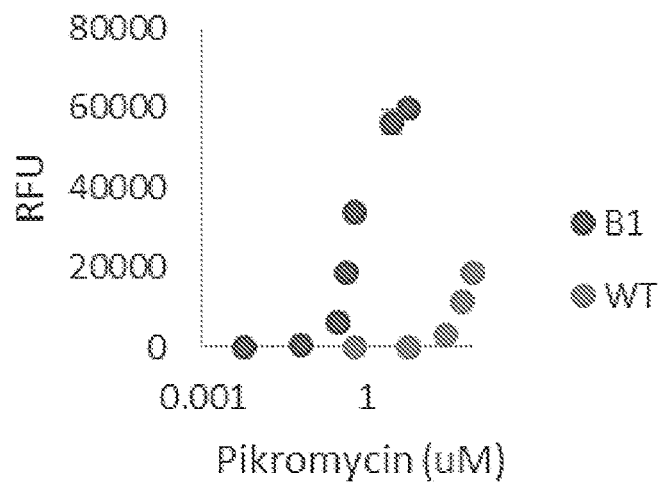

Some of the mutations were further characterized for YC-17, narbomycin, and pikromycin selective MphR clones (FIG. 21; Tables 12-14).

TABLE 12

Selected sensitivity mutants with YC-17

|  | WT | A11 | pikB1 | G11 |
|---|---|---|---|---|
| $K_{1/2}$ | 19.6 ± 0.6 | 2.3 ± 0.1 | 0.49 ± 0.05 | 6.7 ± 0.2 |

TABLE 13

Selected sensitivity mutants with Narbomycin

|  | WT | D11 |
|---|---|---|
| Activation ratio (5 uM/ 0 uM) | 4 | 11 |

TABLE 14

Selected sensitivity mutants with Pikromycin

|  | WT | pikB1 |
|---|---|---|
| $K_{1/2}$ | 96.6 ± 2.7 | 0.81 ± 0.03 |

Example 11

Screening Erythromycin Producing Strains

An erythromycin producing strain, *Aeromicrobium erythreum* (Reeves A R, et al. Engineering precursor flow for increased erythromycin production in *Aeromicrobium erythreum*. *Metabolic Engineering*. 2004; 6(4): 300-12; Miller E S, et al. Description of the erythromycin-producing bacterium *Arthrobacter* sp. strain NRRL B-3381 as *Aeromicrobium erythreum* gen. nov., sp. Nov. *International Journal of Systematic Bacteriology*. 1991; 41: 363-368), and a knock-out mutant (KO) were grown in wells of a 96-well microtiter plate. Culture supernatants were removed and transferred to another microplate that contained cultures of either the MphR mutant E7-RBS or the wild-type biosensor. Fluorescence analysis revealed the unequivocal detection of only those wells containing the producing strain, and demonstrated the superior dynamic range of the engineered vs. wild-type biosensor (FIG. 22).

Figure 22A:
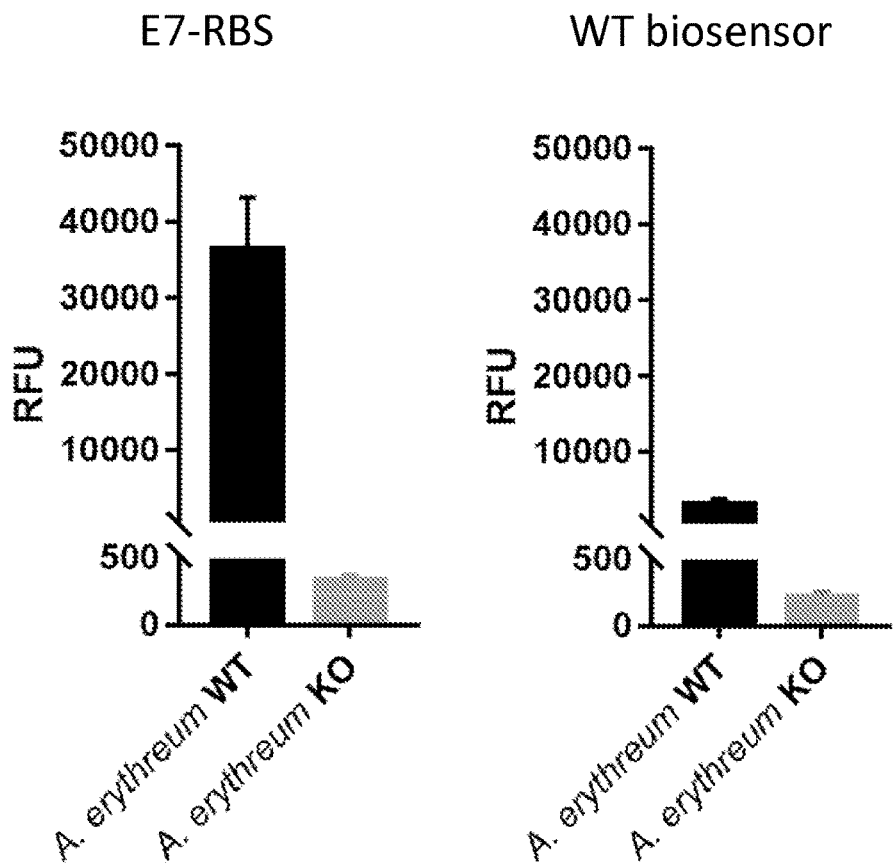
FIG. 22A. The E7-RBS clone shows increased detection of the erythromycin producing strain, *Aeromicrobium erythreum*, compared to the wild-type (WT) biosensor.
Figure 22B:
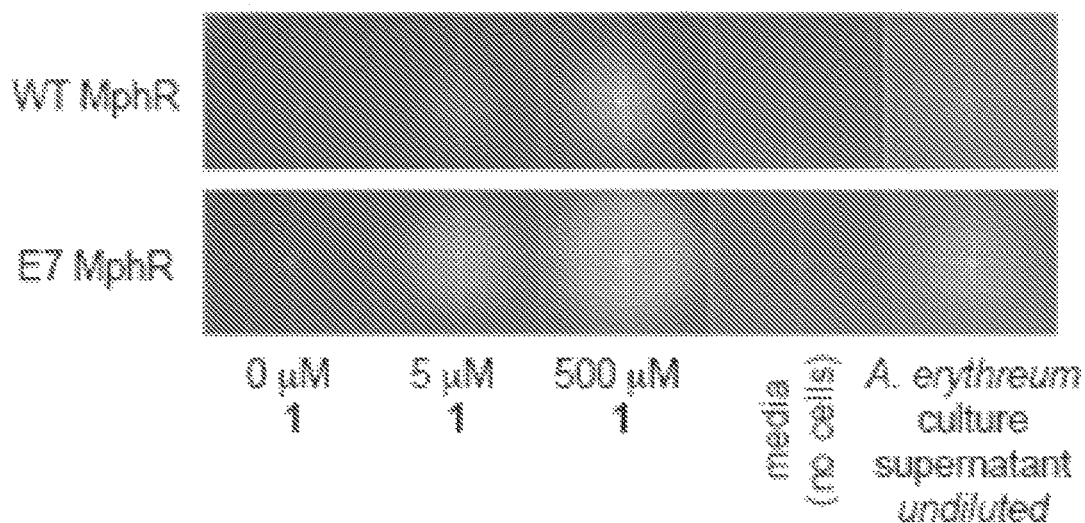
FIG. 22B. Agar plate detection of the E7-RBS clone shows increased detection of the erythromycin producing strain, *Aeromicrobium erythreum*, compared to the WT biosensor.

A similar method using biosensor strains immobilized on agar plates reveals the sensitivity of the engineered biosensor and demonstrates the ability to screen culture collection supernatants in high-throughput via agar plates (FIG. 22).

Example 12

Growth Selection for Erythromycin Producing Strains

Figure 23:
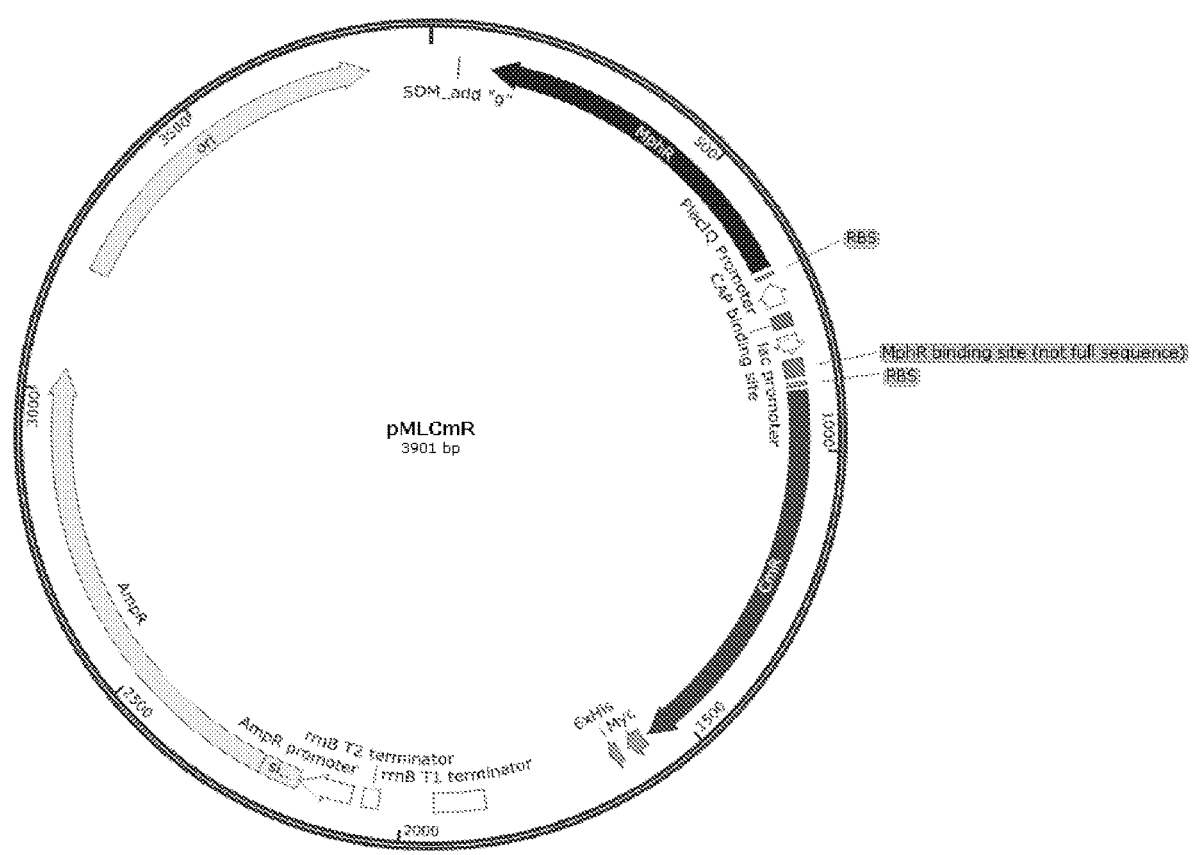
FIG. 23. Plasmid map for WT-pMLCmR.
Figure 24:
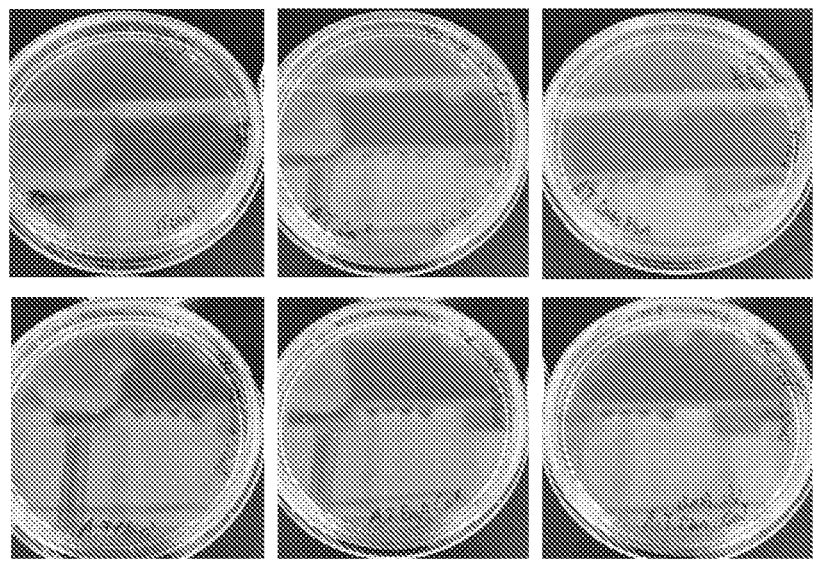
FIG. 24. Analysis of the control of expression of the chloramphenicol (Cm) resistance gene using pMLCmR.

Wild-type (WT) MphR was used to control expression of the chloramphenicol (Cm) resistance gene via the plasmid pMLCmR (FIG. 23). In this way, colonies should only grow in the presence of Cm when clarithromycin or erythromycin A are also provided. The following data indicates that when Cm is provided, colonies grow when erythromycin A (ErA) or clarithromycin are provided (FIG. 24; bottom middle, bottom right), but not in their absence (top middle). Thus, MphR can be used in a growth selection format, significantly expanding the throughput of analysis.

Figure 25:
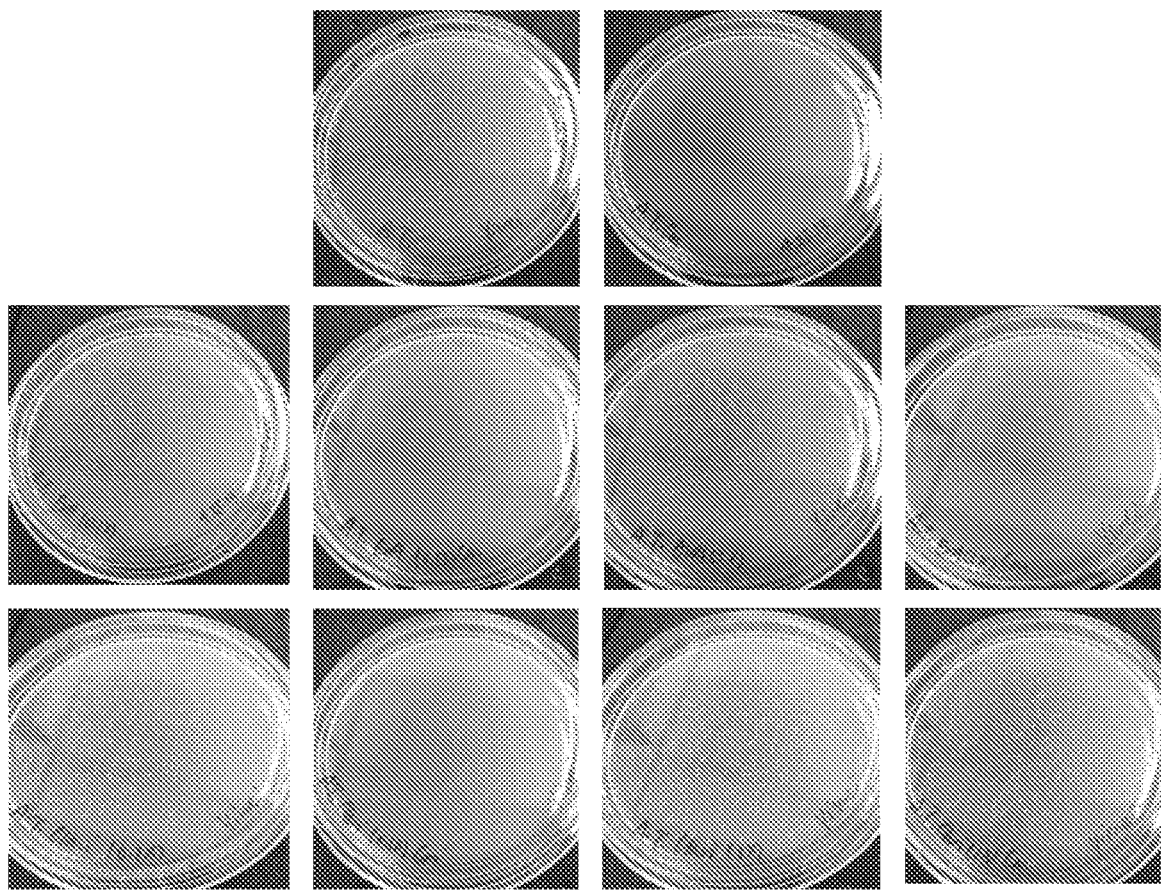
FIG. 25. Analysis of antibiotic sensitivities of the E7-M9C4 pMLCmR clone.

A similar trend was observed when the engineered MphR E7-M9C4 was used in place of the wild-type MphR. However, using this clarithromycin-selective MphR variant, at 5 µM polyketide, colonies grew when clarithromycin was provided but not in the presence of erythromycin, thus highlighting the improved sensitivity of this mutant, in comparison to the wild-type biosensor (FIG. 25). Furthermore, comparison of colony growth at 0.5 µM vs. 5 µM polyketide highlights the expected dose response of the selection system.

SEQUENCES

Provided herein is the gene sequence of the wild-type MphR gene:
DNA sequence-Wild-type MphR
ATGCCCGCCCCAAGCTCAAGTCCGATGACGAGGTACTCGAGGCCGCCAC
CGTAGTGCTGAAGCGTTGCGGTCCCATAGAGTTCACGCTCAGCGGAGTAG
CAAAGGAGGTGGGGCTCTCCCGCGCAGCGTTAATCCAGCGCTTCACCAAC
CGCGATACGCTGCTGGTGAGGATGATGGAGCGCGGCGTCGAGCAGGTGCG
GCATTACCTGAATGCGATACCGATAGGCGCAGGGCCGCAAGGGCTCTGGG
AATTTTTGCAGGTGCTCGTTCGGAGCATGAACACTCGCAACGACTTCTCG
GTGAACTATCTCATCTCCTGGTACGAGCTCCAGGTGCCGGAGCTACGCAC
GCTTGCGATCCAGCGGAACCGCGCGGTGGTGGAGGGGATCCGCAAGCGAC
TGCCCCCAGGTGCTCCTGCGGCAGCTGAGTTGCTCCTGCACTCGGTCATC
GCTGGCGCGACGATGCAGTGGGCCGTCGATCCGGATGGTGAGCTAGCTGA
TCATGTGCTGGCTCAGATCGCTGCCATCCTGTGTTTAATGTTTCCCGAAC
ACGACGATTTCCAACTCCTCCAGGCACATGCGTAA (SEQ ID NO: 1)

Also provided herein is the amino acid sequence of the wild-type MphR protein:
Amino acid sequence-Wild-type MphR
MPRPKLKSDDEVLEAATVVLKRCGPIEFTLSGVAKEVGLSRAALIQRFTN
RDTLLVRMMERGVEQVRHYLNAIPIGAGPQGLWEFLQVLVRSMNTRNDFS
VNYLISWYELQVPELRTLAIQRNRAVVEGIRKRLPPGAPAAAELLLHSVI
AGATMQWAVDPDGELADHVLAQIAAILCLMFPEHDDFQLLQAHA (SEQ ID NO: 2)

Provided herein are the gene sequences of the MphR mutations (see Table 11) (mutated nucleotides are underlined) (the sequences directly below only contain the coding sequences; for additional sequence upstream of ATG, see SEQ ID NO: 28-57).

epA3
ATGCCCCGCCCCAAGCTCAAGTCCGATGACGAGGTACTCGAGGCCGCCAC
CGTAGTGCTGAAGCGTTGCGGTCCCATAGAGTTCACGCTCAGCGGAGTAG
CAAAGGAGGTGGGGCTCTCCCGCGCAGCGTTAATCCAGCGCTTCACCAAC
CGCGATACGCTGCTGGTGAGGATGATGGAGCGCGGCGTCGAGCAGGTGCG
GCATTACCTGAATGCGATACCGATA<u>T</u>GCGCAGGGCCGCAAGGGCTCTGGG
AATTTTTGCAGGTGCTCGTTCGGAGCATGAACACTCGCAACGACTTCTCG
GTGAACTATCTCATCTCCTGGTACGAGCTCCAGGTGCCGGAGCTACGCAC
GCTTGCGATCCAGCGGAACCGCGCGGTGGTGGAGGGGATCCGCAAGCGAC
TGCCCCCAGGTGCTCCTGCGGCAGCTGAGTTGCTCCTGCACTCGGTCATC
GCTGGCGCGACGATGCAGTGGGCCGTCGATCCGGATGGTGAGCTAGCTGA
TCATGTGCTGGCTCAGATCGCTGCCATCCTGTGTTTAATGTTTCCCGAAC
ACGACGATTTCCAACTCCTCCAGGCACATGCGTAA (SEQ ID NO: 3)

epE7
ATGCCCCGCCCCAAGCTCAAGTCCGATGACGAGGTACTCGAGGCCGCCAC
CGTAGTGCTGAAGCGTTGCGGTCCCATAGAGTTCACGCTCAGCGGAGTAG
CAAAGGAGGTGGGGCTCTCCCGCGCAGCGTTAATCCAGCGCTTCACCAAC
CGCGATACGCTGCTGGTGAGGATGATGGAGCGCGGCGTCGAGCAGGTGCG
GCATTACC<u>TT</u>AATGCGATACCGATAGGCGCAGGGCCGCAAGGGCTCTGGG
AATTTTTGCAGGTGCTC<u>A</u>TTCGGAGCATGAACACTCGCAACGACTTCTCG
GTGAACTATCTCATCTCCTGGTACGAGCTCCAGGTGCCGGAGCTACGCAC
GCTTGCGATCCAGCGGAACCGCGCGGTGGTGGAGGGGATCCGCAAGCGAC
TGCCCCCAGGTGCTCCTGCGGCAGCTGAGTTGCTCCTGCACTCGGTCATC
GCTGGCGCGACGATGCAGTGGGCCGTCGATCCGGATGGTGAGCTAGCTGA
TCATGTGCTGGCTCAGATCGCTGCCATCCTGTGTTTAATGTTTCCCGAAC
ACGACGATTTCCAACTCCTCCAGGCACATGCGTAA (SEQ ID NO: 4)

epH4
ATGCCCCGCCCCAAGCTCAAGTCCGATGACGAGGTACTCGAGGCCGCCAC
CGTAGTGCTGAAGC<u>A</u>TTGCGGTCCCATAGAGTTCACGCTCAGCGGAGTAG
CAAATGAGGTGGGGCTCTCCCGCGCAGCGTTAATCCAGCGCTTCACCAAC

| SEQUENCES |
|---|
| CGCGATACGCTGCTGGTGAGGATGATGGAGCGCGGCGTCGAGCAGGTGCG<br>GCATTACCTGAATGCGATACCGATAGGCGCAGGGCCGCAAGGGCTCTGGG<br>AATTTTTGCAGGTGCTCGTTCGGAGCATGAACACTCGCAACGACTTCTCG<br>GTGAACTATCTCATCTC<u>T</u>TGGTACGAGCTCCAGGTGCCGGAGCTACGCAC<br>GCTTGCGATCCAGCGGAACCGCGCGGTGGTGGAGGGGATCCGCAAGCGAC<br>TGCCCCCAGGTGCTCCTGCGGCAGCTGAGTTGCTCCTGCACTCGGTCATC<br>GCTGGCGCGACGATGCAGTGGGCCGTCGATCCGGATGGTGAGCTAGCTGA<br>TCATGTGCTGGCTCAGATCGCTGCCATCCTGTGTTTAATGTTTCCCGAAC<br>ACGACGATTTCCAACTCCTCCAGGCACATGCGTAA (SEQ ID NO: 5)<br><br>QCMS3D6<br>ATGCCCCGCCCCAAGCTCAAGTCCGATGACGAGGTACTCGAGGCCGCCA<u>G</u><br>GGTAGTGCTGAAGCGTTGCGGTCCCATAGAGTTCACGCTCAGCGGAGTAG<br>CAAAGGAGGTGGGGCTCTCCCGCGCAGCGTTAATCCAGCGCTTCACCAAC<br>CGCGATACGCTGCTGGTGAGGATGATGGAGCGCGGCGTCGAGCAGGTGCG<br>GGATTACCTGAATGCGATACCGATAGGCGCAGGGCCGCAAGGGCTCTGGG<br>AATTTTTGCAGGTGCTCGTTCGGAGCATGAACACTCGCAACGACTTCTCG<br>GTGAACTATCTCATCTCCTGGTACGAGCTCCAGGTGCCGGAGCTACGCAC<br>GCTTTGCGATCCAGCGGAACCGCGCGGTGGTGGAGGGGATCCGCAAGCGA<br>CTGCCCCCAGGTGCTCCTGCGGCAGCTGAGTTGCTCCTGCACTCGGTCAT<br>CGCTGGCGCGACGATGCAGTGGGCCGTCGATCCGGATGGTGAGCTAGCTG<br>ATCATGTGCTGGCTCAGATCGCTTGCCATCCTGTGTTTTAATGTTTCCCG<br>AACAc<u>G</u>AcGATTTCCAACTCCTCCAGGCACATGCGTAA (SEQ ID<br>NO: 6)<br><br>QCMS3F8<br>ATGCCCCGCCCCAAGCTCAAGTCCGATGACGAGGTACTCGAGGCCGCC<u>GC</u><br><u>G</u>GTAGTGCTGAAGCGTTGCGGTCCCATAGAGTTCACGCTCAGCGGAGTAG<br>CAAAGGAGGTGGGGCTCTCCCGCGCAGCGTTAATCCAGCGCTTCACCAAC<br>CGCGATACGCTGCTGGTGAGGATGA<u>GT</u>GAGCGCGGCGTCGAGCAGGTGCG<br>GCATTACCTGAATGCGATACCGATAGGCGCAGGGCCGCAAGGGCTCTGGG<br>AATTTTTGCAGGTGCTCGTTCGGAGCATGAACACTCGCAACGACTTCTCG<br>GTGAACTATCTCATCTCCTGGTACGAGCTCCAGGTGCCGGAGCTACGCAC<br>GCTTGCGATCCAGCGGAACCGCGCGGTGGTGGAGGGGATCCGCAAGCGAC<br>TGCCCCCAGGTGCTCCTGCGGCAGCTGAGTTGCTCCTGCACTCGGTCATC<br>GCTGGCGCGACGATGCAGTGGGCCGTCGATCCGGATGGTGAGCTAGCTGA<br>TCATGTGCTGGCTCAGATCGCTGCCATCCTGTGTTTAATGTTTCCCGAAC<br>ACGACGATTTCCAACTCCTCCAGGCACATGCGTAA (SEQ ID NO: 7)<br><br>QCMS5B4<br>ATGCCCCGCCCCAAGCTCAAGTCCGATGACGAGGTACTCGAGGCCGCC<u>GG</u><br><u>T</u>GTAGTGCTGAAGCGTTGCGGTCCCATAGAGTTCACGCTCAGCGGAGTAG<br>CAAAGGAGGTGGGGCTCTCCCGCGCAGCGTTAATCCAGCGCTTCACCAAC<br>CGCGATACGCTGCTGGTGAGGATGATGGAGCGCGGCGTCGAG<u>ATGGTT</u>CG<br>GCATTACCTGAATGCGATACCGATAGGCGCAGGGCCGCAAGGGCTCTGGG<br>AATTTTTGCAGGTGCTCGTTCGGAGCATGAACACTCGCAACGACTTCTCG<br>GTGAACTATCTCATCTCCTGGTACGAGCTCCAGGTGCCGGAGCTACGCAC<br>GCTTGCGATCCAGCGGAACCGCGCGGTGGTGGAGGGGATCCGCAAGCGAC<br>TGCCCCCAGGTGCTCCTGCGGCAGCTGAGTTGCTCCTGCACTCGGTCATC<br>GCTGGCGCGACGATGCAGTGGGCCGTCGATCCGGATGGTGAGCTAGCTGA<br>TCATGTGCTGGCTCAGATCGCTGCCATCCTGTGTTTAATGTTTCCCGAAC<br>A<u>c</u>GACGATTTCCAACTCCTCCAGGCACATGCGTAA (SEQ ID NO: 8)<br><br>QCMS5D7<br>ATGCCCCGCCCCAAGCTCAAGTCCGATGACGAGGTACTCGAGGCCGCC<u>GC</u><br><u>T</u>GTAGTGCTGAAGCGTTGCGGTCCCATAGAGTTCACGCTCAGCGGAGTAG<br>CAAAGGAGGTGGGGCTCTCCCGCGCAGCGTTAATCCAGCGCTTCACCAAC<br>CGCGATACGCTGCTGGTGAGGATG<u>G</u>GAGGAGCGCGGCGTCGAGCAGGTGCG<br>GCATTACCTGAATGCGATACCGATAGGCGCAGGGCCGCAAGGGCTCTGGG<br>AATTTTTGCAGGTGCTCGTTCGGAGCATGAACACTCGCAACGACTTCTCG<br>GTGAACTATCTCATCTCCTGGTACGAGCTCCAGGTGCCGGAGCTACGCAC<br>GCTTGCGATCCAGCGGAACCGCGCGGTGGTGGAGGGGATCCGCAAGCGAC<br>TGCCCCCAGGTGCTCCTGCGGCAGCTGAGTTGCTCCTGCACTCGGTCATC<br>GCTGGCGCGACGATGCAGTGGGCCGTCGATCCGGATGGTGAGCTAGCTGA<br>TCATGTGCTGGCTCAGATCGCTGCCATCCTGTGTTTAATGTTTCCCGAAC<br>ACGACGATTTCCAACTCCTCCAGGCACATGCGTAA (SEQ ID NO: 9)<br><br>D3 (pikB1)<br>ATGCCCCGCCCCAAGCTCAAGTCCGATGACGAGGTACTCGAGGCCGCCAC<br>CGTAGTGCTGAAGCGTTGCGGTCCCATAGAGTTCACGCTCAGCGGAGTAG<br>CAAAGGAGGTGGGGCTCTCCCGCGCAGCGTTAATCCAGCGCTTCACCAAC<br>CGCGATACGCTGCTGGTGAGGATGATGGAGCGCGGCGTCGAGCAGGTGCG<br>GCATTACCTGAATGCGATACCGATAGGCGCAGGGCCGCAAGGGCTCTGGG<br>AATTTTTGCAGGTGCTCGTTCGGAGCATGAACACTCGCAACGACTTCTCG<br>GTGAACTATCTCATCT<u>T</u>CTGGTACGAGCTCCAGGTGCCGGAGCTACGCAC<br>GCTTGCGATCCAGCGGAACCGCGCGGTGGTGGAGGGGATCCGCAAGCGAC<br>TGCCCCCAGGTGCTCCTGCGGCAGCTGAGTTGCTCCTGCACTCGGTCATC |

| SEQUENCES |
|---|
| GCTGGCGCGACGATGCAGTGGGCCGTCGATCCGGATGGTGAGCTAGCTGA<br>TCATGTGCTGGCTCAGATCGCTGCCATCCTGTGTTTAATGTTTCCCGAAC<br>ACGACGATTTCCAACTCCTCCAGGCACATGCGTAA (SEQ ID<br>NO: 10)<br><br>YCA11<br>ATGCCCCGCCCCAAGCTCAAGTCCGATGACGAGGTACTCGAGGCCGCCAC<br>CGTAGTGCTGAAGCGTTGCGGTCCCATAGAGTTCACGCTCAG<u>A</u>GGAGTAG<br>CAAAGGAGGTGGGGCTCTCCCGCGCTGCGTTAATCCAGCGCTTCACCAAC<br>CGCGATACGCTGCTGGTGAGGATGATGGAGCGCGGCGTCGAGCAGGTGCG<br>ACATTACCTGAATGCGATACCGATAGGCGCAGGGCCGCAAGGGCTCTGGG<br>AATTTTTGCAGGTGCTCGTTCGGAGCATGAACACTCGCAACGACTTCTCG<br>GTGAACTATCTCATCTCCTGGTACGAGCTCCAGGTGCCGGAGCTACGCAC<br>GCTTGCGATCCAGCGGAACCGCGCGGTGGTGGAGGGGATCCGCAAGCGAC<br>TGCCCCCAGGTGCTCCTGCGGCAGCTGAGTTGCTCCTGCACTCGGTCATC<br>GCTGGCGCGACGATGCAGTGGGCCGTCGATCCGGATGGTGAGCTAGCTGA<br>TCATGTGCTGGCTCAGATCGCTGCCATCCTGTGTTTAATGTTTCCCGAAC<br>ACGACGATTTCCAACTCCTCCAGGCACATGCGTAA (SEQ ID<br>NO: 11)<br><br>Nbn.YCG11<br>ATGCCCCGCCCCAAGCTCAAGTCCGATGACGAGGTACTCGAGGCCGCCAC<br>CGTAGTGCTGAAGCGTTGCGGTCCCATAGAGTTCACGCTCAGCGGAGTAG<br>CAAAGGAGGTGGGG<u>T</u>TCTCCCGCGCAGCGTTAATCCAGCGCTTCACCAAC<br>CGCGATACGCTGCTGGTGAGGATGATGGAGCGCGGCGTCGAGCAGGTGCG<br>GCATTACCTGAATGCGATACCGATAGGCGCAGGGCCGCAAGGGCTCTGGG<br>AATTT<u>T</u>TGCAGGTGCTCGTTCGGAGCATGAACACTCGCAACGACTTCTCG<br>GTGAACTATCTCATCTCCTGGTACGAGCTCCAGGTGCCGGAGCTACGCAC<br>GCTTGCGATCCAGCGGAACCGCGCGGTGGTGGAGGGGATCCGCAAGCGAC<br>TGCCCCCAGGTGCTCCTGCGGCAGCTGAGTTGCTCCTGCACTCGGTCATC<br>GCTGGCGCGACGATGCAGTGGGCCGTCGATCCGGATGGTGAGCTAGCTGA<br>TCATGTGCTGGCTCAGATCGCTGCCATCCTGTGTTTAATGTTTCCCGAAC<br>ACGACGATTTCCAACTCCTCCAGGCACATGCGTAA (SEQ ID<br>NO: 12)<br><br>NbnD11<br>ATGCCCCGCCCCAAGCTCAAGTCCGATGACGAGGTACTCGAGGCCGCCAC<br>CGTAGTGCTGAAGCGTTGCGGTCCCATAGAGTTCACGCTCAGCGGA<u>C</u>TAG<br>CAAAGGAGGTGGGGCTCTCCCGCGCAGCGTTAATCCAGCGCTTCACCAAC<br>CGCGATACGCTGCTGGTGAGGATGATGGAGCGCGGCGTCGAGCAGGTGCG<br>GCATTACCTGAATGCGATACCGATAGGCGCAGGGCCGCAAGGGCTCTGGG<br>AATTTTTGCAGGTGCTCGTTCGGAGCATGAACACTCGCAACGACTTCTCG<br>GTGAACTATCTCATCTCCTGGTACGAGCTCCAGGTGCCGGAGCTACGCAC<br><u>C</u>CTTGCGATCCAGCGGAACCGCGCGGTGGTGGAGGGGATCCGCAAGCGAC<br>TGCCCCCAGGTGCTCCTGCGGCAGCTGAGTTGCTCCTGCACTCGGTCATC<br>GCTGGCGCGACGATGCAGTGGGCCGTCGATCCGGATGGTGAGCTAGCTGA<br>TCATGTGCTGGCTCAGATC<u>T</u>CTGCCATCCTGTGTTTAATGTTTCCCGAAC<br>ACGACGATTTCCAACTCCTCCAGGCACATGCGTAA (SEQ ID<br>NO: 13)<br><br>NbnE1<br>ATGCCCCGCCCCAAGCTCAAGTCCGATGACGAGGTACTCGAGGCCGCCAC<br>CGTAGTGCTGAAGCGTTGCGGTCCCATT<u>G</u>AGTTCACGCTCAGCGGAGTAT<br>CAAAGGAGGTGGGGCTCTCCCGCGCAGCGTTAATCCAGCGCTTCACCAA<u>T</u><br>CGCGATACGCTGCTGGTGAGGATGATGGAGCGCGGCGTCGAGCAGGTGCG<br>GCATTACCTGAATGCGATACCGATAGGCGCAGGGCCGCAAGGGCTCTGGG<br>AATTTTTGCAGGTGCTCGTTCGGAGCATGAACACTCGCAACGACTTCTCG<br>GTGAACTATCTCATCTCCTGGTACGAGCTCCAGGTGCCGGAGCTACGCAC<br>GCTTGCGATCCAGCGGAACCGCGCGGTGGTGGAGGGGATCCGCAAGCGAC<br>TGCCCCCAGGTGCTCCTGCGGCAGC<u>A</u>GAGTTGCTCCTGCACTCGGTCATC<br>GCTGGCGCGACGATGCAGTGGGCCGTCGATCCGGATGGTGAGCTAGCTGA<br>TCATGTGCTGGCTCAGATCGCTGCCATCCTGTGTTTAATGTTTCCCGAAC<br>ACGACGATTTCCAACTCCTCCAGGCACATGCGTAA (SEQ ID<br>NO: 14)<br><br>NbnG7<br>ATGCCCCGCCCCAAGCTCAAGTCCGATGACGAGGTACTCGAGGCCGCCAC<br>CGTAGTGCTGAAGCGTTGCGGTCCCATAGAGTTCACGCTCAGCGGAGTAG<br>CAAAGGAGGTGGGGCTCTCCCGCGCAGCGTTAATCCAGCGCTTCACCAAC<br><u>T</u>GCGATACGCTGCTGGTGAGGATGATGGAGCGCGGCGTCGAGCAGGTGCG<br>GCATTACCTGAATGCGATACCGATAGGCGCAGGGCCGCAAGGGCTCTGGG<br>AATTTTTGCAGGTGCTCGTTCGGAGCATGAACACTCGCAACGACTTCTCG<br>GTGAACTATCTCATCTCCTGGTACGAGCTCCAGGTGCCGGAGCTACGCAC<br>GCTTGCGATCCAGCGGAACCGCGCGGTGGTGGAGGGGATCCGCAAGCGAC |

TGCCCCCAGGTGCTCCTGCGGCAGCTGAGTTGCTCCTGCACTCGGTCATC
GCTGGCGCGACGATGCAGTGGGCCGTCGATCCGGATGGTGAGCTAGCTGA
TCATGTGCTGGCTCAGATCGCTGCCATCCTGTGTTTAATGTTTCCCGAAC
ACGACGATTTCCAACTCCTCCAGGCACATGCGTAA (SEQ ID
NO: 15)

M2D6
ATGCCCCGCCCCAAGCTCAAGTCCGATGACGAGGTTCTCGAGGCCACCAC
CGTAGTGCTGAAGCGTTGCGGTCCCATAGAGTTCACGCTCAGTGGAGTGG
CAAAGGAGGTGGGGCTCTCCCGCGCAGCGTTAATCCAGCGCTTCACCAAC
CGCGATACGCTGCTGGTGAGGATGATGGAGCGCGGCGTCGAGCAGGTGCG
GCATTACCTGAATGCGATACCGATAGGCGCAGGGCCGCAAGGGCTCTGGG
AATTTTTGCAGGTGCTCGTTCGGAGCATGAACACTCGCAACGACTTCTCG
GTGAACTATCTCATCTCCTGGTACGAGCTCCAGGTGCCGGAGCTACGCAC
GCTTGCGATCCAGCGGAACCGCGCGGTAGTGGAGGGGATCCGCAAGCGAC
TGCCCCCAGGTGCTCCTGCGGCAGCTGAGTTGCTCCTGCACTCGGTCATC
GCTGGCGCGATGAAGCAGTGGGCCGTCGATCCGGATGGTGAGCTAGCTGA
TCATGTGCTGGCTCAGATCGCTGCCATCCTGTGTTTAATGTTTCCCGAAC
ACGACGATTTCCAACTCCTCCAGGCACATGCGTAA (SEQ ID
NO: 16)

M2D7
ATGCCCCGCCTCAAGCTCAAGTCCGATGACGAGGTACTCGAGGCCGCCAC
CGTAGTGCTGAAGCGTTGCGGTCCCATAGAGTTCACGCTCAGCGGAGTAG
CAAAGGAGGTGGGGCTCTCCCGCGCAGCGTTAATCCAGCGCTTCACCAAC
CGCGATACGCTGCTGGTGAGGATGATGGAGCGCGGCGTCGAGCAGGTGCG
GCATTACCTGAATGCGATACCGATAGGCGCAGGGCCGCAAGGGCTCTGGG
AATTTTTGCAGGTGCTCGTTCGGAGCATGAACACTCGCAACGACTTCTCG
GTGAACTATCTCATCTCCTTGTACGAGCTCCAGGTGCCGAGCTACGCAC
GCTTGCGATCCAGCGGAACCGCGCGGTGGTGAGGGGATCCGCAAGCGAC
TGCCCCCAGGTGCTCCTGCGGCAGCTGAGTTGCTCCTGCACTCGGTCATC
GCTGGCGCGACGATGCAGTGGGCCGTCGATCCGGATGGTGAGCTAGCTGA
TCATGTGCTGGCTCAGATCGCTGCCATCCTGTGTTTAATGTTTCCCGAAC
ACGACGATTTCCAACTCCTCCAGGCACGTGCGTAA (SEQ ID
NO: 17)

C9
ATGCCCCGCCCCAAGCTCAAGTCCGATGACGAGGTACTCGAGGCCGCCAC
CGTAGTGCTGAAGCGTTGCGGTCCCATAGAGTTCACGCTCAGCGGAGTAT
CAAAGGAGGTGGGGCTCTCCCGCGCAGCGTTAATCCAGCGCTTCACCAAC
CGCGATACGCTGCTGGTGAGGATGATGGAGCGCGGCGTCGAGCAGGTGCG
GCATTACCTGAATGCGATACCGATAGGCGCAGGGCCGCAAGGGCTCTGGG
AATTTTTGCAGGTGCTCGTTCGGAGCATGAACACTCGCAACGACTTCTCG
GTGAACAATCTCATCTCCTGGTACGAGCTCCAGGTGCCGGAGCTACGCAC
GCTTGCGATCCAGCGGAACCGCGGTGGTGGAGGGGATCCGCAAGCGAC
TGCCCCCAGGTGCTCCTGCGGCAGCTGAGTTGCTCCTGCACTCGGTCATC
GCTGGCGCGACGATGCAGTGGGCCGTCGATCCGGATGGTGAGCTAGCTGA
TCATGTGCTGGCTCAGATCGCTGCCATCCTGTGTTTAATGTTTCCCGAAC
ACGACGATTTCCAATTCCTCCAGGCACATGCGTAA (SEQ ID
NO: 18)

V66P
ATGCCCCGCCCCAAGCTCAAGTCCGATGACGAGGTACTCGAGGCCGCCAC
CGTAGTGCTGAAGCGTTGCGGTCCCATAGAGTTCACGCTCAGCGGAGTAG
CAAAGGAGGTGGGGCTCTCCCGCGCAGCGTTAATCCAGCGCTTCACCAAC
CGCGATACGCTGCTGGTGAGGATGATGGAGCGCGGCGTCGAGCAGCCACG
GCATTACCTGAATGCGATACCGATAGGCGCAGGGCCGCAAGGGCTCTGGG
AATTTTTGCAGGTGCTCGTTCGGAGCATGAACACTCGCAACGACTTCTCG
GTGAACTATCTCATCTCCTGGTACGAGCTCCAGGTGCCGGAGCTACGCAC
GCTTGCGATCCAGCGGAACCGCGCGGTGGTGAGGGGATCCGCAAGCGAC
TGCCCCCAGGTGCTCCTGCGGCAGCTGAGTTGCTCCTGCACTCGGTCATC
GCTGGCGCGACGATGCAGTGGGCCGTCGATCCGGATGGTGAGCTAGCTGA
TCATGTGCTGGCTCAGATCGCTGCCATCCTGTGTTTAATGTTTCCCGAAC
ACGACGATTTCCAACTCCTCCAGGCACATGCGTAA (SEQ ID
NO: 19)

V66R
ATGCCCCGCCCCAAGCTCAAGTCCGATGACGAGGTACTCGAGGCCGCCAC
CGTAGTGCTGAAGCGTTGCGGTCCCATAGAGTTCACGCTCAGCGGAGTAG
CAAAGGAGGTGGGGCTCTCCCGCGCAGCGTTAATCCAGCGCTTCACCAAC
CGCGATACGCTGCTGGTGAGGATGATGGAGCGCGGCGTCGAGCAGAGGCG
GCATTACCTGAATGCGATACCGATAGGCGCAGGGCCGCAAGGGCTCTGGG
AATTTTTGCAGGTGCTCGTTCGGAGCATGAACACTCGCAACGACTTCTCG
GTGAACTATCTCATCTCCTGGTACGAGCTCCAGGTGCCGGAGCTACGCAC
GCTTGCGATCCAGCGGAACCGCGCGGTGGTGAGGGGATCCGCAAGCGAC
TGCCCCCAGGTGCTCCTGCGGCAGCTGAGTTGCTCCTGCACTCGGTCATC
GCTGGCGCGACGATGCAGTGGGCCGTCGATCCGGATGGTGAGCTAGCTGA
TCATGTGCTGGCTCAGATCGCTGCCATCCTGTGTTTAATGTTTCCCGAAC
ACGACGATTTCCAACTCCTCCAGGCACATGCGTAA (SEQ ID
NO: 20)

V66G
ATGCCCCGCCCCAAGCTCAAGTCCGATGACGAGGTACTCGAGGCCGCCAC
CGTAGTGCTGAAGCGTTGCGGTCCCATAGAGTTCACGCTCAGCGGAGTAG
CAAAGGAGGTGGGGCTCTCCCGCGCAGCGTTAATCCAGCGCTTCACCAAC
CGCGATACGCTGCTGGTGAGGATGATGGAGCGCGGCGTCGAGCAGGGACG
GCATTACCTGAATGCGATACCGATAGCGCAGGGCCGCAAGGGCTCTGGG
AATTTTTGCAGGTGCTCGTTCGGAGCATGAACACTCGCAACACTTCTCG
GTGAACTATCTCATCTCCTGGTACGAGCTCCAGGTGCCGGAGCTACGCAC
GCTTGCGATCCAGCGGAACCGCGCGGTGGTGGAGGGGATCCGCAAGCGAC
TGCCCCCAGGTGCTCCTGCGGCAGCTGAGTTGCTCCTGCACTCGGTCATC
GCTGGCGCGACGATGCAGTGGGCCGTCGATCCGGATGGTGAGCTAGCTGA
TCATGTGCTGGCTCAGATCGCTGCCATCCTGTGTTTAATGTTTCCCGAAC
ACGACGATTTCCAACTCCTCCAGGCACATGCGTAA (SEQ ID
NO: 21)

V66I
ATGCCCCGCCCCAAGCTCAAGTCCGATGACGAGGTACTCGAGGCCGCCAC
CGTAGTGCTGAAGCGTTGCGGTCCCATAGAGTTCACGCTCAGCGGAGTAG
CAAAGGAGGTGGGGCTCTCCCGCGCAGCGTTAATCCAGCGCTTCACCAAC
CGCGATACGCTGCTGGTGAGGATGATGGAGCGCGGCGTCGAGCAGATCCG
GCATTACCTGAATGCGATACCGATAGGCGCAGGGCCGCAAGGGCTCTGGG
AATTTTTGCAGGTGCTCGTTCGGAGCATGAACACTCGCAACGACTTCTCG
GTGAACTATCTCATCTCCTGGTACGAGCTCCAGGTGCCGGAGCTACGCAC
GCTTGCGATCCAGCGGAACCGCGCGGTGGTGAGGGGATCCGCAAGCGAC
TGCCCCCAGGTGCTCCTGCGGCAGCTGAGTTGCTCCTGCACTCGGTCATC
GCTGGCGCGACGATGCAGTGGGCCGTCGATCCGGATGGTGAGCTAGCTGA
TCATGTGCTGGCTCAGATCGCTGCCATCCTGTGTTTAATGTTTCCCGAAC
ACGACGATTTCCAACTCCTCCAGGCACATGCGTAA (SEQ ID
NO: 22)

V66D
ATGCCCCGCCCCAAGCTCAAGTCCGATGACGAGGTACTCGAGGCCGCCAC
CGTAGTGCTGAAGCGTTGCGGTCCCATAGAGTTCACGCTCAGCGGAGTAG
CAAAGGAGGTGGGGCTCTCCCGCGCAGCGTTAATCCAGCGCTTCACCAAC
CGCGATACGCTGCTGGTGAGGATGATGGAGCGCGGCGTCGAGCAGGACCG
GCATTACCTGAATGCGATACCGATAGGCGCAGGGCCGCAAGGGCTCTGGG
AATTTTTGCAGGTGCTCGTTCGGAGCATGAACACTCGCAACGACTTCTCG
GTGAACTATCTCATCTCCTGGTACGAGCTCCAGGTGCCGGAGCTACGCAC
GCTTGCGATCCAGCGGAACCGCGCGGTGGTGAGGGGATCCGCAAGCGAC
TGCCCCCAGGTGCTCCTGCGGCAGCTGAGTTGCTCCTGCACTCGGTCATC
GCTGGCGCGACGATGCAGTGGGCCGTCGATCCGGATGGTGAGCTAGCTGA
TCATGTGCTGGCTCAGATCGCTGCCATCCTGTGTTTAATGTTTCCCGAAC
ACGACGATTTCCAACTCCTCCAGGCACATGCGTAA (SEQ ID
NO: 23)

M1B10
ATGCCCCGCCCCAAGCTCAAGTCCGATGACGAGGTACTCGAGGCCGCCAC
CGTAGTGCTGAAGCGTTGCGGTCCCATAGAGTTCACGCTCAGCGGAGTAG
CAAAGGAGGTGGGGCTCTCCCGCGCAGCGTTAATCCAGCGCTTCATCAAC
CGCGATACGCTGCTGGTGAGGATGATGGAGCGCGGCGTCGAGCAGGTGCG
GCATTACCTGAATGCGATACCGATAGGCGCAGGGCCGCAAGGGCTCTGGG
AATTTTTGCAGGTGTTCGTTCGGAGCATGAACACTCGCAACAACTTCTCG
GTGAACTATCTCATCTCCTGGTACGATCTCCAGGTGCCGGAGCTACGCAC
GCTTGCGATCCAGCGGAACCGCGCGGTGGTGAGGGGATCCGCAAGCGAC
TGCCCCCAGGTGCTCCTGCGGCAGCTGAGTTGCTCCTGCACTCGGTCATC
GCTGGCGCGACGATGCAGTGGGCCGTCGATCCGGATGGTGAGCTAGCTGA
TCATGTGCTGGCTCAGATCGCTGCCATCCTGTGTTTAATGTTTCCCGAAC
ACGACGATTTCCAACTCCTCCAGGCACATGCGTAA (SEQ ID
NO: 24)

M9C4
ATGCCCCGCCCCAAGCTCAAGTCCGATGACGAGGTACTCGAGGCCGCCAC
CGTAGTGCTGAAGCGTTGCGGTCCCATAGAGTTCACGCTCAGCGGAGTAG
CAAAGGAGGTGGGACTCTCCCGCGCAGCGTTAATCCAGCGCTTCACCAAC
CGCGATACGCTGCTGGTGAGGATGATGGAGCGCGGCGTCGAGCAGGTGCG
GCATTACCTGAATGCGATACCGATAGGCGCAGGGCCGCAAGGGCTCTGGG
AATTTTTGCAGGTGCTCGTTCGGAGCATGAACACTCGCAACGACTTCTCG
GTGAACTATCTCATCTCCTGGTACGAGCTCCAGGTGCCGGAGCTACGCAC
GCTTGCGATCCAGACTAACCGCGCGGTGGTGAGGGGATCCGCAATCGAC
TGCCCCCAGGTGCTCCTGCGGCAGCTGAGTTGCTCCTGCACTCGGTCATC

SEQUENCES

ACTGGCGCGACGATGCAGTGGGCCGTCGATCCGGATGGTGAGCTAGCTGA
TCATGTGCTGGCTCAGATCGCTGCCATCCTGTGTTTAATGTTTCCCGAAC
A<u>A</u>GACGATTTCCAACTCCTCCAGGCACATGCGTAA (SEQ ID
NO: 58)

E7_M9C4
ATGCCCCGCCCCAAGCTCAAGTCCGATGACGAGGTACTCGAGGCCGCCAC
CGTAGTGCTGAAGCGTTGCGGTCCCATAGAGTTCACGCTCAGCGGAGTAG
CAAAGGAGGTGGG<u>A</u>CTCTCCCGCGCAGCGTTAATCCAGCGCTTCACCAAC
CGCGATACGCTGCTGGTGAGGATGATGGAGCGCGGCGTCGAGCAGGTGCG
GCATTACCTGAATGCGATACCGATAGGCGCAGGGCCGCAAGGGCTCTGGG
AATTTTTGCAGGTGCTCGTTCGGAGCATGAACACTCGCAACGACTTCTCG
GTGAACTATCTCATCTCCTGGTACGAGCTCCAGGTGCCGGAGCTACCAC
GCTTGCGATCCAG<u>A</u>CTAACCGCGGTGGTGGAGGGGATCCGCAA<u>T</u>CGAC
TGCCCCCAGGTGCTCCTGCGGCAGCTGAGTTGCTCCTGCACTCGGTCATC
A<u>A</u>CTGGCGCGACGATGCAGTGGGCCGTCGATCCGGATGGTGAGCTAGCTGA
TCATGTGCTGGCTCAGATCGCTGCCATCCTGTGTTTAATGTTTCCCGAAC
A<u>A</u>GACGATTTCCAACTCCTCCAGGCACATGCGTAA (SEQ ID
NO: 59)

Provided herein are the nucleic acid sequences for the plasmid vectors disclosed above:

Plasmid pMLGFP:
LOCUS           pMLGFP  3957bp  DNA  circular
SOURCE
  ORGANISM
COMMENT         This file is created by Vector NTI
                http://www.informaxinc.com/
COMMENT         VNTDATE|493119689|
COMMENT         VNTDBDATE|508971571|
COMMENT         VNTNAME|pMLGFP|
COMMENT         VNTAUTHORNAME|zh|
FEATURES             Location/Qualifiers
  misc_feature       1796..1953
                   /vntifkey="21"
                   /label=Terminator
  CDS                2233..3093
                   /vntifkey="4"
                   /label=Amp
  rep_origin         3238..3911
                   /vntifkey="33"
                   /label=pBR322\ori
  CDS                complement(103..687)
                   /vntifkey="4"
                   /label=MphR
  promoter           complement(716..752)
                   /vntifkey="30"
                   /label=PlacIQ
  RBS                697..702
                   /vntifkey="32"
                   /label=RBS
  promoter           759..842
                   /vntifkey="30"
                   /label=lac\promoter
  promoter           843..880
                   /vntifkey="30"
                   /label=PmphR
  CDS                901..1617
                   /vntifkey="4"
                   /label=GFP
  RBS                887..892
                   /vntifkey="32"
                   /label=RBS
BASE COUNT         1017 a   972 c   992 g   976 t
ORIGIN (SEQ ID NO: 25)

```
   1 tctagtgtac agtgatcaag acttcgatac caccgaccgt accggtacta atcgacgacg
  61 gtcgtgttcg tcgcctgccg cagggactct gcacacctcc gtttacgcat gtgcctggag
 121 gagttggaaa tcgtcgtgtt cgggaaacat taaacacagg atggcagcga tctgagccag
 181 cacatgatca gctagctcac catccggatc gacggcccac tgcatcgtcg cgccagcgat
 241 gaccgagtgc aggagcaact cagctgccgc aggagcacct gggggcagtc gcttgcggat
 301 cccctccacc accgcgcggt tccgctggat cgcaagcgtg cgtagctccg gcacctggag
 361 ctcgtaccag gagatgagat agttcaccga gaagtcgttg cgagtgttca tgctccgaac
 421 gagcacctgc aaaaattccc agagcccttg cggccctgcg cctatcggta tcgcattcag
 481 gtaatgccgc acctgctcga cgccgcgctc catcatcctc accagcagcg tatcgcggtt
 541 ggtgaagcgc tggattaacg ctgcgcggga gagccccacc tcctttgcta ctccgctgag
 601 cgtgaactct atgggaccgc aacgcttcag cactacggtg gcggcctcga gtacctcgtc
 661 atcggacttg agcttggggc ggggcatcag tgttcacctt ctgtatgggt tgggggcgc
 721 tatcatgcca taccgcgaaa ggttttgcac catctagagc gcaacgcaat taatgtgagt
 781 tagctcactc attaggcacc ccaggcttta cactttatgc ttccggctcg tatgttgtgt
 841 gggattgaat ataaccgacg tgactgttac atttaggtgg gctaacagga ggaaactagt
 901 atgagtaaag gagaagaact tttcactgga gttgtcccaa ttcttgttga attagatggt
 961 gatgttaatg ggcacaaatt ttctgtcagt ggagagggtg aaggtgatgc aacatacgga
1021 aaacttaccc ttaaatttat ttgcactact ggaaaactac ctgttccatg gccaacactt
1081 gtcactactt tctcttatgg tgttcaatgc ttttcccgtt atccggatca tatgaaacgg
```

-continued

```
1141  catgactttt tcaagagtgc catgcccgaa ggttatgtac aggaacgcac tatatctttc
1201  aaagatgacg ggaactacaa gacgcgtgct gaagtcaagt tgaaggtga taccccttgtt
1261  aatcgtatcg agttaaaagg tattgatttt aaagaagatg gaaacattct cggacacaaa
1321  ctcgagtaca actataactc acacaatgta tacatcacg cagacaaaca aaagaatgga
1381  atcaaagcta acttcaaaat tcgccacaac attgaagatg gatccgttca actagcagac
1441  cattatcaac aaaatactcc aattggcgat ggccctgtcc ttttaccaga caaccattac
1501  ctgtcgacac aatctgccct ttcgaaagat cccaacgaaa agcgtgacca catggtcctt
1561  cttgagtttg taactgctgc tgggattaca catggcatgg atgagctcta caaataagct
1621  tgggcccgaa caaaaactca tctcagaaga ggatctgaat agcgccgtcg accatcatca
1681  tcatcatcat tgagtttaaa cggtctccag cttggctgtt ttggcggatg agagaagatt
1741  ttcagcctga tacagattaa atcagaacgc agaagcggtc tgataaaaca gaatttgcct
1801  ggcggcagta gcgcggtggt cccacctgac ccatgccga actcagaagt gaaacgccgt
1861  agcgccgatg gtagtgtggg gtctccccat gcgagagtag ggaactgcca ggcatcaaat
1921  aaaacgaaag gctcagtcga aagactgggc ctttcgtttt atctgttgtt tgtcggtgaa
1981  cgctctcctg agtaggacaa atccgccggg agcggatttg aacgttgcga agcaacggcc
2041  cggagggtgg cgggcaggac gcccgccata aactgccagg catcaaatta agcagaaggc
2101  catcctgacg gatggccttt ttgcgtttct acaaactctt tttgtttatt tttctaaata
2161  cattcaaata tgtatccgct catgagacaa taaccctgat aaatgcttca ataatattga
2221  aaaaggaaga gtatgagtat tcaacatttc cgtgtcgccc ttattccctt ttttgcggca
2281  ttttgccttc ctgtttttgc tcacccagaa acgctggtga agtaaaaga tgctgaagat
2341  cagttgggtg cacgagtggg ttacatcgaa ctggatctca acagcggtaa gatccttgag
2401  agttttcgcc ccgaagaacg ttttccaatg atgagcactt ttaaagttct gctatgtggc
2461  gcggtattat cccgtgttga cgccgggcaa gagcaactcg gtcgccgcat acactattct
2521  cagaatgact tggttgagta ctcaccagtc acagaaaagc atcttacgga tggcatgaca
2581  gtaagagaat tatgcagtgc tgccataacc atgagtgata acactgcggc caacttactt
2641  ctgacaacga tcggaggacc gaaggagcta accgcttttt tgcacaacat ggggatcat
2701  gtaactcgcc ttgatcgttg ggaaccggag ctgaatgaag ccataccaaa cgacgagcgt
2761  gacaccacga tgcctgtagc aatggcaaca acgttgcgca aactattaac tggcgaacta
2821  cttactctag cttcccggca acaattaata gactggatgg aggcggataa agttgcagga
2881  ccacttctgc gctcggccct tccggctggc tggtttattg ctgataaatc tggagccggt
2941  gagcgtgggt ctcgcggtat cattgcagca ctggggccag atggtaagcc ctcccgtatc
3001  gtagttatct acacgacggg gagtcaggca actatggatg aacgaaatag acagatcgct
3061  gagataggtg cctcactgat taagcattgg taactgtcag accaagttta ctcatatata
3121  ctttagattg atttaaaact tcattttaa tttaaaagga tctaggtgaa gatcctttt
3181  gataatctca tgaccaaaat cccttaacgt gagttttcgt tccactgagc gtcagacccc
3241  gtagaaaaga tcaaaggatc ttcttgagat cctttttttc tgcgcgtaat ctgctgcttg
3301  caaacaaaaa aaccaccgct accagcggtg gtttgtttgc cggatcaaga gctaccaact
3361  cttttccga aggtaactgg cttcagcaga gcgcagatac caaatactgt ccttctagtg
3421  tagccgtagt taggccacca cttcaagaac tctgtagcac cgcctacata cctcgctctg
3481  ctaatcctgt taccagtggc tgctgccagt ggcgataagt cgtgtcttac cgggttggac
3541  tcaagacgat agttaccgga taaggcgcag cggtcgggct gaacggggggg ttcgtgcaca
```

-continued

```
3601  cagcccagct tggagcgaac gacctacacc gaactgagat acctacagcg tgagctatga
3661  gaaagcgcca cgcttcccga agggagaaag gcggacaggt atccggtaag cggcagggtc
3721  ggaacaggag agcgcacgag ggagcttcca gggggaaacg cctggtatct ttatagtcct
3781  gtcgggtttc gccacctctg acttgagcgt cgatttttgt gatgctcgtc agggggggcgg
3841  agcctatgga aaaacgccag caacgcggcc ttttacggt tcctggcctt ttgctggcct
3901  tttgctcaca tgttctttcc tgcgttatcc cctgattctg tggataaccg tattacc
```

Plasmid pJZ12:
LOCUS           pJZ12    5131 bp   DNA   circular
SOURCE
  ORGANISM
COMMENT         This file is created by Vector NTI
                http://www.informaxinc.com/
COMMENT         VNTDATE|493491327|
COMMENT         VNTDBDATE|508971571|
COMMENT         VNTNAME|pJZ12|
COMMENT         VNTAUTHORNAME|zhl|
FEATURES        Location/Qualifiers
     CDS        582..1772
                /vntifkey="4"
                /label=TetR -continued rep_origin  4713..412
                 /vntifkey="33"
                 /label=rep(p15A)
     CDS         2945..3850
                 /vntifkey="4"
                 /label=mphA
     CDS         3847..4649
                 /vntifkey="4"
                 /label=mrx\incomplete\CDS
BASE COUNT   980 a   1521 c   1515 g   11151 t
ORIGIN (SEQ ID NO: 26)
```
   1  tcattccgct gttatggccg cgtttgtctc attccacgcc tgacactcag ttccgggtag
  61  gcagttcgct ccaagctgga ctgtatgcac gaaccccccg ttcagtccga ccgctgcgcc
 121  ttatccggta actatcgtct tgagtccaac ccggaaagac atgcaaaagc accactggca
 181  gcagccactg gtaattgatt tagaggagtt agtcttgaag tcatgcgccg gttaaggcta
 241  aactgaaagg acaagttttg gtgactgcgc tcctccaagc cagttacctc ggttcaaaga
 301  gttggtagct cagagaacct tcgaaaaacc gccctgcaag gggttttttt cgttttcaga
 361  gcaagagatt acgcgcagac caaaacgatc tcaagaagat catcttatta atcagataaa
 421  atatttctag atttcagtgc aatttatctc ttcaaatgta gcacctgaag tcagccccat
 481  acgatataag ttgtaattct catgtttgac agcttatcat cgataagctt taatgcggta
 541  gtttatcaca gttaaattgc taacgcagtc aggcaccgtg tatgaaatct aacaatgcgc
 601  tcatcgtcat cctcggcacc gtcaccctgg atgctgtagg cataggcttg gttatgccgg
 661  tactgccggg cctcttgcgg gatatcgtcc attccgacag catcgccagt cactatggcg
 721  tgctgctagc gctatatgcg ttgatgcaat ttctatgcgc acccgttctc ggagcactgt
 781  ccgaccgctt tggccgccgc ccagtcctgc tcgcttcgct acttggagcc actatcgact
 841  acgcgatcat ggcgaccaca cccgtcctgt ggatcctcta cgccggacgc atcgtggccg
 901  gcatcaccgg cgccacaggt gcggttgctg gcgcctatat cgccgacatc accgatgggg
 961  aagatcgggc tcgccacttc gggctcatga gcgcttgttt cggcgtgggt atggtggcag
1021  gccccgtggc cgggggactg ttgggcgcca tctccttgca tgcaccattc cttgcgcgg
1081  cggtgctcaa cggcctcaac ctactactgg gctgcttcct aatgcaggag tcgcataagg
1141  gagagcgtcg accgatgccc ttgagagcct tcaacccagt cagctccttc cggtgggcgc
1201  ggggcatgac tatcgtcgcc gcacttatga ctgtcttctt tatcatgcaa ctcgtaggac
1261  aggtgccgga gcgctctggt caattttcg gcgaggaccg ctttcgctgg agcgcgacga
1321  tgatcggcct gtcgcttgcg gtattcggaa tcttgcacgc cctcgctcaa gccttcgtca
1381  ctggtcccgc caccaaacgt ttcggcgaga agcaggccat tatcgccggc atggcggccg -continued

```
1441  acgcgctggg ctacgtcttg ctggcgttcg cgacgcgagg ctggatggcc ttccccatta
1501  tgattcttct cgcttccggc ggcatcggga tgcccgcgtt gcaggccatg ctgtccaggc
1561  aggtagatga cgaccatcag ggacagcttc aaggatcgct cgcggctctt accagcctaa
1621  cttcgatcac tggaccgctg atcgtcacgg cgatttatgc cgcctcggcg agcacatgga
1681  acgggttggc atggattgta ggcgccgccc tataccttgt ctgcctcccc gcgttgcgtc
1741  gcggtgcatg gagccgggcc acctcgacct gaatggaagc cggcggcacc tcgctaacgg
1801  attcaccact ccaagaattg gagccaatca attcttgcgg agaactgtga atgcgcaaac
1861  caaccccttgg cagaacatat ccatcgcgtc cgccatctcc agcagccgca cgcggcgcat
1921  ctcgggcagc gttgggtcct ggccacgggt gcgcatgatc gtgctcctgt cgttgaggac
1981  ccggctaggc tggcggggtt gccttactgg ttagcagaat gaatcaccga tacgcgagcg
2041  aacgtgaagc gactgctgct gcaaaacgtc tgcgacctga gcaacaacat gaatggtctt
2101  cggtttccgt gtttcgtaaa gtctggaaac gcggaagtcc cctacgtgct gctgaagttg
2161  cccgcaacag agagtggaac cggtacccgg ggatcctcta gagtcgacct gcaggagatg
2221  ctggctgaac gcggagtgaa tgtcgatcac tccacgattt accgctgggt tcagcgttat
2281  gcgcctgaaa tggaaaaacg gctgcgctgg tactggcgta acccttccga tctttgcccg
2341  tggcacatgg atgaaaccta cgtgaaggtc aatggccgct gggcgtatct gtaccgggcc
2401  gtcgacagcc ggggccgcac tgtcgatttt tatctctcct cccgtcgtaa cagcaaagct
2461  gcataccggt ttctgggtaa aatcctcaac aacgtgaaga agtggcagat cccgcgattc
2521  atcaacacgg ataaagcgcc cgcctatggt cgcgcgcttg ctctgctcaa acgcgaaggc
2581  cggtgcccgt ctgacgttga acaccgacag attaagtacc ggaacaacgt gattgaatgc
2641  gatcatggca aactgaaacg gataatcggc gccacgctgg gatttaaatc catgaagacg
2701  gcttacgcca ccatcaaagg tattgaggtg atgcgtgcac tacgcaaagg ccaggcctca
2761  gcattttatt atggtgatcc cctgggcgaa atgcgcctgg taagcagagt ttttgaaatg
2821  taaggccttt gaataagaca aaaggctgcc tcatcgctaa ctttgcaaca gtgccggatt
2881  gaatataacc gacgtgactg ttacatttag gtggctaaac ccgtcaagcc ctcaggagtg
2941  aatcatgacc gtagtcacga ccgccgatac ctcccaactg tacgcacttg cagcccgaca
3001  tgggctcaag ctccatggcc cgctgactgt caatgagctt gggctcgact ataggatcgt
3061  gatcgccacc gtcgacgatg gacgtcggtg ggtgctgcgc atcccgcgcc gagccgaggt
3121  aagcgcgaag gtcgaaccag aggcgcgggt gctggcaatg ctcaagaatc gcctgccgtt
3181  cgcggtgccg gactggcgcg tggccaacgc cgagctcgtt gcctatccca tgctcgaaga
3241  ctcgactgcg atggtcatcc agcctggttc gtccacgccc gactgggtcg tgccgcagga
3301  ctcggaggtc ttcgcggaga gcttcgcgac cgcgctcgcc gccctgcatg ccgtccccat
3361  ttccgccgcc gtggatgcgg ggatgctcat ccgtacaccg acgcaggccc gtcagaaggt
3421  ggccgacgac gttgaccgcg tccgacgcga gttcgtggtg aacgacaagc gcctccaccg
3481  gtggcagcgc tggctcgacg acgattcgtc gtggccagat ttctccgtgg tggtgcatgg
3541  cgatctctac gtgggccatg tgctcatcga caacacggag cgcgtcagcg ggatgatcga
3601  ctggagcgag gcccgcgttg atgaccctgc catcgacatg gccgcgcacc ttatggtctt
3661  tggtgaagag gggctcgcga agctcctcct cacgtatgaa gcggccggtg gccgggtgtg
3721  gccgcggctc gcccaccaca tcgcggagcg ccttgcgttc ggggcggtca cctacgcact
3781  cttcgccctc gactcgggta acgaagagta cctcgctgcg gcgaaggcgc agctcgccgc
```

```
3841  agcggaatga gcgaacgtcg atatagcccg ctcgcgacgc tgttcgcggc gacctttctc 3901  ttccggatcg gcaacgcggt ggcggccctc gcgcttccat ggttcgtcct gtctcataca 3961  aagagcgcgg cctgggcggg cgccacggcc gctagcagcg tcatcgcgac catcatcggc 4021  gcgtgggttg gtggtggcct cgtcgatcgg ttcgggcgcg cgcccgtcgc attgatctcg 4081  ggtgtggtgg gcggcgtggc catggcgagc atcccactgc tcgatgccgt tggcgccctc 4141  tcgaacactg ggctgatcgc ttgcgtggtg ctcggtgccg cgttcgacgc acccggtatg 4201  gccgcgcagg acagtgagct gcccaaactc ggccacgtcg ccgggctctc cgttgagcgc 4261  gtctcgtcac tgaaagcggt gatcgggaac gtcgcgattc taggtggccc ggcccttggg 4321  ggggccgcaa tcggcctgct tggcgctgcg ccaacgctcg ggctgacggc gttctgctcc 4381  gtccttgcag gtctgctcgg cgcgtgggtg cttccgcgc gtgccgctcg gacgatgacc 4441  acgacggcga ctctctccat gcgcgccggc gtcgcttttc tctggagcga accctgctg 4501  cgccctctct ttggtatagt gatgatcttc gtgggcatcg ttggcgccaa cggcagcgtc 4561  atcatgcctg cgctgtttgt agatgcagga cgccaagtag cagagctcgg gctgttctcc 4621  tcaatgatgg gggctggtgg tctccttggc tgtccctcct gttcagctac tgacggggtg 4681  gtgcgtaacg gcaaaagcac cgccggacat cagcgctagc ggagtgtata ctggcttact 4741  atgttggcac tgatgagggt gtcagtgaag tgcttcatgt ggcaggagaa aaaaggctgc 4801  accggtgcgt cagcagaata tgtgatacag gatatattcc gcttcctcgc tcactgactc 4861  gctacgctcg gtcgttcgac tgcggcgagc ggaaatggct tacgaacggg gcggagattt 4921  cctggaagat gccaggaaga tacttaacag ggaagtgaga gggccgcggc aaagccgttt 4981  ttccataggc tccgccccccc tgacaagcat cacgaaatct gacgctcaaa tcagtggtgg 5041  cgaaacccga caggactata aagataccag gcgtttcccc ctggcggctc cctcgtgcgc 5101  tctcctgttc ctgcctttcg gtttaccggt g
```

DNA Sequences with Upstream Nucleotide Sequences
Mutated nucleotides are underlined
RBS region is shown bold
Start codon is shown boxed

WT (SEQ ID NO: 28)

AGAAGGTGAACACTG[ATG]CCCCGCCCCAAGCTCAAGTCCGATGACGAGGTACTCGA

GGCCGCCACCGTAGTGCTGAAGCGTTGCGGTCCCATAGAGTTCACGCTCAGCGGAG

TAGCAAAGGAGGTGGGGCTCTCCCGCGCAGCGTTAATCCAGCGCTTCACCAACCGC

GATACGCTGCTGGTGAGGATGATGGAGCGCGGCGTCGAGCAGGTGCGGCATTACCT

GAATGCGATACCGATAGGCGCAGGGCCGCAAGGGCTCTGGGAATTTTTGCAGGTGC

TCGTTCGGAGCATGAACACTCGCAACGACTTCTCGGTGAACTATCTCATCTCCTGGT

ACGAGCTCCAGGTGCCGGAGCTACGCACGCTTGCGATCCAGCGGAACCGCGCGGTG

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

AGCTAGCTGATCATGTGCTGGCTCAGATCGCTGCCATCCTGTGTTTAATGTTTCCCGA

ACACGACGATTTCCAACTCCTCCAGGCACATGCGTAA

-continued epA3

(SEQ ID NO: 29)

GGAAGGTGAACACTGATGCCCCGCCCCAAGCTCAAGTCCGATGACGAGGTACTCGA

GGCCGCCACCGTAGTGCTGAAGCGTTGCGGTCCCATAGAGTTCACGCTCAGCGGAG

TAGCAAAGGAGGTGGGGCTCTCCCGCGCAGCGTTAATCCAGCGCTTCACCAACCGC

GATACGCTGCTGGTGAGGATGATGGAGCGCGGCGTCGAGCAGGTGCGGCATTACCT

GAATGCGATACCGATATGCGCAGGGCCGCAAGGGCTCTGGGAATTTTTGCAGGTGC

TCGTTCGGAGCATGAACACTCGCAACGACTTCTCGGTGAACTATCTCATCTCCTGGT

ACGAGCTCCAGGTGCCGGAGCTACGCACGCTTGCGATCCAGCGGAACCGCGCGGTG

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

AGCTAGCTGATCATGTGCTGGCTCAGATCGCTGCCATCCTGTGTTTAATGTTTCCCGA

ACACGACGATTTCCAACTCCTCCAGGCACATGCGTAA epE7

(SEQ ID NO: 30)

AGATGGTGAACACTGATGCCCCGCCCCAAGCTCAAGTCCGATGACGAGGTACTCGA

GGCCGCCACCGTAGTGCTGAAGCGTTGCGGTCCCATAGAGTTCACGCTCAGCGGAG

TAGCAAAGGAGGTGGGGCTCTCCCGCGCAGCGTTAATCCAGCGCTTCACCAACCGC

GATACGCTGCTGGTGAGGATGATGGAGCGCGGCGTCGAGCAGGTGCGGCATTACCT

TAATGCGATACCGATAGGCGCAGGGCCGCAAGGGCTCTGGGAATTTTTGCAGGTGC

TCATTCGGAGCATGAACACTCGCAACGACTTCTCGGTGAACTATCTCATCTCCTGGT

ACGAGCTCCAGGTGCCGGAGCTACGCACGCTTGCGATCCAGCGGAACCGCGCGGTG

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

AGCTAGCTGATCATGTGCTGGCTCAGATCGCTGCCATCCTGTGTTTAATGTTTCCCGA

ACACGACGATTTCCAACTCCTCCAGGCACATGCGTAA

WT A3-RBS (SEQ ID NO: 31)

GGAAGGTGAACACTGATGCCCCGCCCCAAGCTCAAGTCCGATGACGAGGTACTCGA

GGCCGCCACCGTAGTGCTGAAGCGTTGCGGTCCCATAGAGTTCACGCTCAGCGGAG

TAGCAAAGGAGGTGGGGCTCTCCCGCGCAGCGTTAATCCAGCGCTTCACCAACCGC

GATACGCTGCTGGTGAGGATGATGGAGCGCGGCGTCGAGCAGGTGCGGCATTACCT

GAATGCGATACCGATAGGCGCAGGGCCGCAAGGGCTCTGGGAATTTTTGCAGGTGC

TCGTTCGGAGCATGAACACTCGCAACGACTTCTCGGTGAACTATCTCATCTCCTGGT

ACGAGCTCCAGGTGCCGGAGCTACGCACGCTTGCGATCCAGCGGAACCGCGCGGTG

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

AGCTAGCTGATCATGTGCTGGCTCAGATCGCTGCCATCCTGTGTTTAATGTTTCCCGA

ACACGACGATTTCCAACTCCTCCAGGCACATGCGTAA

WT E7-RBS (SEQ ID NO: 32)

AGATGGTGAACACTGATGCCCCGCCCCAAGCTCAAGTCCGATGACGAGGTACTCGA

GGCCGCCACCGTAGTGCTGAAGCGTTGCGGTCCCATAGAGTTCACGCTCAGCGGAG

TAGCAAAGGAGGTGGGGCTCTCCCGCGCAGCGTTAATCCAGCGCTTCACCAACCGC

GATACGCTGCTGGTGAGGATGATGGAGCGCGGCGTCGAGCAGGTGCGGCATTACCT

GAATGCGATACCGATAGGCGCAGGGCCGCAAGGGCTCTGGGAATTTTTGCAGGTGC

TCGTTCGGAGCATGAACACTCGCAACGACTTCTCGGTGAACTATCTCATCTCCTGGT

ACGAGCTCCAGGTGCCGGAGCTACGCACGCTTGCGATCCAGCGGAACCGCGCGGTG

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

AGCTAGCTGATCATGTGCTGGCTCAGATCGCTGCCATCCTGTGTTTAATGTTTCCCGA

ACACGACGATTTCCAACTCCTCCAGGCACATGCGTAA

WT H4-RBS (SEQ ID NO: 33)

AGAAGGC GAACACTGATGCCCCGCCCCAAGCTCAAGTCCGATGACGAGGTACTCGA

GGCCGCCACCGTAGTGCTGAAGCGTTGCGGTCCCATAGAGTTCACGCTCAGCGGAG

TAGCAAAGGAGGTGGGGCTCTCCCGCGCAGCGTTAATCCAGCGCTTCACCAACCGC

GATACGCTGCTGGTGAGGATGATGGAGCGCGGCGTCGAGCAGGTGCGGCATTACCT

GAATGCGATACCGATAGGCGCAGGGCCGCAAGGGCTCTGGGAATTTTTGCAGGTGC

TCGTTCGGAGCATGAACACTCGCAACGACTTCTCGGTGAACTATCTCATCTCCTGGT

ACGAGCTCCAGGTGCCGGAGCTACGCACGCTTGCGATCCAGCGGAACCGCGCGGTG

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

AGCTAGCTGATCATGTGCTGGCTCAGATCGCTGCCATCCTGTGTTTAATGTTTCCCGA

ACACGACGATTTCCAACTCCTCCAGGCACATGCGTAA

QCMS3D6

(SEQ ID NO: 34)

AGAAGGTGAACACTGATGCCCCGCCCCAAGCTCAAGTCCGATGACGAGGTACTCGA

GGCCGCCAGGGTAGTGCTGAAGCGTTGCGGTCCCATAGAGTTCACGCTCAGCGGAG

TAGCAAAGGAGGTGGGGCTCTCCCGCGCAGCGTTAATCCAGCGCTTCACCAACCGC

GATACGCTGCTGGTGAGGATGATGGAGCGCGGCGTCGAGCAGGTGCGGCATTACCT

GAATGCGATACCGATAGGCGCAGGGCCGCAAGGGCTCTGGGAATTTTTGCAGGTGG

TCGTTCGGAGCATGAACACTCGCAACGACTTCTCGGTGAACTATCTCATCTCCTGGT

ACGAGCTCCAGGTGCCGGAGCTACGCACGCTTGCGATCCAGCGGAACCGCGCGGTG

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

AGCTAGCTGATCATGTGCTGGCTCAGATCGCTGCCATCCTGTGTTTAATGTTTCCCGA

ACAcGAcGATTTCCAACTCCTCCAGGCACATGCGTAA

QCMS3F8

(SEQ ID NO: 35)

AGAAGGTGAACACTGATGCCCCGCCCCAAGCTCAAGTCCGATGACGAGGTACTCGA

GGCCGCCGCGGTAGTGCTGAAGCGTTGCGGTCCCATAGAGTTCACGCTCAGCGGAG

TAGCAAAGGAGGTGGGGCTCTCCCGCGCAGCGTTAATCCAGCGCTTCACCAACCGC

GATACGCTGCTGGTGAGGATGAGTGAGCGCGGCGTCGAGCAGGTGCGGCATTACCT

GAATGCGATACCGATAGGCGCAGGGCCGCAAGGGCTCTGGGAATTTTTGCAGGTGC

TCGTTCGGAGCATGAACACTCGCAACGACTTCTCGGTGAACTATCTCATCTCCTGGT

ACGAGCTCCAGGTGCCGGAGCTACGCACGCTTGCGATCCAGCGGAACCGCGCGGTG

-continued

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

AGCTAGCTGATCATGTGCTGGCTCAGATCGCTGCCATCCTGTGTTTAATGTTTCCCGA

ACACGACGATTTCCAACTCCTCCAGGCACATGCGTAA

QCMS5B4

(SEQ ID NO: 36)

AGAAGGTGAACACTGAATGCCCCGCCCCAAGCTCAAGTCCGATGACGAGGTACTCGA

GGCCGCCGGTGTAGTGCTGAAGCGTTGCGGTCCCATAGAGTTCACGCTCAGCGGAG

TAGCAAAGGAGGTGGGGCTCTCCCGCGCAGCGTTAATCCAGCGCTTCACCAACCGC

GATACGCTGCTGGTGAGGATGATGGAGCGCGGCGTCGAGATGGTTCGGCATTACCT

GAATGCGATACCGATAGGCGCAGGGCCGCAAGGGCTCTGGGAATTTTTGCAGGTGC

TCGTTCGGAGCATGAACACTCGCAACGACTTCTCGGTGAACTATCTCATCTCCTGGT

ACGAGCTCCAGGTGCCGGAGCTACGCACGCTTGCGATCCAGCGGAACCGCGCGGTG

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

AGCTAGCTGATCATGTGCTGGCTCAGATCGCTGCCATCCTGTGTTTAATGTTTCCCGA

ACAcGACGATTTCCAACTCCTCCAGGCACATGCGTAA

QCMS5D7

(SEQ ID NO: 37)

AGAAGGTGAACACTGAATGCCCCGCCCCAAGCTCAAGTCCGATGACGAGGTACTCGA

GGCCGCCGCTGTAGTGCTGAAGCGTTGCGGTCCCATAGAGTTCACGCTCAGCGGAGT

AGCAAAGGAGGTGGGGCTCTCCCGCGCAGCGTTAATCCAGCGCTTCACCAACCGCG

ATACGCTGCTGGTGAGGATGGAGGAGCGCGGCGTCGAGCAGGTGCGGCATTACCTG

AATGCGATACCGATAGGCGCAGGGCCGCAAGGGCTCTGGGAATTTTTGCAGGTGCT

CGTTCGGAGCATGAACACTCGCAACGACTTCTCGGTGAACTATCTCATCTCCTGGTA

CGAGCTCCAGGTGCCGGAGCTACGCACGCTTGCGATCCAGCGGAACCGCGCGGTGG

TGGAGGGGATCCGCAAGCGACTGCCCCCAGGTGCTCCTGCGGCAGCTGAGTTGCTC

CTGCACTCGGTCATCGCTGGCGCGACGATGCAGTGGGCCGTCGATCCGGATGGTGA

GCTAGCTGATCATGTGCTGGCTCAGATCGCTGCCATCCTGTGTTTAATGTTTCCCGAA

CACGACGATTTCCAACTCCTCCAGGCACATGCGTAA pikB1/D3
(SEQ ID NO: 38)
AGAAGGTGAACACTGAATGCCCCGCCCCAAGCTCAAGTCCGATGACGAGGTACTCGA

GGCCGCCACCGTAGTGCTGAAGCGTTGCGGTCCCATAGAGTTCACGCTCAGCGGAG

TAGCAAAGGAGGTGGGGCTCTCCCGCGCAGCGTTAATCCAGCGCTTCACCAACCGC

GATACGCTGCTGGTGAGGATGATGGAGCGCGGCGTCGAGCAGGTGCGGCATTACCT

GAATGCGATACCGATAGGCGCAGGGCCGCAAGGGCTCTGGGAATTTTTGCAGGTGC

TCGTTCGGAGCATGAACACTCGCAACGACTTCTCGGTGAACTATCTCATCTTCTGGT

ACGAGCTCCAGGTGCCGGAGCTACGCACGCTTGCGATCCAGCGGAACCGCGCGGTG

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

AGCTAGCTGATCATGTGCTGGCTCAGATCGCTGCCATCCTGTGTTTAATGTTTCCCGA

ACACGACGATTTCCAACTCCTCCAGGCACATGCGTAA

YCA11 (Three mutations upstream of the RBS [2 in promoter])
(SEQ ID NO: 39)

TGGTGCAAAACCTTTCGCGGTATGACATGATAGCGCCTCCCAGCCCATACAGAAGG

TGAACACTG[ATG]CCCCGCCCCAAGCTCAAGTCCGATGACGAGGTACTCGAGGCCGC

CACCGTAGTGCTGAAGCGTTGCGGTCCCATAGAGTTCACGCTCAGAGGAGTAGCAA

AGGAGGTGGGGCTCTCCCGCGCTGCGTTAATCCAGCGCTTCACCAACCGCGATACGC

TGCTGGTGAGGATGATGGAGCGCGGCGTCGAGCAGGTGCGACATTACCTGAATGCG

ATACCGATAGGCGCAGGGCCGCAAGGGCTCTGGGAATTTTTGCAGGTGCTCGTTCG

GAGCATGAACACTCGCAACGACTTCTCGGTGAACTATCTCATCTCCTGGTACGAGCT

CCAGGTGCCGGAGCTACGCACGCTTGCGATCCAGCGGAACCGCGCGGTGGTGGAGG

GGATCCGCAAGCGACTGCCCCCAGGTGCTCCTGCGGCAGCTGAGTTGCTCCTGCACT

CGGTCATCGCTGGCGCGACGATGCAGTGGGCCGTCGATCCGGATGGTGAGCTAGCT

GATCATGTGCTGGCTCAGATCGCTGCCATCCTGTGTTTAATGTTTCCCGAACACGAC

GATTTCCAACTCCTCCAGGCACATGCGTAA

Nbn.YCG11 (Two mutations [1 in promoter])
(SEQ ID NO: 40)

TGGTGCAAAACCTTTCGCGATATGGCATGATAGCGCCCCCCAACCCATACAGAAGG

TGAACTCTG[ATG]CCCCGCCCCAAGCTCAAGTCCGATGACGAGGTACTCGAGGCCGC

CACCGTAGTGCTGAAGCGTTGCGGTCCCATAGAGTTCACGCTCAGCGGAGTAGCAA

AGGAGGTGGGGTTCTCCCGCGCAGCGTTAATCCAGCGCTTCACCAACCGCGATACG

CTGCTGGTGAGGATGATGGAGCGCGGCGTCGAGCAGGTGCGGCATTACCTGAATGC

GATACCGATAGGCGCAGGGCCGCAAGGGCTCTGGGAATTTTTGCAGGTGCTCGTTC

GGAGCATGAACACTCGCAACGACTTCTCGGTGAACTATCTCATCTCCTGGTACGAGC

TCCAGGTGCCGGAGCTACGCACGCTTGCGATCCAGCGGAACCGCGCGGTGGTGGAG

GGGATCCGCAAGCGACTGCCCCCAGGTGCTCCTGCGGCAGCTGAGTTGCTCCTGCAC

TCGGTCATCGCTGGCGCGACGATGCAGTGGGCCGTCGATCCGGATGGTGAGCTAGC

TGATCATGTGCTGGCTCAGATCGCTGCCATCCTGTGTTTAATGTTTCCCGAACACGA

CGATTTCCAACTCCTCCAGGCACATGCGTAA

NbnD11
(SEQ ID NO: 41)

AGAAGGTGAACACTG[ATG]CCCCGCCCCAAGCTCAAGTCCGATGACGAGGTACTCGA

GGCCGCCACCGTAGTGCTGAAGCGTTGCGGTCCCATAGAGTTCACGCTCAGCGGACT

AGCAAAGGAGGTGGGGCTCTCCCGCGCAGCGTTAATCCAGCGCTTCACCAACCGCG

ATACGCTGCTGGTGAGGATGATGGAGCGCGGCGTCGAGCAGGTGCGGCATTACCTG

AATGCGATACCGATAGGCGCAGGGCCGCAAGGGCTCTGGGAATTTTTGCAGGTGCT

CGTTCGGAGCATGAACACTCGCAACGACTTCTCGGTGAACTATCTCATCTCCTGGTA

CGAGCTCCAGGTGCCGGAGCTACGCACCCTTGCGATCCAGCGGAACCGCGCGGTGG

TGGAGGGGATCCGCAAGCGACTGCCCCCAGGTGCTCCTGCGGCAGCTGAGTTGCTC

CTGCACTCGGTCATCGCTGGCGCGACGATGCAGTGGGCCGTCGATCCGGATGGTGA

GCTAGCTGATCATGTGCTGGCTCAGATCTCTGCCATCCTGTGTTTAATGTTTCCCGAA

CACGACGATTTCCAACTCCTCCAGGCACATGCGTAA

NbnE1 (One mutation between the RBS and start codon)
(SEQ ID NO: 42)
AGAAGGTGGACACTG[ATG]CCCCGCCCCAAGCTCAAGTCCGATGACGAGGTACTCGA

GGCCGCCACCGTAGTGCTGAAGCGTTGCGGTCCCATTGAGTTCACGCTCAGCGGAGT

ATCAAAGGAGGTGGGGCTCTCCCGCGCAGCGTTAATCCAGCGCTTCACCAACCGCG

ATACGCTGCTGGTGAGGATGATGGAGCGCGGCGTCGAGCAGGTGCGGCATTACCTG

AATGCGATACCGATAGGCGCAGGGCCGCAAGGGCTCTGGGAATTTTTGCAGGTGCT

CGTTCGGAGCATGAACACTCGCAACGACTTCTCGGTGAACTATCTCATCTCCTGGTA

CGAGCTCCAGGTGCCGGAGCTACGCACGCTTGCGATCCAGCGGAACCGCGCGGTGG

TGGAGGGGATCCGCAAGCGACTGCCCCCAGGTGCTCCTGCGGCAGCAGAGTTGCTC

CTGCACTCGGTCATCGCTGGCGCGACGATGCAGTGGGCCGTCGATCCGGATGGTGA

GCTAGCTGATCATGTGCTGGCTCAGATCGCTGCCATCCTGTGTTTAATGTTTCCCGAA

CACGACGATTTCCAACTCCTCCAGGCACATGCGTAA

NbnG7 (One mutation in promotor)
(SEQ ID NO: 43)
TGGTGCAAAACCTTTCGCGGTATGTCATGATAGCGCCCCCCAACCCATACAGAAGG

TGAACACTG[ATG]CCCCGCCCCAAGCTCAAGTCCGATGACGAGGTACTCGAGGCCGC

CACCGTAGTGCTGAAGCGTTGCGGTCCCATAGAGTTCACGCTCAGCGGAGTAGCAA

AGGAGGTGGGGCTCTCCCGCGCAGCGTTAATCCAGCGCTTCACCAACTGCGATACG

CTGCTGGTGAGGATGATGGAGCGCGGCGTCGAGCAGGTGCGGCATTACCTGAATGC

GATACCGATAGGCGCAGGGCCGCAAGGGCTCTGGGAATTTTTGCAGGTGCTCGTTC

GGAGCATGAACACTCGCAACGACTTCTCGGTGAACTATCTCATCTCCTGGTACGAGC

TCCAGGTGCCGGAGCTACGCACGCTTGCGATCCAGCGGAACCGCGCGGTGGTGGAG

GGGATCCGCAAGCGACTGCCCCCAGGTGCTCCTGCGGCAGCTGAGTTGCTCCTGCAC

TCGGTCATCGCTGGCGCGACGATGCAGTGGGCCGTCGATCCGGATGGTGAGCTAGC

TGATCATGTGCTGGCTCAGATCGCTGCCATCCTGTGTTTAATGTTTCCCGAACACGA

CGATTTCCAACTCCTCCAGGCACATGCGTAA

M2D6
(SEQ ID NO: 44)
AGAAGGTGAACACTG[ATG]CCCCGCCCCAAGCTCAAGTCCGATGACGAGGTTCTCGA

GGCCACCACCGTAGTGCTGAAGCGTTGCGGTCCCATAGAGTTCACGCTCAGTGGAGT

GGCAAAGGAGGTGGGGCTCTCCCGCGCAGCGTTAATCCAGCGCTTCACCAACCGCG

ATACGCTGCTGGTGAGGATGATGGAGCGCGGCGTCGAGCAGGTGCGGCATTACCTG

AATGCGATACCGATAGGCGCAGGGCCGCAAGGGCTCTGGGAATTTTTGCAGGTGCT

CGTTCGGAGCATGAACACTCCTCAACGACTTCTCGGTGAACTATCTCATCTCCTGGTA

CGAGCTCCAGGTGCCGGAGCTACGCACGCTTGCGATCCAGCGGAACCGCGCGGTAG

TGGAGGGGATCCGCAAGCGACTGCCCCCAGGTGCTCCTGCGGCAGCTGAGTTGCTC

CTGCACTCGGTCATCGCTGGCGCGATGAAGCAGTGGGCCGTCGATCCGGATGGTGA

GCTAGCTGATCATGTGCTGGCTCAGATCGCTGCCATCCTGTGTTTAATGTTTCCCGAA

CACGACGATTTCCAACTCCTCCAGGCACATGCGTAA

M2D7
(SEQ ID NO: 45)
AGAAGGTGAACACTG[ATG]CCCCGCCTCAAGCTCAAGTCCGATGACGAGGTACTCGA

GGCCGCCACCGTAGTGCTGAAGCGTTGCGGTCCCATAGAGTTCACGCTCAGCGGAG

-continued

```
TAGCAAAGGAGGTGGGGCTCTCCCGCGCAGCGTTAATCCAGCGCTTCACCAACCGC

GATACGCTGCTGGTGAGGATGATGGAGCGCGGCGTCGAGCAGGTGCGGCATTACCT

GAATGCGATACCGATAGGCGCAGGGCCGCAAGGGCTCTGGGAATTTTTGCAGGTGC

TCGTTCGGAGCATGAACACTCGCAACGACTTCTCGGTGAACTATCTCATCTCCTTGT

ACGAGCTCCAGGTGCCGGAGCTACGCACGCTTGCGATCCAGCGGAACCGCGCGGTG

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

AGCTAGCTGATCATGTGCTGGCTCAGATCGCTGCCATCCTGTGTTTAATGTTTCCCGA

ACACGACGATTTCCAACTCCTCCAGGCACGTGCGTAA
```

C9

(SEQ ID NO: 46)

```
AGAAGGTGAACACTGATGCCCCGCCCCAAGCTCAAGTCCGATGACGAGGTACTCGA

GGCCGCCACCGTAGTGCTGAAGCGTTGCGGTCCCATAGAGTTCACGCTCAGCGGAG

TATCAAAGGAGGTGGGGCTCTCCCGCGCAGCGTTAATCCAGCGCTTCACCAACCGC

GATACGCTGCTGGTGAGGATGATGGAGCGCGGCGTCGAGCAGGTGCGGCATTACCT

GAATGCGATACCGATAGGCGCAGGGCCGCAAGGGCTCTGGGAATTTTTGCAGGTGC

TCGTTCGGAGCATGAACACTCGCAACGACTTCTCGGTGAACAATCTCATCTCCTGGT

ACGAGCTCCAGGTGCCGGAGCTACGCACGCTTGCGATCCAGCGGAACCGCGCGGTG

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

AGCTAGCTGATCATGTGCTGGCTCAGATCGCTGCCATCCTGTGTTTAATGTTTCCCGA

ACACGACGATTTCCAATTCCTCCAGGCACATGCGTAA
```

V66P (SEQ ID NO: 47)

```
AGAAGGTGAACACTGATGCCCCGCCCCAAGCTCAAGTCCGATGACGAGGTACTCGA

GGCCGCCACCGTAGTGCTGAAGCGTTGCGGTCCCATAGAGTTCACGCTCAGCGGAG

TAGCAAAGGAGGTGGGGCTCTCCCGCGCAGCGTTAATCCAGCGCTTCACCAACCGC

GATACGCTGCTGGTGAGGATGATGGAGCGCGGCGTCGAGCAGCCACGGCATTACCT

GAATGCGATACCGATAGGCGCAGGGCCGCAAGGGCTCTGGGAATTTTTGCAGGTGC

TCGTTCGGAGCATGAACACTCGCAACGACTTCTCGGTGAACTATCTCATCTCCTGGT

ACGAGCTCCAGGTGCCGGAGCTACGCACGCTTGCGATCCAGCGGAACCGCGCGGTG

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

AGCTAGCTGATCATGTGCTGGCTCAGATCGCTGCCATCCTGTGTTTAATGTTTCCCGA

ACACGACGATTTCCAACTCCTCCAGGCACATGCGTAA
```

V66R (SEQ ID NO: 48)

```
AGAAGGTGAACACTGATGCCCCGCCCCAAGCTCAAGTCCGATGACGAGGTACTCGA

GGCCGCCACCGTAGTGCTGAAGCGTTGCGGTCCCATAGAGTTCACGCTCAGCGGAG

TAGCAAAGGAGGTGGGGCTCTCCCGCGCAGCGTTAATCCAGCGCTTCACCAACCGC

GATACGCTGCTGGTGAGGATGATGGAGCGCGGCGTCGAGCAGAGGCGGCATTACCT

GAATGCGATACCGATAGGCGCAGGGCCGCAAGGGCTCTGGGAATTTTTGCAGGTGC

TCGTTCGGAGCATGAACACTCGCAACGACTTCTCGGTGAACTATCTCATCTCCTGGT
```

ACGAGCTCCAGGTGCCGGAGCTACGCACGCTTGCGATCCAGCGGAACCGCGCGGTG

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

AGCTAGCTGATCATGTGCTGGCTCAGATCGCTGCCATCCTGTGTTTAATGTTTCCCGA

ACACGACGATTTCCAACTCCTCCAGGCACATGCGTAA

V66G (SEQ ID NO: 49)

AGAAGGTGAACACTGATGCCCCGCCCCAAGCTCAAGTCCGATGACGAGGTACTCGA

GGCCGCCACCGTAGTGCTGAAGCGTTGCGGTCCCATAGAGTTCACGCTCAGCGGAG

TAGCAAAGGAGGTGGGGCTCTCCCGCGCAGCGTTAATCCAGCGCTTCACCAACCGC

GATACGCTGCTGGTGAGGATGATGGAGCGCGGCGTCGAGCAGGGACGGCATTACCT

GAATGCGATACCGATAGGCGCAGGGCCGCAAGGGCTCTGGGAATTTTTGCAGGTGC

TCGTTCGGAGCATGAACACTCGCAACGACTTCTCGGTGAACTATCTCATCTCCTGGT

ACGAGCTCCAGGTGCCGGAGCTACGCACGCTTGCGATCCAGCGGAACCGCGCGGTG

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

AGCTAGCTGATCATGTGCTGGCTCAGATCGCTGCCATCCTGTGTTTAATGTTTCCCGA

ACACGACGATTTCCAACTCCTCCAGGCACATGCGTAA

V66I (SEQ ID NO: 50)

AGAAGGTGAACACTGATGCCCCGCCCCAAGCTCAAGTCCGATGACGAGGTACTCGA

GGCCGCCACCGTAGTGCTGAAGCGTTGCGGTCCCATAGAGTTCACGCTCAGCGGAG

TAGCAAAGGAGGTGGGGCTCTCCCGCGCAGCGTTAATCCAGCGCTTCACCAACCGC

GATACGCTGCTGGTGAGGATGATGGAGCGCGGCGTCGAGCAGATCCGGCATTACCT

GAATGCGATACCGATAGGCGCAGGGCCGCAAGGGCTCTGGGAATTTTTGCAGGTGC

TCGTTCGGAGCATGAACACTCGCAACGACTTCTCGGTGAACTATCTCATCTCCTGGT

ACGAGCTCCAGGTGCCGGAGCTACGCACGCTTGCGATCCAGCGGAACCGCGCGGTG

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

AGCTAGCTGATCATGTGCTGGCTCAGATCGCTGCCATCCTGTGTTTAATGTTTCCCGA

ACACGACGATTTCCAACTCCTCCAGGCACATGCGTAA

V66D (SEQ ID NO: 51)

AGAAGGTGAACACTGATGCCCCGCCCCAAGCTCAAGTCCGATGACGAGGTACTCGA

GGCCGCCACCGTAGTGCTGAAGCGTTGCGGTCCCATAGAGTTCACGCTCAGCGGAG

TAGCAAAGGAGGTGGGGCTCTCCCGCGCAGCGTTAATCCAGCGCTTCACCAACCGC

GATACGCTGCTGGTGAGGATGATGGAGCGCGGCGTCGAGCAGGACCGGCATTACCT

GAATGCGATACCGATAGGCGCAGGGCCGCAAGGGCTCTGGGAATTTTTGCAGGTGC

TCGTTCGGAGCATGAACACTCGCAACGACTTCTCGGTGAACTATCTCATCTCCTGGT

ACGAGCTCCAGGTGCCGGAGCTACGCACGCTTGCGATCCAGCGGAACCGCGCGGTG

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

-continued

AGCTAGCTGATCATGTGCTGGCTCAGATCGCTGCCATCCTGTGTTTAATGTTTCCCGA

ACACGACGATTTCCAACTCCTCCAGGCACATGCGTAA

M1B10

(SEQ ID NO: 52)

AGAAGGCGAACACTG<u>ATG</u>CCCCGCCCCAAGCTCAAGTCCGATGACGAGGTACTCGA

GGCCGCCACCGTAGTGCTGAAGCGTTGCGGTCCCATAGAGTTCACGCTCAGCGGAG

TAGCAAAGGAGGTGGGGCTCTCCCGCGCAGCGTTAATCCAGCGCTTCA<u>T</u>CAACCGC

GATACGCTGCTGGTGAGGATGATGGAGCGCGGCGTCGAGCAGGTGCGGCATTACCT

GAATGCGATACCGATAGGCGCAGGGCCGCAAGGGCTCTGGGAATTTTTGCAGGTG<u>T</u>

TCGTTCGGAGCATGAACACTCGCAAC<u>A</u>ACTTCTCGGTGAACTATCTCATCTCCTGGT

ACGA<u>T</u>CTCCAGGTGCCGGAGCTACGCACGCTTGCGATCCAGCGGAACCGCGCGGTG

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

AGCTAGCTGATCATGTGCTGGCTCAGATCGCTGCCATCCTGTGTTTAATGTTTCCCGA

ACACGACGATTTCCAACTCCTCCAGGCACATGCGTAA smRBS 1A1

(SEQ ID NO: 53)

TTCAGGTGAACACTG<u>ATG</u>CCCCGCCCCAAGCTCAAGTCCGATGACGAGGTACTCGA

GGCCGCCACCGTAGTGCTGAAGCGTTGCGGTCCCATAGAGTTCACGCTCAGCGGAG

TAGCAAAGGAGGTGGGGCTCTCCCGCGCAGCGTTAATCCAGCGCTTCACCAACCGC

GATACGCTGCTGGTGAGGATGATGGAGCGCGGCGTCGAGCAGGTGCGGCATTACCT

GAATGCGATACCGATAGGCGCAGGGCCGCAAGGGCTCTGGGAATTTTTGCAGGTGC

TCGTTCGGAGCATGAACACTCGCAACGACTTCTCGGTGAACTATCTCATCTCCTGGT

ACGAGCTCCAGGTGCCGGAGCTACGCACGCTTGCGATCCAGCGGAACCGCGCGGTG

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

AGCTAGCTGATCATGTGCTGGCTCAGATCGCTGCCATCCTGTGTTTAATGTTTCCCGA

ACACGACGATTTCCAACTCCTCCAGGCACATGCGTAA smRBS 1G7

(SEQ ID NO: 54)

CTGAGGTGAACACTG<u>ATG</u>CCCCGCCCCAAGCTCAAGTCCGATGACGAGGTACTCGA

GGCCGCCACCGTAGTGCTGAAGCGTTGCGGTCCCATAGAGTTCACGCTCAGCGGAG

TAGCAAAGGAGGTGGGGCTCTCCCGCGCAGCGTTAATCCAGCGCTTCACCAACCGC

GATACGCTGCTGGTGAGGATGATGGAGCGCGGCGTCGAGCAGGTGCGGCATTACCT

GAATGCGATACCGATAGGCGCAGGGCCGCAAGGGCTCTGGGAATTTTTGCAGGTGC

TCGTTCGGAGCATGAACACTCGCAACGACTTCTCGGTGAACTATCTCATCTCCTGGT

ACGAGCTCCAGGTGCCGGAGCTACGCACGCTTGCGATCCAGCGGAACCGCGCGGTG

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

AGCTAGCTGATCATGTGCTGGCTCAGATCGCTGCCATCCTGTGTTTAATGTTTCCCGA

ACACGACGATTTCCAACTCCTCCAGGCACATGCGTAA

-continued smRBS 2E1

(SEQ ID NO: 55)

AAAAGGTGAACACTGA̲T̲G̲CCCCGCCCCAAGCTCAAGTCCGATGACGAGGTACTCGA

GGCCGCCACCGTAGTGCTGAAGCGTTGCGGTCCCATAGAGTTCACGCTCAGCGGAG

TAGCAAAGGAGGTGGGGCTCTCCCGCGCAGCGTTAATCCAGCGCTTCACCAACCGC

GATACGCTGCTGGTGAGGATGATGGAGCGCGGCGTCGAGCAGGTGCGGCATTACCT

GAATGCGATACCGATAGGCGCAGGGCCGCAAGGGCTCTGGGAATTTTTGCAGGTGC

TCGTTCGGAGCATGAACACTCGCAACGACTTCTCGGTGAACTATCTCATCTCCTGGT

ACGAGCTCCAGGTGCCGGAGCTACGCACGCTTGCGATCCAGCGGAACCGCGCGGTG

GTGGAGGGGATCCGCAAGCGACTGCCCCCAGGTGCTCCTGCGGCAGCTGAGTTGCT

CCTGCACTCGGTCATCGCTGGCGCGACGATGCAGTGGGCCGTCGATCCGGATGGTG

AGCTAGCTGATCATGTGCTGGCTCAGATCGCTGCCATCCTGTGTTTAATGTTTCCCGA

ACACGACGATTTCCAACTCCTCCAGGCACATGCGTAA

M9C4

(SEQ ID NO: 56)

AGAAGGTGAACACTGA̲T̲G̲CCCCGCCCCAAGCTCAAGTCCGATGACGAGGTACTCGA

GGCCGCCACCGTAGTGCTGAAGCGTTGCGGTCCCATAGAGTTCACGCTCAGCGGAG

TAGCAAAGGAGGTGGGA̲CTCTCCCGCGCAGCGTTAATCCAGCGCTTCACCAACCGC

GATACGCTGCTGGTGAGGATGATGGAGCGCGGCGTCGAGCAGGTGCGGCATTACCT

GAATGCGATACCGATAGGCGCAGGGCCGCAAGGGCTCTGGGAATTTTTGCAGGTGC

TCGTTCGGAGCATGAACACTCGCAACGACTTCTCGGTGAACTATCTCATCTCCTGGT

ACGAGCTCCAGGTGCCGGAGCTACGCACGCTTGCGATCCAGA̲C̲TAACCGCGCGGTG

GTGGAGGGGATCCGCAAT̲CGACTGCCCCCAGGTGCTCCTGCGGCAGCTGAGTTGCTC

CTGCACTCGGTCATCA̲CTGGCGCGACGATGCAGTGGGCCGTCGATCCGGATGGTGA

GCTAGCTGATCATGTGCTGGCTCAGATCGCTGCCATCCTGTGTTTAATGTTTCCCGAA

CAA̲GACGATTTCCAACTCCTCCAGGCACATGCGTAA

E7_M9C4

(SEQ ID NO: 57)

AGAT̲GGTGAACACTGA̲T̲G̲CCCCGCCCCAAGCTCAAGTCCGATGACGAGGTACTCGA

GGCCGCCACCGTAGTGCTGAAGCGTTGCGGTCCCATAGAGTTCACGCTCAGCGGAG

TAGCAAAGGAGGTGGGA̲CTCTCCCGCGCAGCGTTAATCCAGCGCTTCACCAACCGC

GATACGCTGCTGGTGAGGATGATGGAGCGCGGCGTCGAGCAGGTGCGGCATTACCT

GAATGCGATACCGATAGGCGCAGGGCCGCAAGGGCTCTGGGAATTTTTGCAGGTGC

TCGTTCGGAGCATGAACACTCGCAACGACTTCTCGGTGAACTATCTCATCTCCTGGT

ACGAGCTCCAGGTGCCGGAGCTACGCACGCTTGCGATCCAGA̲C̲TAACCGCGCGGTG

GTGGAGGGGATCCGCAAT̲CGACTGCCCCCAGGTGCTCCTGCGGCAGCTGAGTTGCTC

CTGCACTCGGTCATCA̲CTGGCGCGACGATGCAGTGGGCCGTCGATCCGGATGGTGA

GCTAGCTGATCATGTGCTGGCTCAGATCGCTGCCATCCTGTGTTTAATGTTTCCCGAA

CAA̲GACGATTTCCAACTCCTCCAGGCACATGCGTAA pMLCmR, E7_M9C4_pMLCmR
MphR sequence same as WT and E7 mutant (above)

In some embodiments, the MphR gene sequence may be codon optimized, without changing the resulting polypeptide sequence. In some embodiments, the codon optimization includes replacing at least one, or more than one, or a significant number, of codons.

In some embodiments, the MphR gene sequence is substantially identical to the wild-type MphR sequence (SEQ ID NO:1). In some embodiments, the MphR gene is about 60% identical, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher, over a specified region when compared and aligned for maximum correspondence with the wild-type sequence.

In some embodiments, the MphR gene sequence is substantially identical to the wild-type MphR sequence (SEQ ID NO:28) (which includes gene sequences upstream of the start codon). In some embodiments, the MphR gene is about 60% identical, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher, over a specified region when compared and aligned for maximum correspondence with the wild-type sequence.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

SEQUENCE LISTING

```
<160> NUMBER OF SEQ ID NOS: 59

<210> SEQ ID NO 1
<211> LENGTH: 585
<212> TYPE: DNA
<213> ORGANISM: Artificial Sequence
<220> FEATURE:
<223> OTHER INFORMATION: synthetic construct

<400> SEQUENCE: 1
atgccccgcc ccaagctcaa gtccgatgac gaggtactcg aggccgccac cgtagtgctg      60
aagcgttgcg gtcccataga gttcacgctc agcggagtag caaaggaggt ggggctctcc     120
cgcgcagcgt taatccagcg cttcaccaac cgcgatacgc tgctggtgag gatgatggag     180
cgcggcgtcg agcaggtgcg gcattacctg aatgcgatac cgataggcgc agggccgcaa     240
gggctctggg aattttttgca ggtgctcgtt cggagcatga acactcgcaa cgacttctcg     300
gtgaactatc tcatctcctg gtacgagctc caggtgccgg agctacgcac gcttgcgatc     360
cagcggaacc gcgcggtggt ggaggggatc cgcaagcgac tgcccccagg tgctcctgcg     420
gcagctgagt tgctcctgca ctcggtcatc gctggcgcga cgatgcagtg ggccgtcgat     480
ccggatggtg agctagctga tcatgtgctg gctcagatcg ctgccatcct gtgtttaatg     540
tttcccgaac acgacgattt ccaactcctc caggcacatg cgtaa                     585

<210> SEQ ID NO 2
<211> LENGTH: 194
<212> TYPE: PRT
<213> ORGANISM: Artificial Sequence
<220> FEATURE:
<223> OTHER INFORMATION: synthetic construct

<400> SEQUENCE: 2

Met Pro Arg Pro Lys Leu Lys Ser Asp Asp Glu Val Leu Glu Ala Ala
1               5                  10                  15

Thr Val Val Leu Lys Arg Cys Gly Pro Ile Glu Phe Thr Leu Ser Gly
            20                  25                  30

Val Ala Lys Glu Val Gly Leu Ser Arg Ala Ala Leu Ile Gln Arg Phe
        35                  40                  45

Thr Asn Arg Asp Thr Leu Leu Val Arg Met Met Glu Arg Gly Val Glu
```

```
              50                  55                  60
Gln Val Arg His Tyr Leu Asn Ala Ile Pro Ile Gly Ala Gly Pro Gln
 65                  70                  75                  80

Gly Leu Trp Glu Phe Leu Gln Val Leu Val Arg Ser Met Asn Thr Arg
                 85                  90                  95

Asn Asp Phe Ser Val Asn Tyr Leu Ile Ser Trp Tyr Glu Leu Gln Val
                100                 105                 110

Pro Glu Leu Arg Thr Leu Ala Ile Gln Arg Asn Arg Ala Val Val Glu
            115                 120                 125

Gly Ile Arg Lys Arg Leu Pro Pro Gly Ala Pro Ala Ala Ala Glu Leu
        130                 135                 140

Leu Leu His Ser Val Ile Ala Gly Ala Thr Met Gln Trp Ala Val Asp
145                 150                 155                 160

Pro Asp Gly Glu Leu Ala Asp His Val Leu Ala Gln Ile Ala Ala Ile
                165                 170                 175

Leu Cys Leu Met Phe Pro Glu His Asp Asp Phe Gln Leu Leu Gln Ala
                180                 185                 190

His Ala

<210> SEQ ID NO 3
<211> LENGTH: 585
<212> TYPE: DNA
<213> ORGANISM: Artificial Sequence
<220> FEATURE:
<223> OTHER INFORMATION: synthetic construct

<400> SEQUENCE: 3
atgccccgcc ccaagctcaa gtccgatgac gaggtactcg aggccgccac cgtagtgctg       60
aagcgttgcg gtcccataga gttcacgctc agcggagtag caaggaggt ggggctctcc      120 cgcgcagcgt taatccagcg cttcaccaac gcgatacgc tgctggtgag gatgatggag      180
cgcggcgtcg agcaggtgcg gcattacctg aatgcgatac cgatatgcgc agggccgcaa      240
gggctctggg aatttttgca ggtgctcgtt cggagcatga acactcgcaa cgacttctcg      300
gtgaactatc tcatctcctg gtacgagctc caggtgccgg agctacgcac gcttgcgatc      360
cagcggaacc gcgcggtggt ggaggggatc cgcaagcgac tgcccccagg tgctcctgcg      420
gcagctgagt tgctcctgca ctcggtcatc gctggcgcga cgatgcagtg ggccgtcgat      480
ccggatggtg agctagctga tcatgtgctg gctcagatcg ctgccatcct gtgtttaatg      540
tttcccgaac acgacgattt ccaactcctc caggcacatg cgtaa                      585

<210> SEQ ID NO 4
<211> LENGTH: 585
<212> TYPE: DNA
<213> ORGANISM: Artificial Sequence
<220> FEATURE:
<223> OTHER INFORMATION: synthetic construct

<400> SEQUENCE: 4
atgccccgcc ccaagctcaa gtccgatgac gaggtactcg aggccgccac cgtagtgctg       60
aagcgttgcg gtcccataga gttcacgctc agcggagtag caaggaggt ggggctctcc      120 cgcgcagcgt taatccagcg cttcaccaac gcgatacgc tgctggtgag gatgatggag      180
cgcggcgtcg agcaggtgcg gcattacctt aatgcgatac cgataggcgc agggccgcaa      240
gggctctggg aatttttgca ggtgctcatt cggagcatga acactcgcaa cgacttctcg      300
gtgaactatc tcatctcctg gtacgagctc caggtgccgg agctacgcac gcttgcgatc      360
```

```
cagcggaacc gcgcggtggt ggaggggatc cgcaagcgac tgccccagg tgctcctgcg      420 gcagctgagt tgctcctgca ctcggtcatc gctggcgcga cgatgcagtg ggccgtcgat      480
ccggatggtg agctagctga tcatgtgctg gctcagatcg ctgccatcct gtgtttaatg      540
tttcccgaac acgacgattt ccaactcctc caggcacatg cgtaa                     585
```

<210> SEQ ID NO 5
<211> LENGTH: 585
<212> TYPE: DNA
<213> ORGANISM: Artificial Sequence
<220> FEATURE:
<223> OTHER INFORMATION: synthetic construct

<400> SEQUENCE: 5

```
atgccccgcc ccaagctcaa gtccgatgac gaggtactcg aggccgccac cgtagtgctg       60
aagcattgcg gtcccataga gttcacgctc agcggagtag caaatgaggt ggggctctcc      120
cgcgcagcgt taatccagcg cttcaccaac cgcgatacgc tgctggtgag gatgatggag      180
cgcggcgtcg agcaggtgcg gcattacctg aatgcgatac cgataggcgc agggccgcaa      240
gggctctggg aattttttgca ggtgctcgtt cggagcatga acactcgcaa cgacttctcg     300
gtgaactatc tcatctcttg gtacgagctc caggtgccgg agctacgcac gcttgcgatc      360
cagcggaacc gcgcggtggt ggaggggatc cgcaagcgac tgccccagg tgctcctgcg      420 gcagctgagt tgctcctgca ctcggtcatc gctggcgcga cgatgcagtg ggccgtcgat      480
ccggatggtg agctagctga tcatgtgctg gctcagatcg ctgccatcct gtgtttaatg      540
tttcccgaac acgacgattt ccaactcctc caggcacatg cgtaa                     585
```

<210> SEQ ID NO 6
<211> LENGTH: 585
<212> TYPE: DNA
<213> ORGANISM: Artificial Sequence
<220> FEATURE:
<223> OTHER INFORMATION: synthetic construct

<400> SEQUENCE: 6

```
atgccccgcc ccaagctcaa gtccgatgac gaggtactcg aggccgccag ggtagtgctg       60
aagcgttgcg gtcccataga gttcacgctc agcggagtag caaaggaggt ggggctctcc      120
cgcgcagcgt taatccagcg cttcaccaac cgcgatacgc tgctggtgag gatgatggag      180
cgcggcgtcg agcaggtgcg gcattacctg aatgcgatac cgataggcgc agggccgcaa      240
gggctctggg aattttttgca ggtgctcgtt cggagcatga acactcgcaa cgacttctcg     300
gtgaactatc tcatctcctg gtacgagctc caggtgccgg agctacgcac gcttgcgatc      360
cagcggaacc gcgcggtggt ggaggggatc cgcaagcgac tgccccagg tgctcctgcg      420 gcagctgagt tgctcctgca ctcggtcatc gctggcgcga cgatgcagtg ggccgtcgat      480
ccggatggtg agctagctga tcatgtgctg gctcagatcg ctgccatcct gtgtttaatg      540
tttcccgaac acgacgattt ccaactcctc caggcacatg cgtaa                     585
```

<210> SEQ ID NO 7
<211> LENGTH: 585
<212> TYPE: DNA
<213> ORGANISM: Artificial Sequence
<220> FEATURE:
<223> OTHER INFORMATION: synthetic construct

<400> SEQUENCE: 7

```
atgccccgcc ccaagctcaa gtccgatgac gaggtactcg aggccgccgc ggtagtgctg      60
aagcgttgcg gtcccataga gttcacgctc agcggagtag caaaggaggt ggggctctcc     120
cgcgcagcgt taatccagcg cttcaccaac cgcgatacgc tgctggtgag gatgagtgag     180
cgcggcgtcg agcaggtgcg gcattacctg aatgcgatac cgataggcgc agggccgcaa     240
gggctctggg aattttttgca ggtgctcgtt cggagcatga acactcgcaa cgacttctcg     300
gtgaactatc tcatctcctg gtacgagctc caggtgccgg agctacgcac gcttgcgatc     360
cagcggaacc gcgcggtggt ggaggggatc cgcaagcgac tgcccccagg tgctcctgcg     420
gcagctgagt tgctcctgca ctcggtcatc gctggcgcga cgatgcagtg ggccgtcgat     480
ccggatggtg agctagctga tcatgtgctg gctcagatcg ctgccatcct gtgtttaatg     540
tttcccgaac acgacgattt ccaactcctc caggcacatg cgtaa                     585
```

<210> SEQ ID NO 8
<211> LENGTH: 585
<212> TYPE: DNA
<213> ORGANISM: Artificial Sequence
<220> FEATURE:
<223> OTHER INFORMATION: synthetic construct

<400> SEQUENCE: 8

```
atgccccgcc ccaagctcaa gtccgatgac gaggtactcg aggccgccgg tgtagtgctg      60
aagcgttgcg gtcccataga gttcacgctc agcggagtag caaaggaggt ggggctctcc     120
cgcgcagcgt taatccagcg cttcaccaac cgcgatacgc tgctggtgag gatgatggag     180
cgcggcgtcg agatggttcg gcattacctg aatgcgatac cgataggcgc agggccgcaa     240
gggctctggg aattttttgca ggtgctcgtt cggagcatga acactcgcaa cgacttctcg     300
gtgaactatc tcatctcctg gtacgagctc caggtgccgg agctacgcac gcttgcgatc     360
cagcggaacc gcgcggtggt ggaggggatc cgcaagcgac tgcccccagg tgctcctgcg     420
gcagctgagt tgctcctgca ctcggtcatc gctggcgcga cgatgcagtg ggccgtcgat     480
ccggatggtg agctagctga tcatgtgctg gctcagatcg ctgccatcct gtgtttaatg     540
tttcccgaac acgacgattt ccaactcctc caggcacatg cgtaa                     585
```

<210> SEQ ID NO 9
<211> LENGTH: 585
<212> TYPE: DNA
<213> ORGANISM: Artificial Sequence
<220> FEATURE:
<223> OTHER INFORMATION: synthetic construct

<400> SEQUENCE: 9

```
atgccccgcc ccaagctcaa gtccgatgac gaggtactcg aggccgccgc tgtagtgctg      60
aagcgttgcg gtcccataga gttcacgctc agcggagtag caaaggaggt ggggctctcc     120
cgcgcagcgt taatccagcg cttcaccaac cgcgatacgc tgctggtgag gatggaggag     180
cgcggcgtcg agcaggtgcg gcattacctg aatgcgatac cgataggcgc agggccgcaa     240
gggctctggg aattttttgca ggtgctcgtt cggagcatga acactcgcaa cgacttctcg     300
gtgaactatc tcatctcctg gtacgagctc caggtgccgg agctacgcac gcttgcgatc     360
cagcggaacc gcgcggtggt ggaggggatc cgcaagcgac tgcccccagg tgctcctgcg     420
gcagctgagt tgctcctgca ctcggtcatc gctggcgcga cgatgcagtg ggccgtcgat     480
ccggatggtg agctagctga tcatgtgctg gctcagatcg ctgccatcct gtgtttaatg     540
tttcccgaac acgacgattt ccaactcctc caggcacatg cgtaa                     585
```

<210> SEQ ID NO 10
<211> LENGTH: 585
<212> TYPE: DNA
<213> ORGANISM: Artificial Sequence
<220> FEATURE:
<223> OTHER INFORMATION: synthetic construct

<400> SEQUENCE: 10

| | |
|---|---|
| atgccccgcc ccaagctcaa gtccgatgac gaggtactcg aggccgccac cgtagtgctg | 60 |
| aagcgttgcg gtcccataga gttcacgctc agcggagtag caaaggaggt ggggctctcc | 120 |
| cgcgcagcgt taatccagcg cttcaccaac cgcgatacgc tgctggtgag gatgatggag | 180 |
| cgcggcgtcg agcaggtgcg gcattacctg aatgcgatac cgataggcgc agggccgcaa | 240 |
| gggctctggg aattttgca ggtgctcgtt cggagcatga acactcgcaa cgacttctcg | 300 |
| gtgaactatc tcatcttctg gtacgagctc caggtgccgg agctacgcac gcttgcgatc | 360 |
| cagcggaacc gcgcggtggt ggaggggatc cgcaagcgac tgcccccagg tgctcctgcg | 420 |
| gcagctgagt tgctcctgca ctcggtcatc gctggcgcga cgatgcagtg ggccgtcgat | 480 |
| ccggatggtg agctagctga tcatgtgctg gctcagatcg ctgccatcct gtgtttaatg | 540 |
| tttcccgaac acgacgattt ccaactcctc caggcacatg cgtaa | 585 |

<210> SEQ ID NO 11
<211> LENGTH: 585
<212> TYPE: DNA
<213> ORGANISM: Artificial Sequence
<220> FEATURE:
<223> OTHER INFORMATION: synthetic construct

<400> SEQUENCE: 11

| | |
|---|---|
| atgccccgcc ccaagctcaa gtccgatgac gaggtactcg aggccgccac cgtagtgctg | 60 |
| aagcgttgcg gtcccataga gttcacgctc agaggagtag caaaggaggt ggggctctcc | 120 |
| cgcgctgcgt taatccagcg cttcaccaac cgcgatacgc tgctggtgag gatgatggag | 180 |
| cgcggcgtcg agcaggtgcg acattacctg aatgcgatac cgataggcgc agggccgcaa | 240 |
| gggctctggg aattttgca ggtgctcgtt cggagcatga acactcgcaa cgacttctcg | 300 |
| gtgaactatc tcatctcctg gtacgagctc caggtgccgg agctacgcac gcttgcgatc | 360 |
| cagcggaacc gcgcggtggt ggaggggatc cgcaagcgac tgcccccagg tgctcctgcg | 420 |
| gcagctgagt tgctcctgca ctcggtcatc gctggcgcga cgatgcagtg ggccgtcgat | 480 |
| ccggatggtg agctagctga tcatgtgctg gctcagatcg ctgccatcct gtgtttaatg | 540 |
| tttcccgaac acgacgattt ccaactcctc caggcacatg cgtaa | 585 |

<210> SEQ ID NO 12
<211> LENGTH: 585
<212> TYPE: DNA
<213> ORGANISM: Artificial Sequence
<220> FEATURE:
<223> OTHER INFORMATION: synthetic construct

<400> SEQUENCE: 12

| | |
|---|---|
| atgccccgcc ccaagctcaa gtccgatgac gaggtactcg aggccgccac cgtagtgctg | 60 |
| aagcgttgcg gtcccataga gttcacgctc agcggagtag caaaggaggt ggggttctcc | 120 |
| cgcgcagcgt taatccagcg cttcaccaac cgcgatacgc tgctggtgag gatgatggag | 180 |
| cgcggcgtcg agcaggtgcg gcattacctg aatgcgatac cgataggcgc agggccgcaa | 240 |

-continued

```
gggctctggg aattttttgca ggtgctcgtt cggagcatga acactcgcaa cgacttctcg      300
gtgaactatc tcatctcctg gtacgagctc caggtgccgg agctacgcac gcttgcgatc      360
cagcggaacc gcgcggtggt ggaggggatc cgcaagcgac tgcccccagg tgctcctgcg      420
gcagctgagt tgctcctgca ctcggtcatc gctggcgcga cgatgcagtg ggccgtcgat      480
ccggatggtg agctagctga tcatgtgctg gctcagatcg ctgccatcct gtgtttaatg      540
tttcccgaac acgacgattt ccaactcctc caggcacatg cgtaa                      585
```

<210> SEQ ID NO 13
<211> LENGTH: 585
<212> TYPE: DNA
<213> ORGANISM: Artificial Sequence
<220> FEATURE:
<223> OTHER INFORMATION: synthetic construct

<400> SEQUENCE: 13

```
atgccccgcc ccaagctcaa gtccgatgac gaggtactcg aggccgccac cgtagtgctg       60
aagcgttgcg gtcccataga gttcacgctc agcggactag caaaggaggt ggggctctcc      120
cgcgcagcgt taatccagcg cttcaccaac cgcgatacgc tgctggtgag gatgatggag      180
cgcggcgtcg agcaggtgcg gcattacctg aatgcgatac cgataggcgc agggccgcaa      240
gggctctggg aattttttgca ggtgctcgtt cggagcatga acactcgcaa cgacttctcg      300
gtgaactatc tcatctcctg gtacgagctc caggtgccgg agctacgcac ccttgcgatc      360
cagcggaacc gcgcggtggt ggaggggatc cgcaagcgac tgcccccagg tgctcctgcg      420
gcagctgagt tgctcctgca ctcggtcatc gctggcgcga cgatgcagtg ggccgtcgat      480
ccggatggtg agctagctga tcatgtgctg gctcagatct ctgccatcct gtgtttaatg      540
tttcccgaac acgacgattt ccaactcctc caggcacatg cgtaa                      585
```

<210> SEQ ID NO 14
<211> LENGTH: 585
<212> TYPE: DNA
<213> ORGANISM: Artificial Sequence
<220> FEATURE:
<223> OTHER INFORMATION: synthetic construct

<400> SEQUENCE: 14

```
atgccccgcc ccaagctcaa gtccgatgac gaggtactcg aggccgccac cgtagtgctg       60
aagcgttgcg gtcccattga gttcacgctc agcggagtat caaaggaggt ggggctctcc      120
cgcgcagcgt taatccagcg cttcaccaac cgcgatacgc tgctggtgag gatgatggag      180
cgcggcgtcg agcaggtgcg gcattacctg aatgcgatac cgataggcgc agggccgcaa      240
gggctctggg aattttttgca ggtgctcgtt cggagcatga acactcgcaa cgacttctcg      300
gtgaactatc tcatctcctg gtacgagctc caggtgccgg agctacgcac gcttgcgatc      360
cagcggaacc gcgcggtggt ggaggggatc cgcaagcgac tgcccccagg tgctcctgcg      420
gcagcagagt tgctcctgca ctcggtcatc gctggcgcga cgatgcagtg ggccgtcgat      480
ccggatggtg agctagctga tcatgtgctg gctcagatcg ctgccatcct gtgtttaatg      540
tttcccgaac acgacgattt ccaactcctc caggcacatg cgtaa                      585
```

<210> SEQ ID NO 15
<211> LENGTH: 585
<212> TYPE: DNA
<213> ORGANISM: Artificial Sequence
<220> FEATURE:
<223> OTHER INFORMATION: synthetic construct

<400> SEQUENCE: 15

```
atgccccgcc ccaagctcaa gtccgatgac gaggtactcg aggccgccac cgtagtgctg    60
aagcgttgcg gtcccataga gttcacgctc agcggagtag caaaggaggt ggggctctcc   120
cgcgcagcgt taatccagcg cttcaccaac tgcgatacgc tgctggtgag gatgatggag   180
cgcggcgtcg agcaggtgcg gcattacctg aatgcgatac cgataggcgc agggccgcaa   240
gggctctggg aattttttgca ggtgctcgtt cggagcatga acactcgcaa cgacttctcg   300
gtgaactatc tcatctcctg gtacgagctc caggtgccgg agctacgcac gcttgcgatc   360
cagcggaacc gcgcggtggt ggaggggatc cgcaagcgac tgcccccagg tgctcctgcg   420
gcagctgagt tgctcctgca ctcggtcatc gctggcgcga cgatgcagtg ggccgtcgat   480
ccggatggtg agctagctga tcatgtgctg gctcagatcc ctgccatcct gtgtttaatg   540
tttcccgaac acgacgattt ccaactcctc caggcacatg cgtaa               585
```

<210> SEQ ID NO 16
<211> LENGTH: 585
<212> TYPE: DNA
<213> ORGANISM: Artificial Sequence
<220> FEATURE:
<223> OTHER INFORMATION: synthetic construct

<400> SEQUENCE: 16

```
atgccccgcc ccaagctcaa gtccgatgac gaggttctcg aggccaccac cgtagtgctg    60
aagcgttgcg gtcccataga gttcacgctc agtggagtgg caaaggaggt ggggctctcc   120
cgcgcagcgt taatccagcg cttcaccaac cgcgatacgc tgctggtgag gatgatggag   180
cgcggcgtcg agcaggtgcg gcattacctg aatgcgatac cgataggcgc agggccgcaa   240
gggctctggg aattttttgca ggtgctcgtt cggagcatga acactcgcaa cgacttctcg   300
gtgaactatc tcatctcctg gtacgagctc caggtgccgg agctacgcac gcttgcgatc   360
cagcggaacc gcgcggtagt ggaggggatc cgcaagcgac tgcccccagg tgctcctgcg   420
gcagctgagt tgctcctgca ctcggtcatc gctggcgcga tgaagcagtg ggccgtcgat   480
ccggatggtg agctagctga tcatgtgctg gctcagatcc ctgccatcct gtgtttaatg   540
tttcccgaac acgacgattt ccaactcctc caggcacatg cgtaa               585
```

<210> SEQ ID NO 17
<211> LENGTH: 585
<212> TYPE: DNA
<213> ORGANISM: Artificial Sequence
<220> FEATURE:
<223> OTHER INFORMATION: synthetic construct

<400> SEQUENCE: 17

```
atgccccgcc tcaagctcaa gtccgatgac gaggtactcg aggccgccac cgtagtgctg    60
aagcgttgcg gtcccataga gttcacgctc agcggagtag caaaggaggt ggggctctcc   120
cgcgcagcgt taatccagcg cttcaccaac cgcgatacgc tgctggtgag gatgatggag   180
cgcggcgtcg agcaggtgcg gcattacctg aatgcgatac cgataggcgc agggccgcaa   240
gggctctggg aattttttgca ggtgctcgtt cggagcatga acactcgcaa cgacttctcg   300
gtgaactatc tcatctcctt gtacgagctc caggtgccgg agctacgcac gcttgcgatc   360
cagcggaacc gcgcggtggt ggaggggatc cgcaagcgac tgcccccagg tgctcctgcg   420
gcagctgagt tgctcctgca ctcggtcatc gctggcgcga cgatgcagtg ggccgtcgat   480
```

| | |
|---|---|
| ccggatggtg agctagctga tcatgtgctg gctcagatcg ctgccatcct gtgtttaatg | 540 |
| tttcccgaac acgacgattt ccaactcctc caggcacgtg cgtaa | 585 |

<210> SEQ ID NO 18
<211> LENGTH: 585
<212> TYPE: DNA
<213> ORGANISM: Artificial Sequence
<220> FEATURE:
<223> OTHER INFORMATION: synthetic construct

<400> SEQUENCE: 18

| | |
|---|---|
| atgccccgcc ccaagctcaa gtccgatgac gaggtactcg aggccgccac cgtagtgctg | 60 |
| aagcgttgcg gtcccataga gttcacgctc agcggagtat caaaggaggt ggggctctcc | 120 |
| cgcgcagcgt taatccagcg cttcaccaac cgcgatacgc tgctggtgag gatgatggag | 180 |
| cgcggcgtcg agcaggtgcg gcattacctg aatgcgatac cgataggcgc agggccgcaa | 240 |
| gggctctggg aattttttgca ggtgctcgtt cggagcatga acactcgcaa cgacttctcg | 300 |
| gtgaacaatc tcatctcctg gtacgagctc caggtgccgg agctacgcac gcttgcgatc | 360 |
| cagcggaacc gcgcggtggt ggaggggatc cgcaagcgac tgcccccagg tgctcctgcg | 420 |
| gcagctgagt tgctcctgca ctcggtcatc gctggcgcga cgatgcagtg ggccgtcgat | 480 |
| ccggatggtg agctagctga tcatgtgctg gctcagatcg ctgccatcct gtgtttaatg | 540 |
| tttcccgaac acgacgattt ccaattcctc caggcacatg cgtaa | 585 |

<210> SEQ ID NO 19
<211> LENGTH: 585
<212> TYPE: DNA
<213> ORGANISM: Artificial Sequence
<220> FEATURE:
<223> OTHER INFORMATION: synthetic construct

<400> SEQUENCE: 19

| | |
|---|---|
| atgccccgcc ccaagctcaa gtccgatgac gaggtactcg aggccgccac cgtagtgctg | 60 |
| aagcgttgcg gtcccataga gttcacgctc agcggagtag caaaggaggt ggggctctcc | 120 |
| cgcgcagcgt taatccagcg cttcaccaac cgcgatacgc tgctggtgag gatgatggag | 180 |
| cgcggcgtcg agcagccacg gcattacctg aatgcgatac cgataggcgc agggccgcaa | 240 |
| gggctctggg aattttttgca ggtgctcgtt cggagcatga acactcgcaa cgacttctcg | 300 |
| gtgaactatc tcatctcctg gtacgagctc caggtgccgg agctacgcac gcttgcgatc | 360 |
| cagcggaacc gcgcggtggt ggaggggatc cgcaagcgac tgcccccagg tgctcctgcg | 420 |
| gcagctgagt tgctcctgca ctcggtcatc gctggcgcga cgatgcagtg ggccgtcgat | 480 |
| ccggatggtg agctagctga tcatgtgctg gctcagatcg ctgccatcct gtgtttaatg | 540 |
| tttcccgaac acgacgattt ccaactcctc caggcacatg cgtaa | 585 |

<210> SEQ ID NO 20
<211> LENGTH: 585
<212> TYPE: DNA
<213> ORGANISM: Artificial Sequence
<220> FEATURE:
<223> OTHER INFORMATION: synthetic construct

<400> SEQUENCE: 20

| | |
|---|---|
| atgccccgcc ccaagctcaa gtccgatgac gaggtactcg aggccgccac cgtagtgctg | 60 |
| aagcgttgcg gtcccataga gttcacgctc agcggagtag caaaggaggt ggggctctcc | 120 |
| cgcgcagcgt taatccagcg cttcaccaac cgcgatacgc tgctggtgag gatgatggag | 180 |

```
cgcggcgtcg agcagaggcg gcattacctg aatgcgatac cgataggcgc agggccgcaa    240
gggctctggg aattttttgca ggtgctcgtt cggagcatga acactcgcaa cgacttctcg    300
gtgaactatc tcatctcctg gtacgagctc caggtgccgg agctacgcac gcttgcgatc    360
cagcggaacc gcgcggtggt ggaggggatc cgcaagcgac tgcccccagg tgctcctgcg    420
gcagctgagt tgctcctgca ctcggtcatc gctggcgcga cgatgcagtg ggccgtcgat    480
ccggatggtg agctagctga tcatgtgctg gctcagatcg ctgccatcct gtgtttaatg    540
tttcccgaac acgacgattt ccaactcctc caggcacatg cgtaa                    585

<210> SEQ ID NO 21
<211> LENGTH: 585
<212> TYPE: DNA
<213> ORGANISM: Artificial Sequence
<220> FEATURE:
<223> OTHER INFORMATION: synthetic construct

<400> SEQUENCE: 21
atgccccgcc ccaagctcaa gtccgatgac gaggtactcg aggccgccac cgtagtgctg     60
aagcgttgcg gtcccataga gttcacgctc agcggagtag caaaggaggt ggggctctcc    120
cgcgcagcgt taatccagcg cttcaccaac cgcgatacgc tgctggtgag gatgatggag    180
cgcggcgtcg agcagggacg gcattacctg aatgcgatac cgataggcgc agggccgcaa    240
gggctctggg aattttttgca ggtgctcgtt cggagcatga acactcgcaa cgacttctcg    300
gtgaactatc tcatctcctg gtacgagctc caggtgccgg agctacgcac gcttgcgatc    360
cagcggaacc gcgcggtggt ggaggggatc cgcaagcgac tgcccccagg tgctcctgcg    420
gcagctgagt tgctcctgca ctcggtcatc gctggcgcga cgatgcagtg ggccgtcgat    480
ccggatggtg agctagctga tcatgtgctg gctcagatcg ctgccatcct gtgtttaatg    540
tttcccgaac acgacgattt ccaactcctc caggcacatg cgtaa                    585

<210> SEQ ID NO 22
<211> LENGTH: 585
<212> TYPE: DNA
<213> ORGANISM: Artificial Sequence
<220> FEATURE:
<223> OTHER INFORMATION: synthetic construct

<400> SEQUENCE: 22
atgccccgcc ccaagctcaa gtccgatgac gaggtactcg aggccgccac cgtagtgctg     60
aagcgttgcg gtcccataga gttcacgctc agcggagtag caaaggaggt ggggctctcc    120
cgcgcagcgt taatccagcg cttcaccaac cgcgatacgc tgctggtgag gatgatggag    180
cgcggcgtcg agcagatccg gcattacctg aatgcgatac cgataggcgc agggccgcaa    240
gggctctggg aattttttgca ggtgctcgtt cggagcatga acactcgcaa cgacttctcg    300
gtgaactatc tcatctcctg gtacgagctc caggtgccgg agctacgcac gcttgcgatc    360
cagcggaacc gcgcggtggt ggaggggatc cgcaagcgac tgcccccagg tgctcctgcg    420
gcagctgagt tgctcctgca ctcggtcatc gctggcgcga cgatgcagtg ggccgtcgat    480
ccggatggtg agctagctga tcatgtgctg gctcagatcg ctgccatcct gtgtttaatg    540
tttcccgaac acgacgattt ccaactcctc caggcacatg cgtaa                    585

<210> SEQ ID NO 23
<211> LENGTH: 585
<212> TYPE: DNA
```

<213> ORGANISM: Artificial Sequence
<220> FEATURE:
<223> OTHER INFORMATION: synthetic construct

<400> SEQUENCE: 23

```
atgccccgcc ccaagctcaa gtccgatgac gaggtactcg aggccgccac cgtagtgctg    60
aagcgttgcg gtcccataga gttcacgctc agcggagtag caaaggaggt ggggctctcc   120
cgcgcagcgt taatccagcg cttcaccaac cgcgatacgc tgctggtgag gatgatggag   180
cgcggcgtcg agcaggaccg gcattacctg aatgcgatac cgataggcgc agggccgcaa   240
gggctctggg aattttttgca ggtgctcgtt cggagcatga acactcgcaa cgacttctcg   300
gtgaactatc tcatctcctg gtacgagctc caggtgccgg agctacgcac gcttgcgatc   360
cagcggaacc gcgcggtggt ggaggggatc cgcaagcgac tgccccagg tgctcctgcg    420
gcagctgagt tgctcctgca ctcggtcatc gctggcgcga cgatgcagtg ggccgtcgat   480
ccggatggtg agctagctga tcatgtgctg gctcagatcg ctgccatcct gtgtttaatg   540
tttcccgaac acgacgattt ccaactcctc caggcacatg cgtaa                   585
```

<210> SEQ ID NO 24
<211> LENGTH: 585
<212> TYPE: DNA
<213> ORGANISM: Artificial Sequence
<220> FEATURE:
<223> OTHER INFORMATION: synthetic construct

<400> SEQUENCE: 24

```
atgccccgcc ccaagctcaa gtccgatgac gaggtactcg aggccgccac cgtagtgctg    60
aagcgttgcg gtcccataga gttcacgctc agcggagtag caaaggaggt ggggctctcc   120
cgcgcagcgt taatccagcg cttcatcaac cgcgatacgc tgctggtgag gatgatggag   180
cgcggcgtcg agcaggtgcg gcattacctg aatgcgatac cgataggcgc agggccgcaa   240
gggctctggg aattttttgca ggtgttcgtt cggagcatga acactcgcaa caacttctcg   300
gtgaactatc tcatctcctg gtacgatctc caggtgccgg agctacgcac gcttgcgatc   360
cagcggaacc gcgcggtggt ggaggggatc cgcaagcgac tgccccagg tgctcctgcg    420
gcagctgagt tgctcctgca ctcggtcatc gctggcgcga cgatgcagtg ggccgtcgat   480
ccggatggtg agctagctga tcatgtgctg gctcagatcg ctgccatcct gtgtttaatg   540
tttcccgaac acgacgattt ccaactcctc caggcacatg cgtaa                   585
```

<210> SEQ ID NO 25
<211> LENGTH: 3897
<212> TYPE: DNA
<213> ORGANISM: Artificial Sequence
<220> FEATURE:
<223> OTHER INFORMATION: synthetic construct

<400> SEQUENCE: 25

```
tctagtgtac agtgatcaag acttcgatac caccgaccgt accggtacta atcgacgacg    60
gtcgtgttcg tcgcctgccg cagggactct gcacacctcc gtttacgcat gtgcctggag   120
gagttggaaa tcgtcgtgtt cggaaacat taaacacagg atggcagcga tctgagccag    180
cacatgatca gctagctcac catccggatc gacgcccac tgcatcgtcg cgccagcgat    240
gaccgagtgc aggagcaact cagctgccgc aggagcacct gggggcagtc gcttgcggat   300
cccctccacc accgcgcggt tccgctggat cgcaagcgtg cgtagctccg gcacctggag   360
ctcgtaccag gagatgagat agttcaccga gaagtcgttg cgagtgttca tgctccgaac   420
```

```
gagcacctgc aaaaattccc agagcccttg cggccctgcg cctatcggta tcgcattcag    480
gtaatgccgc acctgctcga cgccgcgctc catcatcctc accagcagcg tatcgcggtt    540
ggtgaagcgc tggattaacg ctgcgcggga gagccccacc tcctttgcta ctccgctgag    600
cgtgaactct atgggaccgc aacgcttcag cactacggtg gcggcctcga gtacctcgtc    660
atcggacttg agcttggggc ggggcatcag tgttcacctt ctgtatgggt tgggggggcgc    720 tatcatgcca taccgcgaaa ggttttgcac catctagagc gcaacgcaat taatgtgagt    780
tagctcactc attaggcacc ccaggcttta cactttatgc ttccggctcg tatgttgtgt    840
gggattgaat ataaccgacg tgactgttac atttaggtgg gctaacagga ggaaactagt    900
atgagtaaag gagaagaact tttcactgga gttgtcccaa ttcttgttga attagatggt    960
aaacttaccc ttaaatttat ttgcactact ggaaaactac ctgttccatg gccaacactt    1020
gtcactactt tctcttatgg tgttcaatgc ttttcccgtt atccggatca tatgaaacgg    1080
catgactttt tcaagagtgc catgcccgaa ggttatgtac aggaacgcac tatatctttc    1140
aaagatgacg ggaactacaa gacgcgtgct gaagtcaagt ttgaaggtga taccttgtt    1200 aatcgtatcg agttaaaagg tattgatttt aagaagatg gaaacattct cggacacaaa    1260
ctcgagtaca actataactc acacaatgta tacatcacgg cagacaaaca aaagaatgga    1320
atcaaagcta acttcaaaat tcgccacaac attgaagatg gatccgttca actagcagac    1380
cattatcaac aaaatactcc aattggcgat ggccctgtcc ttttaccaga caaccattac    1440
ctgtcgacac aatctgccct ttcgaaagat cccaacgaaa agcgtgacca catggtcctt    1500
cttgagtttg taactgctgc tgggattaca catggcatgg atgagctcta caataagct    1560 tgggcccgaa caaaaactca tctcagaaga ggatctgaat agcgccgtcg accatcatca    1620
tcatcatcat tgagtttaaa cggtctccag cttggctgtt ttggcggatg agagaagatt    1680
ttcagcctga tacagattaa atcagaacgc agaagcggtc tgataaaaca gaatttgcct    1740
ggcggcagta gcgcggtggt cccacctgac cccatgccga actcagaagt gaaacgccgt    1800
agcgccgatg gtagtgtggg gtctccccat gcgagagtag ggaactgcca ggcatcaaat    1860
aaaacgaaag gctcagtcga aagactgggc ctttcgtttt atctgttgtt tgtcggtgaa    1920
cgctctcctg agtaggacaa atccgccggg agcggatttg aacgttgcga agcaacggcc    1980
cggagggtgg cgggcaggac gcccgccata aactgccagg catcaaatta gcagaaggc    2040 catcctgacg gatggccttt ttgcgtttct acaaactctt tttgtttatt tttctaaata    2100
cattcaaata tgtatccgct catgagacaa taaccctgat aaatgcttca ataatattga    2160
aaaaggaaga gtatgagtat tcaacatttc cgtgtcgccc ttattccctt ttttgcggca    2220
ttttgccttc ctgtttttgc tcacccagaa acgctggtga agtaaaagat gctgaagat    2280 cagttgggtg cacgagtggg ttacatcgaa ctggatctca acagcggtaa gatccttgag    2340
agttttcgcc ccgaagaacg ttttccaatg atgagcactt taaagttct gctatgtggc    2400 gcggtattat cccgtgttga cgccgggcaa gagcaactcg gtcgccgcat acactattct    2460
cagaatgact tggttgagta ctcaccagtc acagaaaagc atcttacgga tggcatgaca    2520
gtaagagaat tatgcagtgc tgccataacc atgagtgata acactgcggc caacttactt    2580
ctgacaacga tcggaggacc gaaggagcta accgcttttt tgcacaacat ggggatcat    2640 gtaactcgcc ttgatcgttg ggaaccggag ctgaatgaag ccataccaaa cgacgagcgt    2700
gacaccacga tgcctgtagc aatggcaaca acgttgcgca aactattaac tggcgaacta    2760
```

-continued

```
cttactctag cttcccggca acaattaata gactggatgg aggcggataa agttgcagga    2820
ccacttctgc gctcggccct tccggctggc tggtttattg ctgataaatc tggagccggt    2880
gagcgtgggt ctcgcggtat cattgcagca ctggggccag atggtaagcc ctcccgtatc    2940
gtagttatct acacgacggg gagtcaggca actatggatg aacgaaatag acagatcgct    3000
gagataggtg cctcactgat taagcattgg taactgtcag accaagttta ctcatatata    3060
ctttagattg atttaaaact tcattttttaa tttaaaagga tctaggtgaa gatccttttt    3120
gataatctca tgaccaaaat cccttaacgt gagttttcgt tccactgagc gtcagacccc    3180
gtagaaaaga tcaaaggatc ttcttgagat cctttttttc tgcgcgtaat ctgctgcttg    3240
caaacaaaaa aaccaccgct accagcggtg gtttgtttgc cggatcaaga gctaccaact    3300
ctttttccga aggtaactgg cttcagcaga gcgcagatac caaatactgt ccttctagtg    3360
tagccgtagt taggccacca cttcaagaac tctgtagcac cgcctacata cctcgctctg    3420
ctaatcctgt taccagtggc tgctgccagt ggcgataagt cgtgtcttac cgggttggac    3480
tcaagacgat agttaccgga taaggcgcag cggtcgggct gaacggggg ttcgtgcaca    3540 cagcccagct tggagcgaac gacctacacc gaactgagat acctacagcg tgagctatga    3600
gaaagcgcca cgcttcccga agggagaaag gcggacaggt atccggtaag cggcagggtc    3660
ggaacaggag agcgcacgag ggagcttcca ggggaaacg cctggtatct ttatagtcct    3720 gtcgggttc gccacctctg acttgagcgt cgatttttgt gatgctcgtc aggggggcgg    3780
agcctatgga aaacgccag caacgcggcc ttttacggtt cctggccttt tgctggcct    3840 tttgctcaca tgttctttcc tgcgttatcc cctgattctg tggataaccg tattacc      3897
```

<210> SEQ ID NO 26
<211> LENGTH: 5131
<212> TYPE: DNA
<213> ORGANISM: Artificial Sequence
<220> FEATURE:
<223> OTHER INFORMATION: synthetic construct

<400> SEQUENCE: 26

```
tcattccgct gttatggccg cgtttgtctc attccacgcc tgacactcag ttccgggtag     60
gcagttcgct ccaagctgga ctgtatgcac gaaccccccg ttcagtccga ccgctgcgcc    120
ttatccggta actatcgtct tgagtccaac ccggaaagac atgcaaaagc accactggca    180
gcagccactg gtaattgatt tagaggagtt agtcttgaag tcatgcgccg gttaaggcta    240
aactgaaagg acaagttttg gtgactgcgc tcctccaagc cagttacctc ggttcaaaga    300
gttggtagct cagagaacct cgaaaaacc gccctgcaag gcggtttttt cgttttcaga    360
gcaagagatt acgcgcagac caaaacgatc tcaagaagat catcttatta atcagataaa    420
atatttctag atttcagtgc aatttatctc ttcaaatgta gcacctgaag tcagccccat    480
acgatataag ttgtaattct catgtttgac agcttatcat cgataagctt taatgcggta    540
gtttatcaca gttaaattgc taacgcagtc aggcaccgtg tatgaaatct aacaatgcgc    600
tcatcgtcat cctcggcacc gtcaccctgg atgctgtagg cataggcttg gttatgccgg    660
tactgccggg cctcttgcgg gatatcgtcc attccgacag catcgccagt cactatggcg    720
tgctgctagc gctatatgcg ttgatgcaat ttctatgcgc accgttctc ggagcactgt    780 ccgaccgctt tggccgccgc ccagtcctgc tcgcttcgct acttggagcc actatcgact    840
acgcgatcat ggcgaccaca cccgtcctgt ggatcctcta cgccggacgc atcgtggccg    900
gcatcaccgg cgccacaggt gcggttgctg gcgcctatat cgccgacatc accgatgggg    960
```

-continued

```
aagatcgggc tcgccacttc gggctcatga gcgcttgttt cggcgtgggt atggtggcag    1020
gccccgtggc cgggggactg ttgggcgcca tctccttgca tgcaccattc cttgcggcgg    1080
cggtgctcaa cggcctcaac ctactactgg gctgcttcct aatgcaggag tcgcataagg    1140
gagagcgtcg accgatgccc ttgagagcct tcaacccagt cagctccttc cggtgggcgc    1200
ggggcatgac tatcgtcgcc gcacttatga ctgtcttctt tatcatgcaa ctcgtaggac    1260
aggtgccggc agcgctctgg gtcattttcg gcgaggaccg cttctgctgg agcgcgacga    1320
tgatcggcct gtcgcttgcg gtattcggaa tcttgcacgc cctcgctcaa gccttcgtca    1380
ctggtcccgc caccaaacgt ttcggcgaga agcaggccat tatcgccggc atggcggccg    1440
acgcgctggg ctacgtcttg ctggcgttcg cgacgcgagg ctggatggcc ttccccatta    1500
tgattcttct cgcttccggc ggcatcggga tgcccgcgtt gcaggccatg ctgtccaggc    1560
aggtagatga cgaccatcag ggacagcttc aaggatcgct cgcggctctt accagcctaa    1620
cttcgatcac tggaccgctg atcgtcacgg cgatttatgc cgcctcggcg agcacatgga    1680
acgggttggc atggattgta ggcgccgccc tataccttgt ctgcctcccc gcgttgcgtc    1740
gcggtgcatg gagccgggcc acctcgacct gaatggaagc cggcggcacc tcgctaacgg    1800
attcaccact ccaagaattg gagccaatca attcttgcgg agaactgtga atgcgcaaac    1860
caacccttgg cagaacatat ccatcgcgtc cgccatctcc agcagccgca cgcggcgcat    1920
ctcgggcagc gttgggtcct ggccacgggt gcgcatgatc gtgctcctgt cgttgaggac    1980
ccggctaggc tggcggggtt gccttactgg ttagcagaat gaatcaccga tacgcgagcg    2040
aacgtgaagc gactgctgct gcaaaacgtc tgcgacctga gcaacaacat gaatggtctt    2100
cggtttccgt gtttcgtaaa gtctggaaac gcggaagtcc cctacgtgct gctgaagttg    2160
cccgcaacag agagtggaac cggtacccgg ggatcctcta gagtcgacct gcaggagatg    2220
ctggctgaac gcggagtgaa tgtcgatcac tccacgattt accgctgggt tcagcgttat    2280
gcgcctgaaa tggaaaaacg gctgcgctgg tactggcgta acccttccga tctttgcccg    2340
tggcacatgg atgaaaccta cgtgaaggtc aatggccgct gggcgtatct gtaccgggcc    2400
gtcgacagcc ggggccgcac tgtcgatttt tatctctcct cccgtcgtaa cagcaaagct    2460
gcataccggt ttctgggtaa aatcctcaac aacgtgaaga agtggcagat cccgcgattc    2520
atcaacacgg ataaagcgcc cgcctatggt cgcgcgcttg ctctgctcaa cgcgaaggc    2580 cggtgcccgt ctgacgttga acaccgacag attaagtacc ggaacaacgt gattgaatgc    2640
gatcatggca aactgaaacg gataatcggc gccacgctgg gatttaaatc catgaagacg    2700
gcttacgcca ccatcaaagg tattgaggtg atgcgtgcac tacgcaaagg ccaggcctca    2760
gcattttatt atggtgatcc cctgggcgaa atgcgcctgg taagcagagt ttttgaaatg    2820
taaggccttt gaataagaca aaaggctgcc tcatcgctaa cttttgcaaca gtgccggatt    2880 gaatataacc gacgtgactg ttacatttag gtggctaaac ccgtcaagcc ctcaggagtg    2940
aatcatgacc gtagtcacga ccgccgatac ctcccaactg tacgcacttg cagcccgaca    3000
tgggctcaag ctccatggcc cgctgactgt caatgagctt gggctcgact ataggatcgt    3060
gatcgccacc gtcgacgatg gacgtcgtg ggtgctgcgc atcccgcgcc gagccgaggt    3120
aagcgcgaag gtcgaaccag aggcgcgggt gctggcaatg ctcaagaatc gcctgccgtt    3180
cgcggtgccg gactggcgcg tggccaacgc cgagctcgtt gcctatccca tgctcgaaga    3240
ctcgactgcg atggtcatcc agcctggttc gtccacgccc gactgggtcg tgccgcagga    3300
```

```
ctcggaggtc ttcgcggaga gcttcgcgac cgcgctcgcc gccctgcatg ccgtccccat    3360
ttccgccgcc gtggatgcgg ggatgctcat ccgtacaccg acgcaggccc gtcagaaggt    3420
ggccgacgac gttgaccgcg tccgacgcga gttcgtggtg aacgacaagc gcctccaccg    3480
gtggcagcgc tggctcgacg acgattcgtc gtggccagat ttctccgtgg tggtgcatgg    3540
cgatctctac gtgggccatg tgctcatcga caacacggag cgcgtcagcg ggatgatcga    3600
ctggagcgag gcccgcgttg atgaccctgc catcgacatg gccgcgcacc ttatggtctt    3660
tggtgaagag gggctcgcga agctcctcct cacgtatgaa gcggccggtg gccgggtgtg    3720
gccgcggctc gcccaccaca tcgcggagcg ccttgcgttc ggggcggtca cctacgcact    3780
cttcgccctc gactcgggta acgaagagta cctcgctgcg gcgaaggcgc agctcgccgc    3840
agcggaatga gcgaacgtcg atatagcccg ctcgcgacgc tgttcgcggc gacctttctc    3900
ttccggatcg gcaacgcggt ggcggccctc gcgcttccat ggttcgtcct gtctcataca    3960
aagagcgcgg cctgggcggg cgccacggcc gctagcagcg tcatcgcgac catcatcggc    4020
gcgtgggttg gtggtggcct cgtcgatcgg ttcgggcgcg cgcccgtcgc attgatctcg    4080
ggtgtggtgg gcggcgtggc catggcgagc atcccactgc tcgatgccgt tggcgccctc    4140
tcgaacactg ggctgatcgc ttgcgtggtg ctcggtgccg cgttcgacgc acccggtatg    4200
gccgcgcagg acagtgagct gcccaaactc ggccacgtcg ccgggctctc cgttgagcgc    4260
gtctcgtcac tgaaagcggt gatcgggaac gtcgcgattc taggtggccc ggcccttggg    4320
ggggccgcaa tcggcctgct tggcgctgcg ccaacgctcg ggctgacggc gttctgctcc    4380
gtccttgcag gtctgctcgg cgcgtgggtg cttcccgcgc gtgccgctcg gacgatgacc    4440
acgacggcga ctctctccat gcgcgccggc gtcgcttttc tctggagcga acccctgctg    4500
cgccctctct ttggtatagt gatgatcttc gtgggcatcg ttggcgccaa cggcagcgtc    4560
atcatgcctg cgctgtttgt agatgcagga cgccaagtag cagagctcgg gctgttctcc    4620
tcaatgatgg gggctggtgg tctccttggc tgtccctcct gttcagctac tgacggggtg    4680
gtgcgtaacg gcaaaagcac cgccggacat cagcgctagc ggagtgtata ctggcttact    4740
atgttggcac tgatgagggt gtcagtgaag tgcttcatgt ggcaggagaa aaaaggctgc    4800
accggtgcgt cagcagaata tgtgatacag gatatattcc gcttcctcgc tcactgactc    4860
gctacgctcg gtcgttcgac tgcggcgagc ggaaatggct tacgaacggg gcggagattt    4920
cctggaagat gccaggaaga tacttaacag ggaagtgaga gggccgcggc aaagccgttt    4980
ttccataggc tccgcccccc tgacaagcat cacgaaatct gacgctcaaa tcagtggtgg    5040
cgaaacccga caggactata aagataccag gcgtttcccc ctggcggctc cctcgtgcgc    5100
tctcctgttc ctgcctttcg gtttaccggt g                                  5131
```

<210> SEQ ID NO 27
<211> LENGTH: 30
<212> TYPE: DNA
<213> ORGANISM: Artificial Sequence
<220> FEATURE:
<223> OTHER INFORMATION: synthetic construct

<400> SEQUENCE: 27
aatataaccg acgtgactgt tacatttagg                                      30

<210> SEQ ID NO 28
<211> LENGTH: 600
<212> TYPE: DNA
<213> ORGANISM: Artificial Sequence
<220> FEATURE:
<223> OTHER INFORMATION: synthetic construct

<400> SEQUENCE: 28

```
agaaggtgaa cactgatgcc ccgccccaag ctcaagtccg atgacgaggt actcgaggcc     60
gccaccgtag tgctgaagcg ttgcggtccc atagagttca cgctcagcgg agtagcaaag    120
gaggtggggc tctcccgcgc agcgttaatc cagcgcttca ccaaccgcga tacgctgctg    180
gtgaggatga tggagcgcgg cgtcgagcag gtgcggcatt acctgaatgc gataccgata    240
ggcgcagggc cgcaagggct ctgggaattt ttgcaggtgc tcgttcggag catgaacact    300
cgcaacgact tctcggtgaa ctatctcatc tcctggtacg agctccaggt gccggagcta    360
cgcacgcttg cgatccagcg gaaccgcgcg gtggtggagg ggatccgcaa gcgactgccc    420
ccaggtgctc ctgcggcagc tgagttgctc ctgcactcgg tcatcgctgg cgcgacgatg    480
cagtgggccg tcgatccgga tggtgagcta gctgatcatg tgctggctca gatcgctgcc    540
atcctgtgtt taatgtttcc cgaacacgac gatttccaac cctccaggc acatgcgtaa     600
```

<210> SEQ ID NO 29
<211> LENGTH: 600
<212> TYPE: DNA
<213> ORGANISM: Artificial Sequence
<220> FEATURE:
<223> OTHER INFORMATION: synthetic construct

<400> SEQUENCE: 29

```
ggaaggtgaa cactgatgcc ccgccccaag ctcaagtccg atgacgaggt actcgaggcc     60
gccaccgtag tgctgaagcg ttgcggtccc atagagttca cgctcagcgg agtagcaaag    120
gaggtggggc tctcccgcgc agcgttaatc cagcgcttca ccaaccgcga tacgctgctg    180
gtgaggatga tggagcgcgg cgtcgagcag gtgcggcatt acctgaatgc gataccgata    240
tgcgcagggc cgcaagggct ctgggaattt ttgcaggtgc tcgttcggag catgaacact    300
cgcaacgact tctcggtgaa ctatctcatc tcctggtacg agctccaggt gccggagcta    360
cgcacgcttg cgatccagcg gaaccgcgcg gtggtggagg ggatccgcaa gcgactgccc    420
ccaggtgctc ctgcggcagc tgagttgctc ctgcactcgg tcatcgctgg cgcgacgatg    480
cagtgggccg tcgatccgga tggtgagcta gctgatcatg tgctggctca gatcgctgcc    540
atcctgtgtt taatgtttcc cgaacacgac gatttccaac cctccaggc acatgcgtaa     600
```

<210> SEQ ID NO 30
<211> LENGTH: 600
<212> TYPE: DNA
<213> ORGANISM: Artificial Sequence
<220> FEATURE:
<223> OTHER INFORMATION: synthetic construct

<400> SEQUENCE: 30

```
agatggtgaa cactgatgcc ccgccccaag ctcaagtccg atgacgaggt actcgaggcc     60
gccaccgtag tgctgaagcg ttgcggtccc atagagttca cgctcagcgg agtagcaaag    120
gaggtggggc tctcccgcgc agcgttaatc cagcgcttca ccaaccgcga tacgctgctg    180
gtgaggatga tggagcgcgg cgtcgagcag gtgcggcatt accttaatgc gataccgata    240
ggcgcagggc cgcaagggct ctgggaattt ttgcaggtgc tcattcggag catgaacact    300
cgcaacgact tctcggtgaa ctatctcatc tcctggtacg agctccaggt gccggagcta    360
cgcacgcttg cgatccagcg gaaccgcgcg gtggtggagg ggatccgcaa gcgactgccc    420
```

```
ccaggtgctc ctgcggcagc tgagttgctc ctgcactcgg tcatcgctgg cgcgacgatg    480
cagtgggccg tcgatccgga tggtgagcta gctgatcatg tgctggctca gatcgctgcc    540
atcctgtgtt taatgtttcc cgaacacgac gatttccaac tcctccaggc acatgcgtaa    600

<210> SEQ ID NO 31
<211> LENGTH: 600
<212> TYPE: DNA
<213> ORGANISM: Artificial Sequence
<220> FEATURE:
<223> OTHER INFORMATION: synthetic construct

<400> SEQUENCE: 31
ggaaggtgaa cactgatgcc cgccccaag ctcaagtccg atgacgaggt actcgaggcc     60
gccaccgtag tgctgaagcg ttgcggtccc atagagttca cgctcagcgg agtagcaaag    120
gaggtggggc tctcccgcgc agcgttaatc cagcgcttca ccaaccgcga tacgctgctg    180
gtgaggatga tggagcgcgg cgtcgagcag gtgcggcatt acctgaatgc gataccgata    240
ggcgcagggc cgcaagggct ctgggaattt ttgcaggtgc tcgttcggag catgaacact    300
cgcaacgact tctcggtgaa ctatctcatc tcctggtacg agctccaggt gccggagcta    360
cgcacgcttg cgatccagcg gaaccgcgcg gtggtggagg ggatccgcaa gcgactgccc    420
ccaggtgctc ctgcggcagc tgagttgctc ctgcactcgg tcatcgctgg cgcgacgatg    480
cagtgggccg tcgatccgga tggtgagcta gctgatcatg tgctggctca gatcgctgcc    540
atcctgtgtt taatgtttcc cgaacacgac gatttccaac tcctccaggc acatgcgtaa    600

<210> SEQ ID NO 32
<211> LENGTH: 600
<212> TYPE: DNA
<213> ORGANISM: Artificial Sequence
<220> FEATURE:
<223> OTHER INFORMATION: synthetic construct

<400> SEQUENCE: 32
agatggtgaa cactgatgcc cgccccaag ctcaagtccg atgacgaggt actcgaggcc     60
gccaccgtag tgctgaagcg ttgcggtccc atagagttca cgctcagcgg agtagcaaag    120
gaggtggggc tctcccgcgc agcgttaatc cagcgcttca ccaaccgcga tacgctgctg    180
gtgaggatga tggagcgcgg cgtcgagcag gtgcggcatt acctgaatgc gataccgata    240
ggcgcagggc cgcaagggct ctgggaattt ttgcaggtgc tcgttcggag catgaacact    300
cgcaacgact tctcggtgaa ctatctcatc tcctggtacg agctccaggt gccggagcta    360
cgcacgcttg cgatccagcg gaaccgcgcg gtggtggagg ggatccgcaa gcgactgccc    420
ccaggtgctc ctgcggcagc tgagttgctc ctgcactcgg tcatcgctgg cgcgacgatg    480
cagtgggccg tcgatccgga tggtgagcta gctgatcatg tgctggctca gatcgctgcc    540
atcctgtgtt taatgtttcc cgaacacgac gatttccaac tcctccaggc acatgcgtaa    600

<210> SEQ ID NO 33
<211> LENGTH: 600
<212> TYPE: DNA
<213> ORGANISM: Artificial Sequence
<220> FEATURE:
<223> OTHER INFORMATION: synthetic construct

<400> SEQUENCE: 33
agaaggcgaa cactgatgcc cgccccaag ctcaagtccg atgacgaggt actcgaggcc     60
gccaccgtag tgctgaagcg ttgcggtccc atagagttca cgctcagcgg agtagcaaag    120
```

```
gaggtggggc tctcccgcgc agcgttaatc cagcgcttca ccaaccgcga tacgctgctg    180
gtgaggatga tggagcgcgg cgtcgagcag gtgcggcatt acctgaatgc gataccgata    240
ggcgcagggc cgcaagggct ctgggaattt ttgcaggtgc tcgttcggag catgaacact    300
cgcaacgact tctcggtgaa ctatctcatc tcctggtacg agctccaggt gccggagcta    360
cgcacgcttg cgatccagcg gaaccgcgcg gtggtggagg ggatccgcaa gcgactgccc    420
ccaggtgctc ctgcggcagc tgagttgctc ctgcactcgg tcatcgctgg cgcgacgatg    480
cagtgggccg tcgatccgga tggtgagcta gctgatcatg tgctggctca gatcgctgcc    540
atcctgtgtt taatgtttcc cgaacacgac gatttccaac tcctccaggc acatgcgtaa    600
```

<210> SEQ ID NO 34
<211> LENGTH: 600
<212> TYPE: DNA
<213> ORGANISM: Artificial Sequence
<220> FEATURE:
<223> OTHER INFORMATION: synthetic construct

<400> SEQUENCE: 34

```
agaaggtgaa cactgatgcc ccgccccaag ctcaagtccg atgacgaggt actcgaggcc     60
gccagggtag tgctgaagcg ttgcggtccc atagagttca cgctcagcgg agtagcaaag    120
gaggtggggc tctcccgcgc agcgttaatc cagcgcttca ccaaccgcga tacgctgctg    180
gtgaggatga tggagcgcgg cgtcgagcag gtgcggcatt acctgaatgc gataccgata    240
ggcgcagggc cgcaagggct ctgggaattt ttgcaggtgc tcgttcggag catgaacact    300
cgcaacgact tctcggtgaa ctatctcatc tcctggtacg agctccaggt gccggagcta    360
cgcacgcttg cgatccagcg gaaccgcgcg gtggtggagg ggatccgcaa gcgactgccc    420
ccaggtgctc ctgcggcagc tgagttgctc ctgcactcgg tcatcgctgg cgcgacgatg    480
cagtgggccg tcgatccgga tggtgagcta gctgatcatg tgctggctca gatcgctgcc    540
atcctgtgtt taatgtttcc cgaacacgac gatttccaac tcctccaggc acatgcgtaa    600
```

<210> SEQ ID NO 35
<211> LENGTH: 600
<212> TYPE: DNA
<213> ORGANISM: Artificial Sequence
<220> FEATURE:
<223> OTHER INFORMATION: synthetic construct

<400> SEQUENCE: 35

```
agaaggtgaa cactgatgcc ccgccccaag ctcaagtccg atgacgaggt actcgaggcc     60
gccgcggtag tgctgaagcg ttgcggtccc atagagttca cgctcagcgg agtagcaaag    120
gaggtggggc tctcccgcgc agcgttaatc cagcgcttca ccaaccgcga tacgctgctg    180
gtgaggatga gtgagcgcgg cgtcgagcag gtgcggcatt acctgaatgc gataccgata    240
ggcgcagggc cgcaagggct ctgggaattt ttgcaggtgc tcgttcggag catgaacact    300
cgcaacgact tctcggtgaa ctatctcatc tcctggtacg agctccaggt gccggagcta    360
cgcacgcttg cgatccagcg gaaccgcgcg gtggtggagg ggatccgcaa gcgactgccc    420
ccaggtgctc ctgcggcagc tgagttgctc ctgcactcgg tcatcgctgg cgcgacgatg    480
cagtgggccg tcgatccgga tggtgagcta gctgatcatg tgctggctca gatcgctgcc    540
atcctgtgtt taatgtttcc cgaacacgac gatttccaac tcctccaggc acatgcgtaa    600
```

<210> SEQ ID NO 36

```
<211> LENGTH: 600
<212> TYPE: DNA
<213> ORGANISM: Artificial Sequence
<220> FEATURE:
<223> OTHER INFORMATION: synthetic construct

<400> SEQUENCE: 36
agaaggtgaa cactgatgcc ccgccccaag ctcaagtccg atgacgaggt actcgaggcc    60
gccggtgtag tgctgaagcg ttgcggtccc atagagttca cgctcagcgg agtagcaaag   120
gaggtggggc tctcccgcgc agcgttaatc cagcgcttca ccaaccgcga tacgctgctg   180
gtgaggatga tggagcgcgg cgtcgagatg gttcggcatt acctgaatgc gataccgata   240
ggcgcagggc cgcaagggct ctgggaattt ttgcaggtgc tcgttcggag catgaacact   300
cgcaacgact tctcggtgaa ctatctcatc tcctggtacg agctccaggt gccggagcta   360
cgcacgcttg cgatccagcg gaaccgcgcg gtggtggagg ggatccgcaa gcgactgccc   420
ccaggtgctc ctgcggcagc tgagttgctc ctgcactcgg tcatcgctgg cgcgacgatg   480
cagtgggccg tcgatccgga tggtgagcta gctgatcatg tgctggctca gatcgctgcc   540
atcctgtgtt taatgtttcc cgaacacgac gatttccaac tcctccaggc acatgcgtaa   600

<210> SEQ ID NO 37
<211> LENGTH: 600
<212> TYPE: DNA
<213> ORGANISM: Artificial Sequence
<220> FEATURE:
<223> OTHER INFORMATION: synthetic construct

<400> SEQUENCE: 37
agaaggtgaa cactgatgcc ccgccccaag ctcaagtccg atgacgaggt actcgaggcc    60
gccgctgtag tgctgaagcg ttgcggtccc atagagttca cgctcagcgg agtagcaaag   120
gaggtggggc tctcccgcgc agcgttaatc cagcgcttca ccaaccgcga tacgctgctg   180
gtgaggatgg aggagcgcgg cgtcgagcag gtgcggcatt acctgaatgc gataccgata   240
ggcgcagggc cgcaagggct ctgggaattt ttgcaggtgc tcgttcggag catgaacact   300
cgcaacgact tctcggtgaa ctatctcatc tcctggtacg agctccaggt gccggagcta   360
cgcacgcttg cgatccagcg gaaccgcgcg gtggtggagg ggatccgcaa gcgactgccc   420
ccaggtgctc ctgcggcagc tgagttgctc ctgcactcgg tcatcgctgg cgcgacgatg   480
cagtgggccg tcgatccgga tggtgagcta gctgatcatg tgctggctca gatcgctgcc   540
atcctgtgtt taatgtttcc cgaacacgac gatttccaac tcctccaggc acatgcgtaa   600

<210> SEQ ID NO 38
<211> LENGTH: 600
<212> TYPE: DNA
<213> ORGANISM: Artificial Sequence
<220> FEATURE:
<223> OTHER INFORMATION: synthetic construct

<400> SEQUENCE: 38
agaaggtgaa cactgatgcc ccgccccaag ctcaagtccg atgacgaggt actcgaggcc    60
gccaccgtag tgctgaagcg ttgcggtccc atagagttca cgctcagcgg agtagcaaag   120
gaggtggggc tctcccgcgc agcgttaatc cagcgcttca ccaaccgcga tacgctgctg   180
gtgaggatga tggagcgcgg cgtcgagcag gtgcggcatt acctgaatgc gataccgata   240
ggcgcagggc cgcaagggct ctgggaattt ttgcaggtgc tcgttcggag catgaacact   300
cgcaacgact tctcggtgaa ctatctcatc ttctggtacg agctccaggt gccggagcta   360
```

```
cgcacgcttg cgatccagcg gaaccgcgcg gtggtggagg ggatccgcaa gcgactgccc    420
ccaggtgctc ctgcggcagc tgagttgctc ctgcactcgg tcatcgctgg cgcgacgatg    480
cagtgggccg tcgatccgga tggtgagcta gctgatcatg tgctggctca gatcgctgcc    540
atcctgtgtt taatgtttcc cgaacacgac gatttccaac tcctccaggc acatgcgtaa    600
```

<210> SEQ ID NO 39
<211> LENGTH: 650
<212> TYPE: DNA
<213> ORGANISM: Artificial Sequence
<220> FEATURE:
<223> OTHER INFORMATION: synthetic construct

<400> SEQUENCE: 39

```
tggtgcaaaa cctttcgcgg tatgacatga tagcgcctcc cagcccatac agaaggtgaa     60
cactgatgcc ccgccccaag ctcaagtccg atgacgaggt actcgaggcc gccaccgtag    120
tgctgaagcg ttgcggtccc atagagttca cgctcagagg agtagcaaag gaggtggggc    180
tctcccgcgc tgcgttaatc cagcgcttca ccaaccgcga tacgctgctg gtgaggatga    240
tggagcgcgg cgtcgagcag gtgcgacatt acctgaatgc gataccgata ggcgcagggc    300
cgcaagggct ctgggaattt ttgcaggtgc tcgttcggag catgaacact cgcaacgact    360
tctcggtgaa ctatctcatc tcctggtacg agctccaggt gccggagcta cgcacgcttg    420
cgatccagcg gaaccgcgcg gtggtggagg ggatccgcaa gcgactgccc ccaggtgctc    480
ctgcggcagc tgagttgctc ctgcactcgg tcatcgctgg cgcgacgatg cagtgggccg    540
tcgatccgga tggtgagcta gctgatcatg tgctggctca gatcgctgcc atcctgtgtt    600
taatgtttcc cgaacacgac gatttccaac tcctccaggc acatgcgtaa               650
```

<210> SEQ ID NO 40
<211> LENGTH: 650
<212> TYPE: DNA
<213> ORGANISM: Artificial Sequence
<220> FEATURE:
<223> OTHER INFORMATION: synthetic construct

<400> SEQUENCE: 40

```
tggtgcaaaa cctttcgcga tatggcatga tagcgccccc caacccatac agaaggtgaa     60
ctctgatgcc ccgccccaag ctcaagtccg atgacgaggt actcgaggcc gccaccgtag    120
tgctgaagcg ttgcggtccc atagagttca cgctcagcgg agtagcaaag gaggtggggt    180
tctcccgcgc agcgttaatc cagcgcttca ccaaccgcga tacgctgctg gtgaggatga    240
tggagcgcgg cgtcgagcag gtgcggcatt acctgaatgc gataccgata ggcgcagggc    300
cgcaagggct ctgggaattt ttgcaggtgc tcgttcggag catgaacact cgcaacgact    360
tctcggtgaa ctatctcatc tcctggtacg agctccaggt gccggagcta cgcacgcttg    420
cgatccagcg gaaccgcgcg gtggtggagg ggatccgcaa gcgactgccc ccaggtgctc    480
ctgcggcagc tgagttgctc ctgcactcgg tcatcgctgg cgcgacgatg cagtgggccg    540
tcgatccgga tggtgagcta gctgatcatg tgctggctca gatcgctgcc atcctgtgtt    600
taatgtttcc cgaacacgac gatttccaac tcctccaggc acatgcgtaa               650
```

<210> SEQ ID NO 41
<211> LENGTH: 600
<212> TYPE: DNA
<213> ORGANISM: Artificial Sequence
<220> FEATURE:

<223> OTHER INFORMATION: synthetic construct

<400> SEQUENCE: 41

| | |
|---|---|
| agaaggtgaa cactgatgcc ccgccccaag ctcaagtccg atgacgaggt actcgaggcc | 60 |
| gccaccgtag tgctgaagcg ttgcggtccc atagagttca cgctcagcgg actagcaaag | 120 |
| gaggtggggc tctcccgcgc agcgttaatc cagcgcttca ccaaccgcga tacgctgctg | 180 |
| gtgaggatga tggagcgcgg cgtcgagcag gtgcggcatt acctgaatgc gataccgata | 240 |
| ggcgcagggc cgcaagggct ctgggaattt ttgcaggtgc tcgttcggag catgaacact | 300 |
| cgcaacgact tctcggtgaa ctatctcatc tcctggtacg agctccaggt gccggagcta | 360 |
| cgcacccttg cgatccagcg gaaccgcgcg gtggtggagg ggatccgcaa gcgactgccc | 420 |
| ccaggtgctc ctgcggcagc tgagttgctc ctgcactcgg tcatcgctgg cgcgacgatg | 480 |
| cagtgggccg tcgatccgga tggtgagcta gctgatcatg tgctggctca gatctctgcc | 540 |
| atcctgtgtt taatgtttcc cgaacacgac gatttccaac tcctccaggc acatgcgtaa | 600 |

<210> SEQ ID NO 42
<211> LENGTH: 600
<212> TYPE: DNA
<213> ORGANISM: Artificial Sequence
<220> FEATURE:
<223> OTHER INFORMATION: synthetic construct

<400> SEQUENCE: 42

| | |
|---|---|
| agaaggtgga cactgatgcc ccgccccaag ctcaagtccg atgacgaggt actcgaggcc | 60 |
| gccaccgtag tgctgaagcg ttgcggtccc attgagttca cgctcagcgg agtatcaaag | 120 |
| gaggtggggc tctcccgcgc agcgttaatc cagcgcttca ccaaccgcga tacgctgctg | 180 |
| gtgaggatga tggagcgcgg cgtcgagcag gtgcggcatt acctgaatgc gataccgata | 240 |
| ggcgcagggc cgcaagggct ctgggaattt ttgcaggtgc tcgttcggag catgaacact | 300 |
| cgcaacgact tctcggtgaa ctatctcatc tcctggtacg agctccaggt gccggagcta | 360 |
| cgcacgcttg cgatccagcg gaaccgcgcg gtggtggagg ggatccgcaa gcgactgccc | 420 |
| ccaggtgctc ctgcggcagc agagttgctc ctgcactcgg tcatcgctgg cgcgacgatg | 480 |
| cagtgggccg tcgatccgga tggtgagcta gctgatcatg tgctggctca gatcgctgcc | 540 |
| atcctgtgtt taatgtttcc cgaacacgac gatttccaac tcctccaggc acatgcgtaa | 600 |

<210> SEQ ID NO 43
<211> LENGTH: 650
<212> TYPE: DNA
<213> ORGANISM: Artificial Sequence
<220> FEATURE:
<223> OTHER INFORMATION: synthetic construct

<400> SEQUENCE: 43

| | |
|---|---|
| tggtgcaaaa cctttcgcgg tatgtcatga tagcgccccc caacccatac agaaggtgaa | 60 |
| cactgatgcc ccgccccaag ctcaagtccg atgacgaggt actcgaggcc gccaccgtag | 120 |
| tgctgaagcg ttgcggtccc atagagttca cgctcagcgg agtagcaaag gaggtggggc | 180 |
| tctcccgcgc agcgttaatc cagcgcttca ccaactgcga tacgctgctg gtgaggatga | 240 |
| tggagcgcgg cgtcgagcag gtgcggcatt acctgaatgc gataccgata ggcgcagggc | 300 |
| cgcaagggct ctgggaattt ttgcaggtgc tcgttcggag catgaacact cgcaacgact | 360 |
| tctcggtgaa ctatctcatc tcctggtacg agctccaggt gccggagcta cgcacgcttg | 420 |
| cgatccagcg gaaccgcgcg gtggtggagg ggatccgcaa gcgactgccc ccaggtgctc | 480 |

```
ctgcggcagc tgagttgctc ctgcactcgg tcatcgctgg cgcgacgatg cagtgggccg      540
tcgatccgga tggtgagcta gctgatcatg tgctggctca gatcgctgcc atcctgtgtt      600
taatgtttcc cgaacacgac gatttccaac tcctccaggc acatgcgtaa                650
```

<210> SEQ ID NO 44
<211> LENGTH: 600
<212> TYPE: DNA
<213> ORGANISM: Artificial Sequence
<220> FEATURE:
<223> OTHER INFORMATION: synthetic construct

<400> SEQUENCE: 44

```
agaaggtgaa cactgatgcc ccgccccaag ctcaagtccg atgacgaggt tctcgaggcc      60
accaccgtag tgctgaagcg ttgcggtccc atagagttca cgctcagtgg agtggcaaag     120
gaggtggggc tctcccgcgc agcgttaatc cagcgcttca ccaaccgcga tacgctgctg     180
gtgaggatga tggagcgcgg cgtcgagcag gtgcggcatt acctgaatgc gataccgata     240
ggcgcagggc cgcaagggct ctgggaattt ttgcaggtgc tcgttcggag catgaacact     300
cgcaacgact tctcggtgaa ctatctcatc tcctggtacg agctccaggt gccggagcta     360
cgcacgcttg cgatccagcg gaaccgcgcg gtagtggagg ggatccgcaa gcgactgccc     420
ccaggtgctc ctgcggcagc tgagttgctc ctgcactcgg tcatcgctgg cgcgatgaag     480
cagtgggccg tcgatccgga tggtgagcta gctgatcatg tgctggctca gatcgctgcc     540
atcctgtgtt taatgtttcc cgaacacgac gatttccaac tcctccaggc acatgcgtaa    600
```

<210> SEQ ID NO 45
<211> LENGTH: 600
<212> TYPE: DNA
<213> ORGANISM: Artificial Sequence
<220> FEATURE:
<223> OTHER INFORMATION: synthetic construct

<400> SEQUENCE: 45

```
agaaggtgaa cactgatgcc ccgcctcaag ctcaagtccg atgacgaggt actcgaggcc      60
gccaccgtag tgctgaagcg ttgcggtccc atagagttca cgctcagcgg agtagcaaag    120
gaggtggggc tctcccgcgc agcgttaatc cagcgcttca ccaaccgcga tacgctgctg    180
gtgaggatga tggagcgcgg cgtcgagcag gtgcggcatt acctgaatgc gataccgata    240
ggcgcagggc cgcaagggct ctgggaattt ttgcaggtgc tcgttcggag catgaacact    300
cgcaacgact tctcggtgaa ctatctcatc tccttgtacg agctccaggt gccggagcta    360
cgcacgcttg cgatccagcg gaaccgcgcg gtggtggagg ggatccgcaa gcgactgccc    420
ccaggtgctc ctgcggcagc tgagttgctc ctgcactcgg tcatcgctgg cgcgacgatg    480
cagtgggccg tcgatccgga tggtgagcta gctgatcatg tgctggctca gatcgctgcc    540
atcctgtgtt taatgtttcc cgaacacgac gatttccaac tcctccaggc acgtgcgtaa    600
```

<210> SEQ ID NO 46
<211> LENGTH: 600
<212> TYPE: DNA
<213> ORGANISM: Artificial Sequence
<220> FEATURE:
<223> OTHER INFORMATION: synthetic construct

<400> SEQUENCE: 46

```
agaaggtgaa cactgatgcc ccgccccaag ctcaagtccg atgacgaggt actcgaggcc      60
```

```
gccaccgtag tgctgaagcg ttgcggtccc atagagttca cgctcagcgg agtatcaaag      120
gaggtggggc tctcccgcgc agcgttaatc cagcgcttca ccaaccgcga tacgctgctg      180
gtgaggatga tggagcgcgg cgtcgagcag gtgcggcatt acctgaatgc gataccgata      240
ggcgcagggc cgcaagggct ctgggaattt ttgcaggtgc tcgttcggag catgaacact      300
cgcaacgact tctcggtgaa caatctcatc tcctggtacg agctccaggt gccggagcta      360
cgcacgcttg cgatccagcg gaaccgcgcg gtggtggagg ggatccgcaa gcgactgccc      420
ccaggtgctc ctgcggcagc tgagttgctc ctgcactcgg tcatcgctgg cgcgacgatg      480
cagtgggccg tcgatccgga tggtgagcta gctgatcatg tgctggctca gatcgctgcc      540
atcctgtgtt taatgtttcc cgaacacgac gatttccaat tcctccaggc acatgcgtaa      600
```

<210> SEQ ID NO 47
<211> LENGTH: 600
<212> TYPE: DNA
<213> ORGANISM: Artificial Sequence
<220> FEATURE:
<223> OTHER INFORMATION: synthetic construct

<400> SEQUENCE: 47

```
agaaggtgaa cactgatgcc ccgccccaag ctcaagtccg atgacgaggt actcgaggcc       60
gccaccgtag tgctgaagcg ttgcggtccc atagagttca cgctcagcgg agtagcaaag      120
gaggtggggc tctcccgcgc agcgttaatc cagcgcttca ccaaccgcga tacgctgctg      180
gtgaggatga tggagcgcgg cgtcgagcag ccacggcatt acctgaatgc gataccgata      240
ggcgcagggc cgcaagggct ctgggaattt ttgcaggtgc tcgttcggag catgaacact      300
cgcaacgact tctcggtgaa ctatctcatc tcctggtacg agctccaggt gccggagcta      360
cgcacgcttg cgatccagcg gaaccgcgcg gtggtggagg ggatccgcaa gcgactgccc      420
ccaggtgctc ctgcggcagc tgagttgctc ctgcactcgg tcatcgctgg cgcgacgatg      480
cagtgggccg tcgatccgga tggtgagcta gctgatcatg tgctggctca gatcgctgcc      540
atcctgtgtt taatgtttcc cgaacacgac gatttccaac tcctccaggc acatgcgtaa      600
```

<210> SEQ ID NO 48
<211> LENGTH: 600
<212> TYPE: DNA
<213> ORGANISM: Artificial Sequence
<220> FEATURE:
<223> OTHER INFORMATION: synthetic construct

<400> SEQUENCE: 48

```
agaaggtgaa cactgatgcc ccgccccaag ctcaagtccg atgacgaggt actcgaggcc       60
gccaccgtag tgctgaagcg ttgcggtccc atagagttca cgctcagcgg agtagcaaag      120
gaggtggggc tctcccgcgc agcgttaatc cagcgcttca ccaaccgcga tacgctgctg      180
gtgaggatga tggagcgcgg cgtcgagcag aggcggcatt acctgaatgc gataccgata      240
ggcgcagggc cgcaagggct ctgggaattt ttgcaggtgc tcgttcggag catgaacact      300
cgcaacgact tctcggtgaa ctatctcatc tcctggtacg agctccaggt gccggagcta      360
cgcacgcttg cgatccagcg gaaccgcgcg gtggtggagg ggatccgcaa gcgactgccc      420
ccaggtgctc ctgcggcagc tgagttgctc ctgcactcgg tcatcgctgg cgcgacgatg      480
cagtgggccg tcgatccgga tggtgagcta gctgatcatg tgctggctca gatcgctgcc      540
atcctgtgtt taatgtttcc cgaacacgac gatttccaac tcctccaggc acatgcgtaa      600
```

<210> SEQ ID NO 49
<211> LENGTH: 600
<212> TYPE: DNA
<213> ORGANISM: Artificial Sequence
<220> FEATURE:
<223> OTHER INFORMATION: synthetic construct

<400> SEQUENCE: 49

```
agaaggtgaa cactgatgcc ccgccccaag ctcaagtccg atgacgaggt actcgaggcc      60
gccaccgtag tgctgaagcg ttgcggtccc atagagttca cgctcagcgg agtagcaaag     120
gaggtggggc tctcccgcgc agcgttaatc cagcgcttca ccaaccgcga tacgctgctg     180
gtgaggatga tggagcgcgg cgtcgagcag ggacggcatt acctgaatgc gataccgata     240
ggcgcagggc cgcaagggct ctgggaattt ttgcaggtgc tcgttcggag catgaacact     300
cgcaacgact tctcggtgaa ctatctcatc tcctggtacg agctccaggt gccggagcta     360
cgcacgcttg cgatccagcg gaaccgcgcg gtggtggagg ggatccgcaa gcgactgccc     420
ccaggtgctc ctgcggcagc tgagttgctc ctgcactcgg tcatcgctgg cgcgacgatg     480
cagtgggccg tcgatccgga tggtgagcta gctgatcatg tgctggctca gatcgctgcc     540
atcctgtgtt taatgtttcc cgaacacgac gatttccaac tcctccaggc acatgcgtaa     600
```

<210> SEQ ID NO 50
<211> LENGTH: 600
<212> TYPE: DNA
<213> ORGANISM: Artificial Sequence
<220> FEATURE:
<223> OTHER INFORMATION: synthetic construct

<400> SEQUENCE: 50

```
agaaggtgaa cactgatgcc ccgccccaag ctcaagtccg atgacgaggt actcgaggcc      60
gccaccgtag tgctgaagcg ttgcggtccc atagagttca cgctcagcgg agtagcaaag     120
gaggtggggc tctcccgcgc agcgttaatc cagcgcttca ccaaccgcga tacgctgctg     180
gtgaggatga tggagcgcgg cgtcgagcag atccggcatt acctgaatgc gataccgata     240
ggcgcagggc cgcaagggct ctgggaattt ttgcaggtgc tcgttcggag catgaacact     300
cgcaacgact tctcggtgaa ctatctcatc tcctggtacg agctccaggt gccggagcta     360
cgcacgcttg cgatccagcg gaaccgcgcg gtggtggagg ggatccgcaa gcgactgccc     420
ccaggtgctc ctgcggcagc tgagttgctc ctgcactcgg tcatcgctgg cgcgacgatg     480
cagtgggccg tcgatccgga tggtgagcta gctgatcatg tgctggctca gatcgctgcc     540
atcctgtgtt taatgtttcc cgaacacgac gatttccaac tcctccaggc acatgcgtaa     600
```

<210> SEQ ID NO 51
<211> LENGTH: 600
<212> TYPE: DNA
<213> ORGANISM: Artificial Sequence
<220> FEATURE:
<223> OTHER INFORMATION: synthetic construct

<400> SEQUENCE: 51

```
agaaggtgaa cactgatgcc ccgccccaag ctcaagtccg atgacgaggt actcgaggcc      60
gccaccgtag tgctgaagcg ttgcggtccc atagagttca cgctcagcgg agtagcaaag     120
gaggtggggc tctcccgcgc agcgttaatc cagcgcttca ccaaccgcga tacgctgctg     180
gtgaggatga tggagcgcgg cgtcgagcag gaccggcatt acctgaatgc gataccgata     240
ggcgcagggc cgcaagggct ctgggaattt ttgcaggtgc tcgttcggag catgaacact     300
```

```
cgcaacgact tctcggtgaa ctatctcatc tcctggtacg agctccaggt gccggagcta    360
cgcacgcttg cgatccagcg gaaccgcgcg gtggtggagg ggatccgcaa gcgactgccc    420
ccaggtgctc ctgcggcagc tgagttgctc ctgcactcgg tcatcgctgg cgcgacgatg    480
cagtgggccg tcgatccgga tggtgagcta gctgatcatg tgctggctca gatcgctgcc    540
atcctgtgtt taatgtttcc cgaacacgac gatttccaac tcctccaggc acatgcgtaa    600
```

<210> SEQ ID NO 52
<211> LENGTH: 600
<212> TYPE: DNA
<213> ORGANISM: Artificial Sequence
<220> FEATURE:
<223> OTHER INFORMATION: synthetic construct

<400> SEQUENCE: 52

```
agaaggcgaa cactgatgcc ccgccccaag ctcaagtccg atgacgaggt actcgaggcc     60
gccaccgtag tgctgaagcg ttgcggtccc atagagttca cgctcagcgg agtagcaaag    120
gaggtggggc tctcccgcgc agcgttaatc cagcgcttca tcaaccgcga tacgctgctg    180
gtgaggatga tggagcgcgg cgtcgagcag gtgcggcatt acctgaatgc gataccgata    240
ggcgcagggc gcaagggct ctgggaattt ttgcaggtgt tcgttcggag catgaacact    300
cgcaacaact tctcggtgaa ctatctcatc tcctggtacg atctccaggt gccggagcta    360
cgcacgcttg cgatccagcg gaaccgcgcg gtggtggagg ggatccgcaa gcgactgccc    420
ccaggtgctc ctgcggcagc tgagttgctc ctgcactcgg tcatcgctgg cgcgacgatg    480
cagtgggccg tcgatccgga tggtgagcta gctgatcatg tgctggctca gatcgctgcc    540
atcctgtgtt taatgtttcc cgaacacgac gatttccaac tcctccaggc acatgcgtaa    600
```

<210> SEQ ID NO 53
<211> LENGTH: 600
<212> TYPE: DNA
<213> ORGANISM: Artificial Sequence
<220> FEATURE:
<223> OTHER INFORMATION: synthetic construct

<400> SEQUENCE: 53

```
ttcaggtgaa cactgatgcc ccgccccaag ctcaagtccg atgacgaggt actcgaggcc     60
gccaccgtag tgctgaagcg ttgcggtccc atagagttca cgctcagcgg agtagcaaag    120
gaggtggggc tctcccgcgc agcgttaatc cagcgcttca ccaaccgcga tacgctgctg    180
gtgaggatga tggagcgcgg cgtcgagcag gtgcggcatt acctgaatgc gataccgata    240
ggcgcagggc cgcaagggct ctgggaattt ttgcaggtgc tcgttcggag catgaacact    300
cgcaacgact tctcggtgaa ctatctcatc tcctggtacg agctccaggt gccggagcta    360
cgcacgcttg cgatccagcg gaaccgcgcg gtggtggagg ggatccgcaa gcgactgccc    420
ccaggtgctc ctgcggcagc tgagttgctc ctgcactcgg tcatcgctgg cgcgacgatg    480
cagtgggccg tcgatccgga tggtgagcta gctgatcatg tgctggctca gatcgctgcc    540
atcctgtgtt taatgtttcc cgaacacgac gatttccaac tcctccaggc acatgcgtaa    600
```

<210> SEQ ID NO 54
<211> LENGTH: 600
<212> TYPE: DNA
<213> ORGANISM: Artificial Sequence
<220> FEATURE:
<223> OTHER INFORMATION: synthetic construct

<400> SEQUENCE: 54

```
ctgaggtgaa cactgatgcc ccgccccaag ctcaagtccg atgacgaggt actcgaggcc    60
gccaccgtag tgctgaagcg ttgcggtccc atagagttca cgctcagcgg agtagcaaag   120
gaggtggggc tctcccgcgc agcgttaatc cagcgcttca ccaaccgcga tacgctgctg   180
gtgaggatga tggagcgcgg cgtcgagcag gtgcggcatt acctgaatgc gataccgata   240
ggcgcagggc cgcaagggct ctgggaattt ttgcaggtgc tcgttcggag catgaacact   300
cgcaacgact tctcggtgaa ctatctcatc tcctggtacg agctccaggt gccggagcta   360
cgcacgcttg cgatccagcg gaaccgcgcg gtggtggagg ggatccgcaa gcgactgccc   420
ccaggtgctc ctgcggcagc tgagttgctc ctgcactcgg tcatcgctgg cgcgacgatg   480
cagtgggccg tcgatccgga tggtgagcta gctgatcatg tgctggctca gatcgctgcc   540
atcctgtgtt taatgtttcc cgaacacgac gatttccaac tcctccaggc acatgcgtaa   600
```

<210> SEQ ID NO 55
<211> LENGTH: 600
<212> TYPE: DNA
<213> ORGANISM: Artificial Sequence
<220> FEATURE:
<223> OTHER INFORMATION: synthetic construct

<400> SEQUENCE: 55

```
aaaaggtgaa cactgatgcc ccgccccaag ctcaagtccg atgacgaggt actcgaggcc    60
gccaccgtag tgctgaagcg ttgcggtccc atagagttca cgctcagcgg agtagcaaag   120
gaggtggggc tctcccgcgc agcgttaatc cagcgcttca ccaaccgcga tacgctgctg   180
gtgaggatga tggagcgcgg cgtcgagcag gtgcggcatt acctgaatgc gataccgata   240
ggcgcagggc cgcaagggct ctgggaattt ttgcaggtgc tcgttcggag catgaacact   300
cgcaacgact tctcggtgaa ctatctcatc tcctggtacg agctccaggt gccggagcta   360
cgcacgcttg cgatccagcg gaaccgcgcg gtggtggagg ggatccgcaa gcgactgccc   420
ccaggtgctc ctgcggcagc tgagttgctc ctgcactcgg tcatcgctgg cgcgacgatg   480
cagtgggccg tcgatccgga tggtgagcta gctgatcatg tgctggctca gatcgctgcc   540
atcctgtgtt taatgtttcc cgaacacgac gatttccaac tcctccaggc acatgcgtaa   600
```

<210> SEQ ID NO 56
<211> LENGTH: 600
<212> TYPE: DNA
<213> ORGANISM: Artificial Sequence
<220> FEATURE:
<223> OTHER INFORMATION: synthetic construct

<400> SEQUENCE: 56

```
agaaggtgaa cactgatgcc ccgccccaag ctcaagtccg atgacgaggt actcgaggcc    60
gccaccgtag tgctgaagcg ttgcggtccc atagagttca cgctcagcgg agtagcaaag   120
gaggtgggac tctcccgcgc agcgttaatc cagcgcttca ccaaccgcga tacgctgctg   180
gtgaggatga tggagcgcgg cgtcgagcag gtgcggcatt acctgaatgc gataccgata   240
ggcgcagggc cgcaagggct ctgggaattt ttgcaggtgc tcgttcggag catgaacact   300
cgcaacgact tctcggtgaa ctatctcatc tcctggtacg agctccaggt gccggagcta   360
cgcacgcttg cgatccagac taaccgcgcg gtggtggagg ggatccgcaa tcgactgccc   420
ccaggtgctc ctgcggcagc tgagttgctc ctgcactcgg tcatcactgg cgcgacgatg   480
cagtgggccg tcgatccgga tggtgagcta gctgatcatg tgctggctca gatcgctgcc   540
```

```
atcctgtgtt taatgtttcc cgaacaagac gatttccaac tcctccaggc acatgcgtaa    600

<210> SEQ ID NO 57
<211> LENGTH: 600
<212> TYPE: DNA
<213> ORGANISM: Artificial Sequence
<220> FEATURE:
<223> OTHER INFORMATION: synthetic construct

<400> SEQUENCE: 57
agatggtgaa cactgatgcc ccgccccaag ctcaagtccg atgacgaggt actcgaggcc     60
gccaccgtag tgctgaagcg ttgcggtccc atagagttca cgctcagcgg agtagcaaag    120
gaggtgggac tctcccgcgc agcgttaatc cagcgcttca ccaaccgcga tacgctgctg    180
gtgaggatga tggagcgcgg cgtcgagcag gtgcggcatt acctgaatgc gataccgata    240
ggcgcagggc cgcaagggct ctgggaattt ttgcaggtgc tcgttcggag catgaacact    300
cgcaacgact tctcggtgaa ctatctcatc tcctggtacg agctccaggt gccggagcta    360
cgcacgcttg cgatccagac taaccgcgcg gtggtgagg ggatccgcaa tcgactgccc     420
ccaggtgctc ctgcggcagc tgagttgctc ctgcactcgg tcatcactgg cgcgacgatg    480
cagtgggccg tcgatccgga tggtgagcta gctgatcatg tgctggctca gatcgctgcc    540
atcctgtgtt taatgtttcc cgaacaagac gatttccaac tcctccaggc acatgcgtaa    600

<210> SEQ ID NO 58
<211> LENGTH: 585
<212> TYPE: DNA
<213> ORGANISM: Artificial Sequence
<220> FEATURE:
<223> OTHER INFORMATION: synthetic construct

<400> SEQUENCE: 58
atgccccgcc ccaagctcaa gtccgatgac gaggtactcg aggccgccac cgtagtgctg     60
aagcgttgcg gtcccataga gttcacgctc agcggagtag caaaggaggt gggactctcc    120
cgcgcagcgt taatccagcg cttcaccaac cgcgatacgc tgctggtgag gatgatggag    180
cgcggcgtcg agcaggtgcg gcattacctg aatgcgatac cgataggcgc agggccgcaa    240
gggctctggg aattttttgca ggtgctcgtt cggagcatga acactcgcaa cgacttctcg    300
gtgaactatc tcatctcctg gtacgagctc caggtgccgg agctacgcac gcttgcgatc    360
cagactaacc gcgcggtggt ggaggggatc cgcaatcgac tgcccccagg tgctcctgcg    420
gcagctgagt tgctcctgca ctcggtcatc actggcgcga cgatgcagtg ggccgtcgat    480
ccggatggtg agctagctga tcatgtgctg gctcagatcg ctgccatcct gtgtttaatg    540
tttcccgaac aagacgattt ccaactcctc caggcacatg cgtaa                    585

<210> SEQ ID NO 59
<211> LENGTH: 585
<212> TYPE: DNA
<213> ORGANISM: Artificial Sequence
<220> FEATURE:
<223> OTHER INFORMATION: synthetic construct

<400> SEQUENCE: 59
atgccccgcc ccaagctcaa gtccgatgac gaggtactcg aggccgccac cgtagtgctg     60
aagcgttgcg gtcccataga gttcacgctc agcggagtag caaaggaggt gggactctcc    120
cgcgcagcgt taatccagcg cttcaccaac cgcgatacgc tgctggtgag gatgatggag    180
cgcggcgtcg agcaggtgcg gcattacctg aatgcgatac cgataggcgc agggccgcaa    240
```

```
gggctctggg aatttttgca ggtgctcgtt cggagcatga acactcgcaa cgacttctcg      300
gtgaactatc tcatctcctg gtacgagctc caggtgccgg agctacgcac gcttgcgatc      360
cagactaacc gcgcggtggt ggaggggatc cgcaatcgac tgcccccagg tgctcctgcg      420
gcagctgagt tgctcctgca ctcggtcatc actggcgcga cgatgcagtg ggccgtcgat      480
ccggatggtg agctagctga tcatgtgctg gctcagatcg ctgccatcct gtgtttaatg      540
tttcccgaac aagacgattt ccaactcctc caggcacatg cgtaa                      585
```

We claim:

1. A biosensor system comprising:
   a nucleic acid encoding a genetically modified MphR gene sequence, wherein the nucleic acid comprises at least one genetic mutation comprising at least one nucleotide change in the ribosome binding site sequence when compared to a wild-type MphR gene sequence; and
   a reporter gene whose transcription is under the control of a promoter region which is regulated by a wild-type MphR transcription factor.

2. The biosensor system of claim 1, wherein the nucleic acid encoding the genetically modified MphR gene sequence and the reporter gene are located on one recombinant DNA vector.

3. The biosensor system of claim 1, wherein the reporter gene is a gene coding for chloramphenicol acetyltransferase, beta-galactosidase, luciferase or green fluorescent protein (GFP).

4. The biosensor system of claim 3, wherein the reporter gene is a gene coding for green fluorescent protein (GFP).

5. The biosensor system of claim 1, wherein the at least one nucleotide change in the ribosome binding site sequence is selected from A1G, A1T, A1C, G2T, G2A, A3C, A3G, A4T, G5T, G6T, or a combination thereof.

6. The biosensor system of claim 1, wherein the at least one nucleotide change in the ribosome binding site sequence is selected from A1G, A4T, or a combination thereof.

7. A genetically modified host cell comprising:
   a nucleic acid encoding the biosensor system of claim 1.

8. The cell of claim 7, wherein the at least one nucleotide change in the ribosome binding site sequence is selected from A1G, A1T, A1C, G2T, G2A, A3C, A3G, A4T, G5T, G6T, or a combination thereof.

9. The cell of claim 7, wherein the cell is *E. coli*.

10. The cell of claim 7, wherein the cell is *Streptomyces*.

11. A method for detecting a polyketide, comprising:
    introducing into a cell:
    a nucleic acid encoding a genetically modified MphR gene sequence, wherein the nucleic acid comprises at least one nucleotide change in the ribosome binding site sequence when compared to a wild-type MphR gene sequence;
    and
    a reporter gene whose transcription is under the control of a promoter region which is regulated by a wild-type MphR transcription factor; and
    detecting the presence or absence of the polyketide based on the differential expression of the reporter gene in comparison to a cell comprising the wild-type MphR gene sequence.

12. The method of claim 11, wherein the at least one nucleotide change in the ribosome binding site sequence is selected from A1G, A1T, A1C, G2T, G2A, A3C, A3G, A4T, G5T, G6T, or a combination thereof.

13. The method of claim 11, wherein the cell is *E. coli*.

14. The method of claim 11, wherein the cell is *Streptomyces*.

* * * * *